(12) United States Patent
Boyce et al.

(10) Patent No.: US 6,190,887 B1
(45) Date of Patent: Feb. 20, 2001

(54) EXPRESSION OF AN EXOGENOUS GENE IN A MAMMALIAN CELL BY USE OF A NON-MAMMALIAN DNA VIRUS HAVING AN ALTERED COAT PROTEIN

(75) Inventors: Frederick M. Boyce, Belmont; James G. Barsoum, Lexington, both of MA (US)

(73) Assignees: The General Hospital Corporation, Boston; Biogen, Inc., Cambridge, both of MA (US)

( * ) Notice: Under 35 U.S.C. 154(b), the term of this patent shall be extended for 0 days.

(21) Appl. No.: 09/514,953

(22) Filed: Feb. 28, 2000

Related U.S. Application Data

(62) Division of application No. 08/927,317, filed on Sep. 11, 1997.
(60) Provisional application No. 60/026,297, filed on Sep. 11, 1996.

(51) Int. Cl.$^7$ .............................. C12P 21/04; C12P 21/06; G01N 33/574; C12N 15/70; A61K 39/07
(52) U.S. Cl. ................ 435/69.7; 435/7.23; 435/69.1; 435/320.1; 514/12; 424/246.1
(58) Field of Search ................... 435/69.7, 7.23, 435/920.1, 69.1, 230.1

(56) References Cited

U.S. PATENT DOCUMENTS

| | | | |
|---|---|---|---|
| 4,745,051 | 5/1988 | Smith et al. | 435/68 |
| 4,879,236 | 11/1989 | Smith et al. | 435/235 |
| 4,914,027 | 4/1990 | Knapp et al. | 435/69.6 |
| 5,004,687 | 4/1991 | Miller | 435/69.1 |
| 5,106,741 | 4/1992 | Marotti et al. | 435/22.6 |
| 5,476,781 | 12/1995 | Moyer et al. | 435/240.2 |

FOREIGN PATENT DOCUMENTS

| | | |
|---|---|---|
| WO 92/14829 | 9/1992 | (WO). |
| WO 95/23866 | 9/1995 | (WO). |
| WO 95/26409 | 10/1995 | (WO). |
| WO 96/09074 | 3/1996 | (WO). |

OTHER PUBLICATIONS

Fraser; "The baculovirus–infected insect cell as a eukaryotic gene expression system", Curr. Top. Microbiol. Immunol., 158:131–172 (1992).

Yi Li, et al., "Transient, Nonlethal Expression of Genes in Vertebrate Cells by Recombinant Entomopoxviruses", Journal of Virology, Dec. 1997, pp. 9557–9562.

Yvan Boublik, et al., "Eukaryotic Virus Display: Engineering the Major Surface Glycoprotein of the *Autographa cailfornica* Nuclear Polyhedrosis Virus (AcNPV) for the Presentation of Foreign Proteins on the Virus Surface", Bio/Technology, vol. 13, pp. 1079–1084, Oct. 1995.

Young J.A.T. et al.; "Efficient Incorporation of Human CD4 Protein into Avian Leukosis Virus Particles"; Science 250:1421–1423 (1990).

James Barsoum, et al., "Efficient Transduction of Mammalian Cells by a Recombinant Baculovirus Having Vesicular Stomatitis Virus G Glycoprotein", Human Gene Therapy, 8:2011–2018 (Nov. 20, 1997).

(List continued on next page.)

*Primary Examiner*—Hankyel Park
(74) *Attorney, Agent, or Firm*—Sterne, Kessler, Goldstein & Fox PLLC

(57) ABSTRACT

Disclosed are methods, nucleic acids, and cells for expressing an exogenous gene in a mammalian cell, involving introducing into the cell a non-mammalian DNA virus (e.g., a baculovirus) having an altered coat protein, the genome of which virus carries an exogenous gene, and growing the cell under conditions such that the gene is expressed. Also disclosed are methods for treating gene deficiency disorders, neurological disorders, or cancers in a mammal by (1) providing to a cell a therapeutically effective amount of a non-mammalian DNA virus having an altered coat protein, the genome of which virus carries an exogenous, therapeutic gene and (2) growing the cell under conditions such that the exogenous gene is expressed in the mammal.

21 Claims, 31 Drawing Sheets

OTHER PUBLICATIONS

Miguel A. Trujillo, et al., "Functional analysis of a liver–specific enhancer of the hepatitis B virus", Proc. Natl. Acad. Sci., 88:3797–3801, (May 1991).

Volkman, et al.; "In Vitro Survey of *Autographa Californica* Nuclear Polyhedrosis Virus Interaction with Nontarget Vetebrate Host Cells", Applied and Environmental Microbiology, 45:1085–1093, 1983.

Brusca et al., "*Autographa Californica* Nuclear Polyhedrosis Virus Efficiently Enters but Does Not Replicate in Poikilothermic Vertebrate Cells", Intervirology 26:207–222, 1986.

Hoopes et al., "In Vitro Transcription of Baculovirus Immediate Early Genes: Accurate mRNA Initiation By Nuclear Extracts from Both Insect and Human Cells", Proc. Natl. Acad. Sci., 88:4513–4517, 1991.

Huber et al., "Retroviral–mediated Gene Therapy for the Treatment of Hepatocellular Carcinoma: An Innovative Approach for Cancer Therapy", Proc. Natl. Acad. Sci., 88:8039–8043, 1991.

Lodish H.F.; "Recognition of Complex Oligosaccharides by the Multi–Subunit Asialoglycoprotein Receptor"; Elsevier Science Publishers 374–377 (1991).

Maestri N.E. et al.; "Prospective Treatment of Urea Cycle Disorders"; J. of Pediatrics 119:923–928 (1991).

McGrane M.M. et al.; "Metabolic Control of Gene Expression:In Vivo Studies With Transgenic Mice"; Elsevier Science Publishers 17:40–44 (1992).

Midoux P. et al.; "Specific Gene Transfer Mediated by Lactosylated Poly–L–Lysine into Hepatoma Cells"; Nucleic Acids Research 21:871–878 (1993).

Mulligan R.C.; "The Basic Science of Gene Therapy"; Science 260:926–932 (1993).

Patel et al., "A New Method for the Isolation of Recombinant Baculovirus", Nucleic Acids Research, 20:97–104, 1992.

Rana et al., "Cell–Extracellular Matrix Interactions Can Regulate the Switch Between Growth and Differentiation in Rat Hepatocytes . . . ", Molecular and Cellular Biology, 14:5858–5869, 1994.

Tjia et al., "*Autographa Californicia* Nuclear Polyhedrosis Virus (AcNPV) DNA Does Not Persist in Mass Cultures of Mammalian Cells", Virology, 125:107–117, 1983.

Vile et al., "Gene Transfer Technologies for the Gene Therapy of Cancer", Gene Therapy, 1:88–98, 1994.

School of Biological Sciences, Canberra, Australia, 1991.

Boyce, F.M. et al.(1996) "Baculovirus—Mediated Gene Transfer Into Mammalian Cells", Proc. Nat'l. Acad. Sci., USA 93:2348–2352.

Chan–Choo Yap, et al., A Hybrid Baculovirus—T7 RNA Polymerase System for Recovery of an Infectious Virus from cDNA, Virology, 231:192–200 (1997).

Wu G.Y. et al.; "Targeting Genes:Delivery and Persistent Expression of a Foreign Gene Driven by Mammalian Regulatory Elements in Vivo"; J. Biological Chemistry 264:16985–16987 (1989).

Grompe M. et al.; "Gene Therapy in Man and Mice:Adenosine Deaminase Deficiency, Ornithine Transcarbamylase Deficiency, and Duchenne Muscular Dystrophy"; Adv. in Experimental Medicine & Biology 309B:51–56 (1991).

Ashwell G. et al.; "Carbohydrate—Specific Receptors of the Liver"; Ann. Rev. Biochem. 51:531–54 (1982).

Groner, et. al; "Interaction of *Autographa californica* Nuclear Polyhedrosis Virus with Two Nonpermissive Cell Lines"; Intervirology 21:203–209 (1984).

Hartig P.C. et al.; "Insect Virus:Assays for Toxic Effects and Transformation Potential in Mammalian Cells"; Applied and Environmental Microbiology 55:1916–1920 (1989).

Hartig P.C. et al.; "Insect Virus Assays for Viral Replication and Persistence in Mammalian Cells"; J. Virological Methods 31:335–344 (1991).

Hata A. et al.; "Structure of the Human Ornithine Transcarbamylase Gene"; J. Biochem (Tokyo) 103:302–308, 1988.

Grompe M. et al.; "Retroviral—Mediated Gene Transfer of Human Ornithine Transcarbamylase into Primary Hepatocytes of spf and spf–ash Mice"; Human Gene Therapy 3:35–44 (1992).

Carbonell L.F. et al.; "Baculovirus—Mediated Expression of Bacterial Genes in Dipteran and Mammalian Cells"; Journal of Virology, 56:153–160 (1985).

Demetriou A.A. et al.; "Replacement of Liver Function in Rats by Transplantation of Microcarrier–Attached Hepatocytes"; Science 233:1190–1192 (1986).

Jones S.N. et al.; "Ectopic Correction of Ornithine Transcarbamylase Deficiency in Sparse Fur Mice"; J. Biological Chemistry 265:14684–14690 (1990).

Demarquoy J.; "Retroviral—Mediated Gene Therapy for the Treatment of Citrullinemia. Transfer and Expression of Argininosuccinate Synthetase in Human Hematopoietic Cells"; Experientia 49:345–348 (1993).

Burns J.C. et al.; "Vesicular Stomatitis Virus G Glycoprotein Pseudotyped Retroviral Vectors:Concentration to Very High Titer and Efficient Gene Transfer into . . . "; Proc. Natl. Acad. Sci. USA; 90:8033–8037 (1993).

Cotten M. et al.; "Receptor—Mediated Transport of DNA into Eukaryotic Cells"; Academic Press, Inc. 217:618–644 (1993).

Kasahara, et al.; "Tissue—Specific Targeting of Retroviral Vectors Through Ligand—Receptor Interactions"; Science 266:1373–1376 (1994).

Shen R. et al.; "Tissue–Specific Regulation of Human 1–Antitrypsin Gene Expression in Transgenic Mice"; DNA 8:101–108 (1989).

Blissard G.W. et al.; "Baculovirus gp64 Envelope Glycoprotein Is Sufficient to Mediate pH–Dependent Membrane Fusion"; J. of Virology 66:6829–6835 (1992).

Burhans W.C. et al.; "DNA Replication Orgins in Animal Cells:A Question of Context?"; Science 263:639–640 (1994).

Shimada T. et al.; "Correction of Ornithine Transcarbamylase (OTC) Deficiency in spf–ash Mice by Introduction of Rat OTC Gene"; Elsevier Science Publishers 279:198–200 (1991).

Carbonell L.F. et al.; "Baculovirus Interaction with Nontarget Organisms:A Virus–Borne Reporter Gene Is Not Expressed in Two Mammalian Cell Lines"; Applied and Environmental Microbiology 53:1412–1417 (1987).

Spiess, Martin; "The Asialoglycoprotein Receptor: A Model for Endocytic Transport Receptors"; Biochemistry 29:10009–10018 (1990).

Charreau B. et al; "Establishment of Porcine Cell Lines Producing a Murine Recombinant Retrovirus in Order to Transfer the nlslacZ Gene into Porcine Cells"; Res. Virol. 142:343–351 (1991).

Horwich A.L.; "Inherited Hepatic Enzyme Defects as Candidates for Liver–Directed Gene Therapy"; Current Topics in Microbiology and Immunology 168:185–200 (1991).

Hodges P.E. et al.; "The spfash Mouse:A Missense Mutation in the Ornithine Transcarbamylase Gene Also Causes Aberrant mRNA Splicing"; Proc. Natl. Acad. Sci. USA 86:4142–4146 (1989).

Cristiano R.J. et al.; "Hepatic Gene Therapy:Adenovirus Enhancement of Receptor–Mediated Gene Delivery and Expression in Primary Hepatocytes"; Proc. Natl. Acad. Sci. USA 90:2122–2126 (1993).

Jung, et al.; "A Novel–Galactoside–Binding Lectin in Adult Rat Kidney"; J. Biochem. 116:547–553 (1994).

Stratford–Perricaudet et al.; "Evaluation of the Transfer and Expression in Mice of an Enzyme–Encoding Gene Using a Human Adenovirus Vector"; Human Gene Therapy 1:241–256 (1990).

Tan S.; "Liver–Specific and Position–Effect Expression of a Retinol–Binding Protein–lacZ Fusion Gene (RBP–lacZ) in Transgenic Mice"; Developmental Biology 146:24–37 (1991).

Ikuo Shoji, et al., Efficient gene transfer into various mammalian cells, including non–hepatic cells, by baculovirus vectors, Journal of General Virology, 78:2657–2664 (1997).

Wagner E. et al.; "Transferrin–Polycation Conjugates as Carriers for DNA Uptake into Cells"; Proc. Natl. Acad. Sci. USA 87:3410–3414 (1990).

Wilson J.M. et al.; "A Novel Mechanism for Achieving Transgene Persistence in Vivo After Somatic Gene Transfer into Hepatocytes"; Journal of Biological Chemistry 267:11483–11489 (1992).

Blissard G.W. et al.; "Baculovirus Diversity and Molecular Biology"; Annu. Rev. Entomol. 35:127–55 (1990).

Barbara Gloker, et al., In Vitro Transactivation of Baculovirus Early Genes by Nuclear Extracts from *Autographa californica* Nuclear Polyhedrosis Virus–Infected *Spodoptera frugiperda* Cells, Journal of Virology, 3476–3484 (Jun. 1992).

Wu G.Y. et al.; "Receptor—Mediated in Vitro Gene Transformation by a Soluble DNA Carrier System"; J. Biological Chemistry 262:4429–4432 (1987).

Wu G.Y. et al.; "Receptor—Mediated Gene Delivery and Expression in Vivo"; 263:14621–14624 (1988).

Wu G.Y. et al.; "Evidence for Targeted Gene Delivery to Hep G2 Hepatoma Cells in Vitro"; Biochemistry 27:887–892 (1988).

Wu G.Y. et al.; "Receptor—Mediated Gene Delivery in Vivo"; J. Biological Chemistry 266:14338–14342 (1991).

Wilson J.M. et al.; "Hepatocyte—Directed Gene Transfer In Vivo Leads to Transient Improvement of Hypercholesterolemia in Low Density Lipoprotein . . . "; J. Biol. Chemistry 267:963–967 (1992).

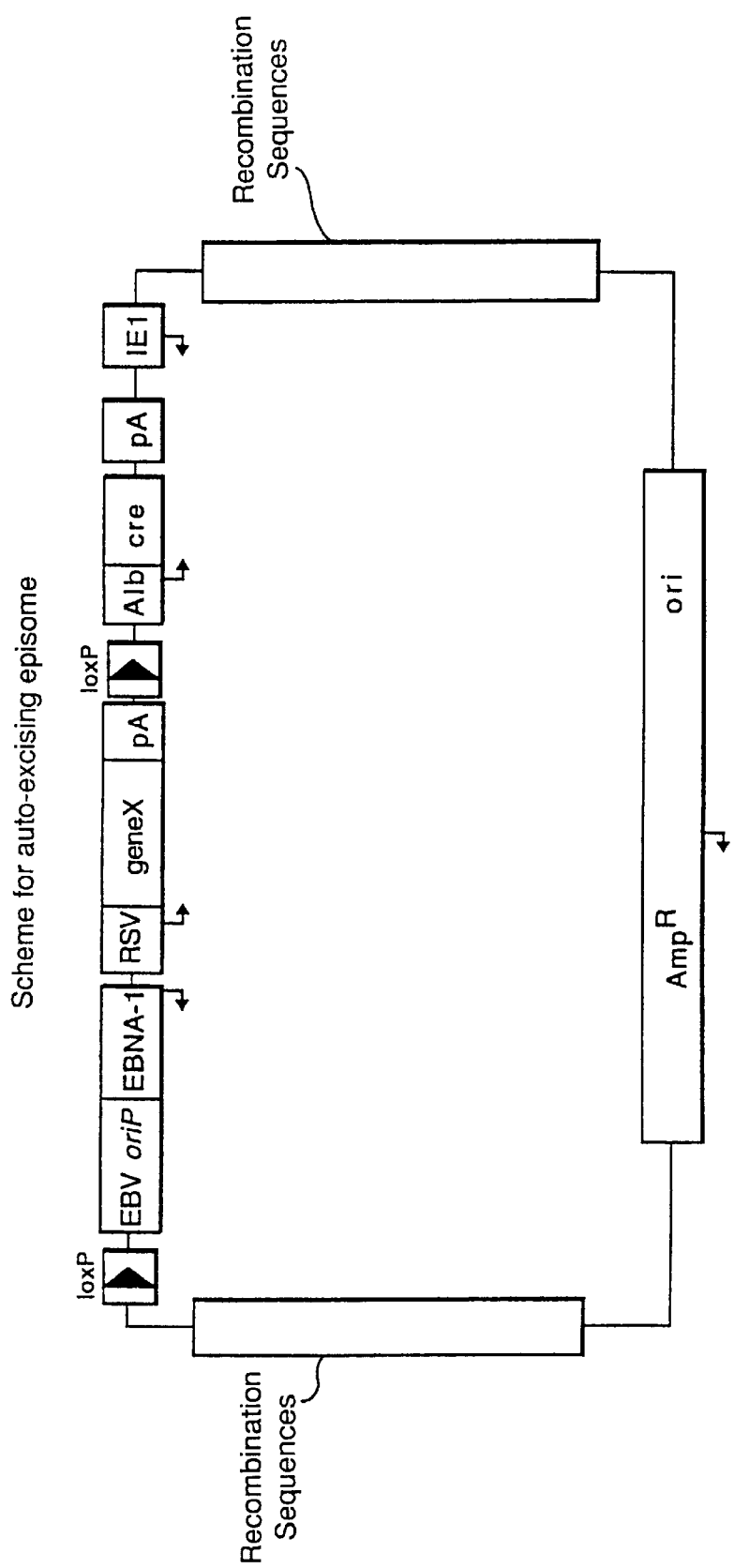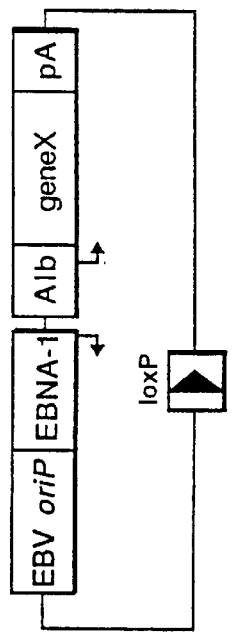

```
   1  AACGGCTCCG CCCACTATTA ATGAAATTAA AAATTCCAAT TTTAAAAAAC
  51  GCAGCAAGAG AAACATTTGT ATGAAAGAAT GCGTAGAAGG AAAGAAAAAT
 101  GTCGTCGACA TGCTGAACAA CAAGATTAAT ATGCCTCCGT GTATAAAAAA
 151  AATATTGAAC GATTTGAAAG AAAACAATGT ACCGCGCGGC GGTATGTACA
 201  GGAAGAGGTT TATACTAAAC TGTTACATTG CAAACGTGGT TTCGTGTGCC
 251  AAGTGTGAAA ACCGATGTTT AATCAAGGCT CTGACGCATT TCTACAACCA
 301  CGACTCCAAG TGTGTGGGTG AAGTCATGCA TCTTTTAATC AAATCCCAAG
 351  ATGTGTATAA ACCACCAAAC TGCCAAAAAA TGAAAACTGT CGACAAGCTC
 401  TGTCCGTTTG CTGGCAACTG CAAGGGTCTC AATCCTATTT GTAATTATTG
 451  AATAATAAAA CAATTATAAA TGCTAAATTT GTTTTTTATT AACGATACAA
 501  ACCAAACGCA ACAAGAACAT TTGTAGTATT ATCTATAATT GAAAACGCGT
 551  AGTTATAATC GCTGAGGTAA TATTTAAAAT CATTTTCAAA TGATTCACAG
 601  TTAATTTGCG ACAATATAAT TTTATTTTCA CATAAACTAG ACGCCTTGTC
 651  GTCTTCTTCT TCGTATTCCT TCTCTTTTTC ATTTTTCTCC TCATAAAAAT
 701  TAACATAGTT ATTATCGTAT CCATATATGT ATCTATCGTA TAGAGTAAAT
 751  TTTTTGTTGT CATAAATATA TATGTCTTTT TTAATGGGGT GTATAGTACC
 801  GCTGCGCATA GTTTTTCTGT AATTTACAAC AGTGCTATTT TCTGGTAGTT
 851  CTTCGGAGTG TGTTGCTTTA ATTATTAAAT TTATATAATC AATGAATTTG
 901  GGATCGTCGG TTTTGTACAA TATGTTGCCG GCATAGTACG CAGCTTCTTC
 951  TAGTTCAATT ACACCATTTT TTAGCAGCAC CGGATTAACA TAACTTTCCA
1001  AAATGTTGTA CGAACCGTTA AACAAAAACA GTTCACCTCC CTTTTCTATA
1051  CTATTGTCTG CGAGCAGTTG TTTGTTGTTA AAAATAACAG CCATTGTAAT
1101  GAGACGCACA AACTAATATC ACAAACTGGA ATGTCTATC AATATATAGT
1151  TGCTGATATC ATGGAGATAA TTAAAATGAT AACCATCTCG CAAATAAATA
1201  AGTATTTTAC TGTTTTCGTA ACAGTTTTGT AATAAAAAAA CCTATAAATA
1251  CGGATCCCTC GAGGAATTCT GACACTATGA AGTGCCTTTT GTACTTAGCC
1301  TTTTTATTCA TTGGGGTGAA TTGCAAGTTC ACCATAGTTT TTCCACACAA
```

FIG.23A

1351 CCAAAAAGGA AACTGGAAAA ATGTTCCTTC TAATTACCAT TATTGCCCGT
1401 CAAGCTCAGA TTTAAATTGG CATAATGACT TAATAGGCAC AGCCTTACAA
1451 GTCAAAATGC CAAGAGTCA CAAGGCTATT CAAGCAGACG GTTGGATGTG
1501 TCATGCTTCC AAATGGGTCA CTACTTGTGA TTTCCGCTGG TATGGACCGA
1551 AGTATATAAC ACATTCCATC CGATCCTTCA CTCCATCTGT AGAACAATGC
1601 AAGGAAAGCA TTGAACAAAC GAAACAAGGA ACTTGGCTGA ATCCAGGCTT
1651 CCCTCCTCAA AGTTGTGGAT ATGCAACTGT GACGGATGCC GAAGCAGTGA
1701 TTGTCCAGGT GACTCCTCAC CATGTGCTGG TTGATGAATA CACAGGAGAA
1751 TGGGTTGATT CACAGTTCAT CAACGGAAAA TGCAGCAATT ACATATGCCC
1801 CACTGTCCAT AACTCTACAA CCTGGCATTC TGACTATAAG GTCAAAGGGC
1851 TATGTGATTC TAACCTCATT TCCATGGACA TCACCTTCTT CTCAGAGGAC
1901 GGAGAGCTAT CATCCCTGGG AAAGGAGGGC ACAGGGTTCA GAAGTAACTA
1951 CTTTGCTTAT GAAACTGGAG GCAAGGCCTG CAAAATGCAA TACTGCAAGC
2001 ATTGGGGAGT CAGACTCCCA TCAGGTGTCT GGTTCGAGAT GGCTGATAAG
2051 GATCTCTTTG CTGCAGCCAG ATTCCCTGAA TGCCCAGAAG GGTCAAGTAT
2101 CTCTGCTCCA TCTCAGACCT CAGTGGATGT AAGTCTAATT CAGGACGTTG
2151 AGAGGATCTT GGATTATTCC CTCTGCCAAG AAACCTGGAG CAAAATCAGA
2201 GCGGGTCTTC CAATCTCTCC AGTGGATCTC AGCTATCTTG CTCCTAAAAA
2251 CCCAGGAACC GGTCCTGCTT TCACCATAAT CAATGGTACC CTAAAATACT
2301 TTGAGACCAG ATACATCAGA GTCGATATTG CTGCTCCAAT CCTCTCAAGA
2351 ATGGTCGGAA TGATCAGTGG AACTACCACA GAAAGGGAAC TGTGGGATGA
2401 CTGGGCACCA TATGAAGACG TGGAAATTGG ACCCAATGGA GTTCTGAGGA
2451 CCAGTTCAGG ATATAAGTTT CCTTTATACA TGATTGGACA TGGTATGTTG
2501 GACTCCGATC TTCATCTTAG CTCAAAGGCT CAGGTGTTCG AACATCCTCA
2551 CATTCAAGAC GCTGCTTCGC AACTTCCTGA TGATGAGAGT TTATTTTTTG
2601 GTGATACTGG GCTATCCAAA AATCCAATCG AGCTTGTAGA AGGTTGGTTC
2651 AGTAGTTGGA AAAGCTCTAT TGCCTCTTTT TTCTTTATCA TAGGGTTAAT
2701 CATTGGACTA TTCTTGGTTC TCCGAGTTGG TATCCATCTT TGCATTAAAT
2751 TAAAGCACAC CAAGAAAAGA CAGATTTATA CAGACATAGA GATGAACCGA

FIG.23B

```
2801  CTTGGAAAGT AACTCAAATC CTGCACAACA GATTCTTCAT GTTTGGACCA
2851  AATCAACTTG TGATACCATG CTCAAAGAGG CCTCAATTAT ATTTGAGTTT
2901  TTAATTTTTA TGAAAAAAAA AAAAAAAAAC GGAATTCCTC GAGGGATCCA
2951  GACATGATAA GATACATTGA TGAGTTTGGA CAAACCACAA CTAGAATGCA
3001  GTGAAAAAAA TGCTTTATTT GTGAAATTTG TGATGCTATT GCTTTATTTG
3051  TAACCATTAT AAGCTGCAAT AAACAAGTTA ACAACAACAA TTGCATTCAT
3101  TTTATGTTTC AGGTTCAGGG GGAGGTGTGG GAGGTTTTTT AAAGCAAGTA
3151  AAACCTCTAC AAATGTGGTA TGGCTGATTA TGATCTCTAG TCAAGGCACT
3201  ATACATCAAA TATTCCTTAT TAACCCCTTT ACAAATTAAA AAGCTAAAGG
3251  TACACAATTT TTGAGCATAG TTATTAATAG CAGACACTCT ATGCCTGTGT
3301  GGAGTAAGAA AAAACAGTAT GTTATGATTA TAACTGTTAT GCCTACTTAT
3351  AAAGGTTACA GAATATTTTT CCATAATTTT CTTGTATAGC AGTGCAGCTT
3401  TTTCCTTTGT GGTGTAAATA GCAAAGCAAG CAAGAGTTCT ATTACTAAAC
3451  ACAGCATGAC TCAAAAAACT TAGCAATTCT GAAGGAAAGT CCTTGGGGTC
3501  TTCTACCTTT CTCTTCTTTT TTGGAGGAGT AGAATGTTGA GAGTCAGCAG
3551  TAGCCTCATC ATCACTAGAT GGCATTTCTT CTGAGCAAAA CAGGTTTTCC
3601  TCATTAAAGG CATTCCACCA CTGCTCCCAT TCATCAGTTC CATAGGTTGG
3651  AATCTAAAAT ACACAAACAA TTAGAATCAG TAGTTTAACA CATTATACAC
3701  TTAAAAATTT TATATTTACC TTAGAGCTTT AAATCTCTGT AGGTAGTTTG
3751  TCCAATTATG TCACACCACA GAAGTAAGGT TCTAGAGATC CGCGGCCGC
3801  AAGATCTGGG GGATCCCCCC TGCCCGGTTA TTATTATTTT TGACACCAGA
3851  CCAACTGGTA ATGGTAGCGA CCGGCGCTCA GCTGGAATTC CGCCGATACT
3901  GACGGGCTCC AGGAGTCGTC GCCACCAATC CCCATATGGA AACCGTCGAT
3951  ATTCAGCCAT GTGCCTTCTT CCGCGTGCAG CAGATGGCGA TGGCTGGTTT
4001  CCATCAGTTG CTGTTGACTG TAGCGGCTGA TGTTGAACTG GAAGTCGCCG
4051  CGCCACTGGT GTGGGCCATA ATTCAATTCG CGCGTCCCGC AGCGCAGACC
4101  GTTTTCGCTC GGGAAGACGT ACGGGGTATA CATGTCTGAC AATGGCAGAT
4151  CCCAGCGGTC AAAACAGGCG GCAGTAAGGC GGTCGGGATA GTTTTCTTGC
```

FIG.23C

4201 GGCCCTAATC CGAGCCAGTT TACCCGCTCT GCTACCTGCG CCAGCTGGCA
4251 GTTCAGGCCA ATCCGCGCCG GATGCGGTGT ATCGCTCGCC ACTTCAACAT
4301 CAACGGTAAT CGCCATTTGA CCACTACCAT CAATCCGGTA GGTTTTCCGG
4351 CTGATAAATA AGGTTTTCCC CTGATGCTGC CACGCGTGAG CGGTCGTAAT
4401 CAGCACCGCA TCAGCAAGTG TATCTGCCGT GCACTGCAAC AACGCTGCTT
4451 CGGCCTGGTA ATGGCCCGCC GCCTTCCAGC GTTCGACCCA GGCGTTAGGG
4501 TCAATGCGGG TCGCTTCACT TACGCCAATG TCGTTATCCA GCGGTGCACG
4551 GGTGAACTGA TCGCGCAGCG GCGTCAGCAG TTGTTTTTTA TCGCCAATCC
4601 ACATCTGTGA AAGAAAGCCT GACTGGCGGT TAAATTGCCA ACGCTTATTA
4651 CCCAGCTCGA TGCAAAAATC CATTTCGCTG GTGGTCAGAT GCGGGATGGC
4701 GTGGGACGCG GCGGGGAGCG TCACACTGAG GTTTTCCGCC AGACGCCACT
4751 GCTGCCAGGC GCTGATGTGC CCGGCTTCTG ACCATGCGGT CGCGTTCGGT
4801 TGCACTACGC GTACTGTGAG CCAGAGTTGC CCGGCGCTCT CCGGCTGCGG
4851 TAGTTCAGGC AGTTCAATCA ACTGTTTACC TTGTGGAGCG ACATCCAGAG
4901 GCACTTCACC GCTTGCCAGC GGCTTACCAT CCAGCGCCAC CATCCAGTGC
4951 AGGAGCTCGT TATCGCTATG ACGGAACAGG TATTCGCTGG TCACTTCGAT
5001 GGTTTGCCCG GATAAACGGA ACTGGAAAAA CTGCTGCTGG TGTTTTGCTT
5051 CCGTCAGCGC TGGATGCGGC GTGCGGTCGG CAAAGACCAG ACCGTTCATA
5101 CAGAACTGGC GATCGTTCGG CGTATCGCCA AAATCACCGC CGTAAGCCGA
5151 CCACGGGTTG CCGTTTTCAT CATATTTAAT CAGCGACTGA TCCACCCAGT
5201 CCCAGACGAA GCCGCCCTGT AAACGGGGAT ACTGACGAAA CGCCTGCCAG
5251 TATTTAGCGA AACCGCCAAG ACTGTTACCC ATCGCGTGGG CGTATTCGCA
5301 AAGGATCAGC GGGCGCGTCT CTCCAGGTAG CGAAAGCCAT TTTTTGATGG
5351 ACCATTTCGG CACAGCCGGG AAGGGCTGGT CTTCATCCAC GCGCGCGTAC
5401 ATCGGGCAAA TAATATCGGT GGCCGTGGTG TCGGCTCCGC CGCCTTCATA
5451 CTGCACCGGG CGGGAAGGAT CGACAGATTT GATCCAGCGA TACAGCGCGT
5501 CGTGATTAGC GCCGTGGCCT GATTCATTCC CCAGCGACCA GATGATCACA
5551 CTCGGGTGAT TACGATCGCG CTGCACCATT CGCGTTACGC GTTCGCTCAT
5601 CGCCGGTAGC CAGCGCGGAT CATCGGTCAG ACGATTCATT GGCACCATGC

FIG.23D

```
5651 CGTGGGTTTC AATATTGGCT TCATCCACCA CATACAGGCC GTAGCGGTCG
5701 CACAGCGTGT ACCACAGCGG ATGGTTCGGA TAATGCGAAC AGCGCACGGC
5751 GTTAAAGTTG TTCTGCTTCA TCAGCAGGAT ATCCTGCACC ATCGTCTGCT
5801 CATCCATGAC CTGACCATGC AGAGGATGAT GCTCGTGACG GTTAACGCCT
5851 CGAATCAGCA ACGGCTTGCC GTTCAGCAGC AGCAGACCAT TTTCAATCCG
5901 CACCTCGCGG AAACCGACAT CGCAGGCTTC TGCTTCAATC AGCGTGCCGT
5951 CGGCGGTGTG CAGTTCAACC ACCGCACGAT AGAGATTCGG GATTTCGGCG
6001 CTCCACAGTT TCGGGTTTTC GACGTTCAGA CGTAGTGTGA CGCGATCGGC
6051 ATAACCACCA CGCTCATCGA TAATTTCACC GCCGAAAGGC GCGGTGCCGC
6101 TGGCGACCTG CGTTTCACCC TGCCATAAAG AAACTGTTAC CCGTAGGTAG
6151 TCACGCAACT CGCCGCACAT CTGAACTTCA GCCTCCAGTA CAGCGCGGCT
6201 GAAATCATCA TTAAAGCGAG TGGCAACATG GAAATCGCTG ATTTGTGTAG
6251 TCGGTTTATG CAGCAACGAG ACGTCACGGA AAATGCCGCT CATCCGCCAC
6301 ATATCCTGAT CTTCCAGATA ACTGCCGTCA CTCCAACGCA GCACCATCAC
6351 CGCGAGGCGG TTTTCTCCGG CGCGTAAAAA TGCGCTCAGG TCAAATTCAG
6401 ACGGCAAACG ACTGTCCTGG CCGTAACCGA CCCAGCGCCC GTTGCACCAC
6451 AGATGAAACG CCGAGTTAAC GCCATCAAAA ATAATTCGCG TCTGGCCTTC
6501 CTGTAGCCAG CTTTCATCAA CATTAAATGT GAGCGAGTAA CAACCCGTCG
6551 GATTCTCCGT GGGAACAAAC GGCGGATTGA CCGTAATGGG ATAGGTTACG
6601 TTGGTGTAGA TGGGCGCATC GTAACCGTGC ATCTGCCAGT TTGAGGGGAC
6651 GACGACAGTA TCGGCCTCAG GAAGATCGCA CTCCAGCCAG CTTTCCGGCA
6701 CCGCTTCTGG TGCCGGAAAC CAGGCAAAGC GCCATTCGCC ATTCAGGCTG
6751 CGCAACTGTT GGGAAGGGCG ATCGGTGCGG GCCTCTTCGC TATTACGCCA
6801 GCTGGCGAAA GGGGGATGTG CTGCAAGGCG ATTAAGTTGG GTAACGCCAG
6851 GGTTTTCCCA GTCACGACGT TGTAAAACGA CGGGATCCGC CATGTCACAG
6901 ATCTTGCGGC CGCGGGAATT CGAGCTCGGT ACCAGATCCT CTAGAGTCAG
6951 GCTGGATCGG TCCCGGTGTC TTCTATGGAG GTCAAAACAG CGTGGATGGC
7001 GTCTCCAGGC GATCTgacgg ttcactaaac gagctctgct tatatagacc
```

FIG.23E

```
7051  tcccaccgta caccnctacc gcccatttgc gtcaaygggg cggagttgtt
7101  acgacatttt ggaaagtccc gttgattttg gtgccaaaac aaactcccat
7151  tgacgtcaat ggggtggaga cttggaaatc cccgtgagtc aaaccgctat
7201  ccacccccat tgatgtactg ccaaaaccgc atcaccatgg taatagcgat
7251  gactaatacg tagatgtaca gccaagtagg aaagtcccat aaggtcatgt
7301  actgggcata atgccaggcg ggccatttac cgtcattgac gtcaataccg
7351  ggcgtacttg gcatatgata cacttgatgt actgccaagt gggcagttta
7401  ccgtaaatac tccacccatt gacgtcaatg gaaagtccct attggcgtta
7451  ctatgggaac atacgtcatt attgacgtca atgcccGGGG GTCGTTGGGC
7501  GGTCAGCCAG GCGGGCCATT TACCGTAAGT TATGTAACGC GGAACTCCAT
7551  ATATGGGCTA TGAACTAATG ACCCCGTAAT TGATTACTAT TAATAACTAG
7601  TCAATAATCA ATGTCAACAT GGCGGTAATG TTGGACATGA GCCAATATAA
7651  ATGTACATAT TATGATATGG ATACAACGTA TGCAATGGGC CAAGCTTATC
7701  GATACCGTCG ACCTCGAGGC CTGCAGGGCG GCCGGCCGCT TAATTAATTG
7751  ATCCGGGTTA TTAGTACATT TATTAAGCGC TAGATTCTGT GCGTTGTTGA
7801  TTTACAGACA ATTGTTGTAC GTATTTTAAT AATTCATTAA ATTTATAATC
7851  TTTAGGGTGG TATGTTAGAG CGAAAATCAA ATGATTTTCA GCGTCTTTAT
7901  ATCTGAATTT AAATATTAAA TCCTCAATAG ATTTGTAAAA TAGGTTTCGA
7951  TTAGTTTCAA ACAAGGGTTG TTTTTCCGAA CCGATGGCTG GACTATCTAA
8001  TGGATTTTCG CTCAACGCCA CAAAACTTGC CAAATCTTGT AGCAGCAATC
8051  TAGCTTTGTC GATATTCGTT TGTGTTTTGT TTTGTAATAA AGGTTCGACG
8101  TCGTTCAAAA TATTATGCGC TTTTGTATTT CTTTCATCAC TGTCGTTAGT
8151  GTACAATTGA CTCGACGTAA ACACGTTAAA TAAAGCTTGG ACATATTTAA
8201  CATCGGGCGT GTTAGCTTTA TTAGGCCGAT TATCGTCGTC GTCCCAACCC
8251  TCGTCGTTAG AAGTTGCTTC CGAAGACGAT TTTGCCATAG CCACACGACG
8301  CCTATTAATT GTGTCGGCTA ACACGTCCGC GATCAAATTT GTAGTTGAGC
8351  TTTTTGGAAT TATTTCTGAT TGCGGGCGTT TTTGGGCGGG TTTCAATCTA
8401  ACTGTGCCCG ATTTTAATTC AGACAACACG TTAGAAAGCG ATGGTGCAGG
8451  CGGTGGTAAC ATTTCAGACG GCAAATCTAC TAATGGCGGC GGTGGTGGAG
```

FIG. 23F

```
8501  CTGATGATAA ATCTACCATC GGTGGAGGCG CAGGCGGGGC TGGCGGCGGA
8551  GGCGGAGGCG GAGGTGGTGG CGGTGATGCA GACGGCGGTT TAGGCTCAAA
8601  TGTCTCTTTA GGCAACACAG TCGGCACCTC AACTATTGTA CTGGTTTCGG
8651  GCGCCGTTTT TGGTTTGACC GGTCTGAGAC GAGTGCGATT TTTTTCGTTT
8701  CTAATAGCTT CCAACAATTG TTGTCTGTCG TCTAAAGGTG CAGCGGGTTG
8751  AGGTTCCGTC GGCATTGGTG GAGCGGGCGG CAATTCAGAC ATCGATGGTG
8801  GTGGTGGTGG TGGAGGCGCT GGAATGTTAG GCACGGGAGA AGGTGGTGGC
8851  GGCGGTGCCG CCGGTATAAT TTGTTCTGGT TTAGTTTGTT CGCGCACGAT
8901  TGTGGGCACC GGCGCAGGCG CCGCTGGCTG CACAACGGAA GGTCGTCTGC
8951  TTCGAGGCAG CGCTTGGGGT GGTGGCAATT CAATATTATA ATTGGAATAC
9001  AAATCGTAAA AATCTGCTAT AAGCATTGTA ATTTCGCTAT CGTTTACCGT
9051  GCCGATATTT AACAACCGCT CAATGTAAGC AATTGTATTG TAAAGAGATT
9101  GTCTCAAGCT CGGATCGATC CCGCACGCCG ATAACAAGCC TTTTCATTTT
9151  TACTACAGCA TTGTAGTGGC GAGACACTTC GCTGTCGTCG CCTGATGCGG
9201  TATTTTCTCC TTACGCATCT GTGCGGTATT TCACACCGCA TACGTCAAAG
9251  CAACCATAGT ACGCGCCCTG TAGCGGCGCA TTAAGCGCGG CGGGTGTGGT
9301  GGTTACGCGC AGCGTGACCG CTACACTTGC CAGCGCCCTA GCGCCCGCTC
9351  CTTTCGCTTT CTTCCCTTCC TTTCTCGCCA CGTTCGCCGG CTTTCCCCGT
9401  CAAGCTCTAA ATCGGGGGCT CCCTTTAGGG TTCCGATTTA GTGCTTTACG
9451  GCACCTCGAC CCCAAAAAAC TTGATTTGGG TGATGGTTCA CGTAGTGGGC
9501  CATCGCCCTG ATAGACGGTT TTTCGCCCTT TGACGTTGGA GTCCACGTTC
9551  TTTAATAGTG GACTCTTGTT CCAAACTGGA ACAACACTCA ACCCTATCTC
9601  GGGCTATTCT TTTGATTTAT AAGGGATTTT GCCGATTTCG GCCTATTGGT
9651  TAAAAAATGA GCTGATTTAA CAAAAATTTA ACGCGAATTT TAACAAAATA
9701  TTAACGTTTA CAATTTTATG GTGCACTCTC AGTACAATCT GCTCTGATGC
9751  CGCATAGTTA AGCCAGCCCC GACACCCGCC AACACCCGCT GACGCGCCCT
9801  GACGGGCTTG TCTGCTCCCG GCATCCGCTT ACAGACAAGC TGTGACCGTC
9851  TCCGGGAGCT GCATGTGTCA GAGGTTTTCA CCGTCATCAC CGAAACGCGC
```

FIG.23G

```
 9901  GAGACGAAAG GGCCTCGTGA TACGCCTATT TTTATAGGTT AATGTCATGA
 9951  TAATAATGGT TTCTTAGACG TCAGGTGGCA CTTTTCGGGG AAATGTGCGC
10001  GGAACCCCTA TTTGTTTATT TTTCTAAATA CATTCAAATA TGTATCCGCT
10051  CATGAGACAA TAACCCTGAT AAATGCTTCA ATAATATTGA AAAAGGAAGA
10101  GTATGAGTAT TCAACATTTC CGTGTCGCCC TTATTCCCTT TTTTGCGGCA
10151  TTTTGCCTTC CTGTTTTTGC TCACCCAGAA ACGCTGGTGA AAGTAAAAGA
10201  TGCTGAAGAT CAGTTGGGTG CACGAGTGGG TTACATCGAA CTGGATCTCA
10251  ACAGCGGTAA GATCCTTGAG AGTTTTCGCC CCGAAGAACG TTTTCCAATG
10301  ATGAGCACTT TTAAAGTTCT GCTATGTGGC GCGGTATTAT CCCGTATTGA
10351  CGCCGGGCAA GAGCAACTCG GTCGCCGCAT ACACTATTCT CAGAATGACT
10401  TGGTTGAGTA CTCACCAGTC ACAGAAAAGC ATCTTACGGA TGGCATGACA
10451  GTAAGAGAAT TATGCAGTGC TGCCATAACC ATGAGTGATA ACACTGCGGC
10501  CAACTTACTT CTGACAACGA TCGGAGGACC GAAGGAGCTA ACCGCTTTTT
10551  TGCACAACAT GGGGGATCAT GTAACTCGCC TTGATCGTTG GGAACCGGAG
10601  CTGAATGAAG CCATACCAAA CGACGAGCGT GACACCACGA TGCCTGTAGC
10651  AATGGCAACA ACGTTGCGCA AACTATTAAC TGGCGAACTA CTTACTCTAG
10701  CTTCCCGGCA ACAATTAATA GACTGGATGG AGGCGGATAA AGTTGCAGGA
10751  CCACTTCTGC GCTCGGCCCT TCCGGCTGGC TGGTTTATTG CTGATAAATC
10801  TGGAGCCGGT GAGCGTGGGT CTCGCGGTAT CATTGCAGCA CTGGGGCCAG
10851  ATGGTAAGCC CTCCCGTATC GTAGTTATCT ACACGACGGG GAGTCAGGCA
10901  ACTATGGATG AACGAAATAG ACAGATCGCT GAGATAGGTG CCTCACTGAT
10951  TAAGCATTGG TAACTGTCAG ACCAAGTTTA CTCATATATA CTTTAGATTG
11001  ATTTAAAACT TCATTTTTAA TTTAAAAGGA TCTAGGTGAA GATCCTTTTT
11051  GATAATCTCA TGACCAAAAT CCCTTAACGT GAGTTTTCGT TCCACTGAGC
11101  GTCAGACCCC GTAGAAAAGA TCAAAGGATC TTCTTGAGAT CCTTTTTTTC
11151  TGCGCGTAAT CTGCTGCTTG CAAACAAAAA AACCACCGCT ACCAGCGGTG
11201  GTTTGTTTGC CGGATCAAGA GCTACCAACT CTTTTTCCGA AGGTAACTGG
11251  CTTCAGCAGA GCGCAGATAC CAAATACTGT CCTTCTAGTG TAGCCGTAGT
11301  TAGGCCACCA CTTCAAGAAC TCTGTAGCAC CGCCTACATA CCTCGCTCTG
```

FIG.23H

```
11351  CTAATCCTGT  TACCAGTGGC  TGCTGCCAGT  GGCGATAAGT  CGTGTCTTAC
11401  CGGGTTGGAC  TCAAGACGAT  AGTTACCGGA  TAAGGCGCAG  CGGTCGGGCT
11451  GAACGGGGGG  TTCGTGCACA  CAGCCCAGCT  TGGAGCGAAC  GACCTACACC
11501  GAACTGAGAT  ACCTACAGCG  TGAGCTATGA  GAAAGCGCCA  CGCTTCCCGA
11551  AGGGAGAAAG  GCGGACAGGT  ATCCGGTAAG  CGGCAGGGTC  GGAACAGGAG
11601  AGCGCACGAG  GGAGCTTCCA  GGGGGAAACG  CCTGGTATCT  TTATAGTCCT
11651  GTCGGGTTTC  GCCACCTCTG  ACTTGAGCGT  CGATTTTTGT  GATGCTCGTC
11701  AGGGGGGCGG  AGCCTATGGA  AAAACGCCAG  CAACGCGGCC  TTTTTACGGT
11751  TCCTGGCCTT  TTGCTGGCCT  TTTGCTCACA  TGTTCTTTCC  TGCGTTATCC
11801  CCTGATTCTG  TGGATAACCG  TATTACCGCC  TTTGAGTGAG  CTGATACCGC
11851  TCGCCGCAGC  CGAACGACCG  AGCGCAGCGA  GTCAGTGAGC  GAGGAAGCGG
11901  AAGAGCGCCC  AATACGCAAA  CCGCCTCTCC  CCGCGCGTTG  GCCGATTCAT
11951  TAATGCAG    (SEQ ID NO:7)
```

FIG. 23I

EXPRESSION OF AN EXOGENOUS GENE IN A MAMMALIAN CELL BY USE OF A NON-MAMMALIAN DNA VIRUS HAVING AN ALTERED COAT PROTEIN

CROSS-REFERENCE TO RELATED APPLICATIONS

This application is a divisional of U.S. Ser. No. 08/927,317, filed Sep. 11, 1997, which claims priority under 35 U.S.C. §119 from U.S. Ser. No. 60/026,297, filed Sep. 11, 1996.

BACKGROUND OF THE INVENTION

This invention relates to the use of a non-mammalian DNA virus to express an exogenous gene in a mammalian cell.

Current methods for expressing an exogenous gene in a mammalian cell include the use of mammalian viral vectors, such as those that are derived from retroviruses, adenoviruses, herpes viruses, vaccinia viruses, polio viruses, or adeno-associated viruses. Other methods of expressing an exogenous gene in a mammalian cell include direct injection of DNA, the use of ligand-DNA conjugates, the use of adenovirus-ligand-DNA conjugates, calcium phosphate precipitation, and methods that utilize a liposome- or polycation-DNA complex. In some cases, the liposome- or polycation-DNA complex is able to target the exogenous gene to a specific type of tissue, such as liver tissue.

Typically, viruses that are used to express desired genes are constructed by removing unwanted characteristics from a virus that is known to infect, and replicate in, a mammalian cell. For example, the genes encoding viral structural proteins and proteins involved in viral replication often are removed to create a defective virus, and a therapeutic gene is then added. This principle has been used to create gene therapy vectors from many types of animal viruses such as retroviruses, adenoviruses, and herpes viruses. This method has also been applied to Sindbis virus, an RNA virus that normally infects mosquitoes but which can replicate in humans, causing a rash and an arthritis syndrome.

Non-mammalian viruses have been used to express exogenous genes in non-mammalian cells. For example, viruses of the family Baculoviridae (commonly referred to as baculoviruses) have been used to express exogenous genes in insect cells. One of the most studied baculoviruses is Autographa genes in insect cells. One of the most studied baculoviruses is *Autographa californica* multiple nuclear polyhedrosis virus (AcMNPV). Although some species of baculoviruses that infect crustacea have been described (Blissard, et al., 1990, Ann. Rev. Entomology 35:127), the normal host range of the baculovirus AcMNPV is limited to the order lepidoptera. Baculoviruses have been reported to enter mammalian cells (Volkman and Goldsmith, 1983, Appl. and Environ. Microbiol. 45:1085–1093; Carbonell and Miller, 1987, Appl. and Environ. Microbiol. 53:1412–1417; Brusca et al., 1986, Intervirology 26:207–222; and Tjia et al., 1983, Virology 125:107–117). Although an early report of baculovirus-mediated gene expression in mammalian cells appeared, the authors later attributed the apparent reporter gene activity to the reporter gene product being carried into the cell after a prolonged incubation of the cell with the virus (Carbonell et al., 1985, J. Virol. 56:153–160; and Carbonell and Miller, 1987, Appl. and Environ. Microbiol. 53:1412–1417). These authors reported that, when the exogenous gene gains access to the cell as part of the baculovirus genome, the exogenous gene is not expressed de novo. Subsequent studies have demonstrated baculovirus-mediated gene expression in mammalian cells (Boyce and Bucher, 1996, Proc. Natl. Acad. Sci. 93:2348–2352). In addition to the Baculoviridae, other families of viruses naturally multiply only in invertebrates; some of these viruses are listed in Table 1.

Gene therapy methods are currently being investigated for their usefulness in treating a variety of disorders. Most gene therapy methods involve supplying an exogenous gene to overcome a deficiency in the expression of a gene in the patient. Other gene therapy methods are designed to counteract the effects of a disease. Still other gene therapy methods involve supplying an antisense nucleic acid (e.g., RNA) to inhibit expression of a gene of the host cell (e.g., an oncogene) or expression of a gene from a pathogen (e.g., a virus).

Certain gene therapy methods are being examined for their ability to correct inborn errors of the urea cycle, for example (see, e.g., Wilson et al., 1992, J. Biol. Chem. 267: 11483–11489). The urea cycle is the predominant metabolic pathway by which nitrogen wastes are eliminated from the body. The steps of the urea cycle are primarily limited to the liver, with the first two steps occurring within hepatic mitochondria. In the first step, carbamoyl phosphate is synthesized in a reaction that is catalyzed by carbamoyl phosphate synthetase I (CPS-I). In the second step, citrulline in formed in a reaction catalyzed by ornithine transcarbamylase (OTC). Citrulline then is transported to the cytoplasm and condensed with aspartate into arginosuccinate by arginosuccinate synthetase (AS). In the next step, arginosuccinate lyase (ASL) cleaves arginosuccinate to produce arginine and fumarate. In the last step of the cycle, arginase converts arginine into ornithine and urea A deficiency in any of the five enzymes involved in the urea cycle has significant pathological effects, such as lethargy, poor feeding, mental retardation, coma, or death within the neonatal period (see, e.g., Emery et al., 1990, In: Principles and Practice of Medical Genetics, Churchill Livingstone, New York). OTC deficiency usually manifests as a lethal hyperammonemic coma within the neonatal period. A deficiency in AS results in citrullinemia which is characterized by high levels of citrulline in the blood. The absence of ASL results in arginosuccinic aciduria (ASA), which results in a variety of conditions including severe neonatal hyperammonemia and mild mental retardation. An absence of arginase results in hyperarginemia which can manifest as progressive spasticity and mental retardation during early childhood. Other currently used therapies for hepatic disorders include dietary restrictions; liver transplantation; and administration of arginine freebase, sodium benzoate, and/or sodium phenylacetate.

SUMMARY OF THE INVENTION

It has been discovered that a non-mammalian DNA virus carrying an exogenous gene expression construct and having an "altered" coat protein can be used to increase the efficiency with which the non-mammalian DNA virus expresses an exogenous gene in the mammalian cell. For example, expression of vesicular stomatitis virus glycoprotein G (VSV-G) as an altered coat protein on the surface of a virus particle of a baculovirus enhances the ability of the baculovirus to express an exogenous gene (e.g., a therapeutic gene) in a mammalian cell. While not being obligated to know or disclose the manner in which the invention works, nor being bound by any theory, it is postulated that the enhancement of gene expression is due to an increased ability of a virus particle to gain entry into the cytosol of the mammalian cell.

Accordingly, in one aspect, the invention features a method of expressing an exogenous gene in a mammalian cell(s), involving (i) introducing into the cell a non-mammalian DNA virus having an altered coat protein, the genome of which virus carries the exogenous gene under the control of a promoter that induces expression of the exogenous gene in the cell, and (ii) maintaining the cell under conditions such that the exogenous gene is expressed.

In a second aspect, the invention features a method of treating a gene deficiency disorder in a mammal (e.g., a human or a mouse), involving introducing into a cell (in vivo or ex vivo) a therapeutically effective amount of a non-mammalian DNA virus having an altered coat protein, the genome of which virus carries an exogenous gene, and maintaining the cell under conditions such that the exogenous gene is expressed in the mammal.

The invention further features a method for treating a tumor in a mammal, involving introducing into a cancerous cell of the mammal (e.g., a cancerous hepatocyte) a non-mammalian DNA virus (e.g., a baculovirus) having an altered coat protein, the genome of which virus expresses a cancer-therapeutic gene (encoding, e.g., a tumor necrosis factor, thymidine kinase, diphtheria toxin chimera, or cytosine deaminase). The exogenous gene can be expressed in a variety of cells, e.g., hepatocytes; cells of the central nervous system, including neural cells such as neurons from brain, spinal cord, or peripheral nerve; adrenal medullary cells; glial cells; skin cells; spleen cells; muscle cells; kidney cells; and bladder cells. Thus, the invention can be used to treat various cancerous or non-cancerous tumors, including carcinomas (e.g., hepatocellular carcinoma), sarcomas, gliomas, and neuromas. Included within the invention are methods for treating lung, breast, and prostate cancers. Either in vivo or in vitro methods can be used to introduce the virus into the cell in this aspect of the invention. Preferably, the exogenous gene is operably linked to a promoter that is active in cancerous cells, but not in other cells, of the mammal. For example, the α-fetoprotein promoter is active in cells of hepatocellular carcinomas and in fetal tissue but it is otherwise not active in mature tissues. Accordingly, the use of such a promoter is preferred for expressing a cancer-therapeutic gene for treating hepatocellular carcinomas.

The invention also features a method for treating a neurological disorder (e.g., Parkinson's Disease, Alzheimer's Disease, or disorders resulting from injuries to the central nervous system) in a mammal. The method involves (a) introducing into a cell a therapeutically effective amount of a non-mammalian DNA virus (e.g., a baculovirus) having an altered coat protein, the genome of which virus includes an exogenous gene encoding a therapeutic protein, and (b) maintaining the cell under conditions such that the exogenous gene is expressed in the mammal. Particularly useful exogenous genes include those that encode therapeutic proteins such as nerve growth factor, hypoxanthine guanine phosphoribosyl transferase (HGPRT), tyrosine hydroxylase, dopadecarboxylase, brain-derived neurotrophic factor, basic fibroblast growth factor, sonic hedgehog protein, glial derived neurotrophic factor (GDNF) and RETLI (also known as GDNFRα, GFR-1, and TRN1). Both neuronal and non-neuronal cells (e.g., fibroblasts, myoblasts, and kidney cells) are useful in this aspect of the invention. Such cells can be autologous or heterologous to the treated mammal. Preferably, the cell is autologous to the mammal, as such cells obviate concerns about graft rejection. Preferably, the cell is a primary cell, such as a primary neuronal cell or a primary myoblast.

In each aspect of the invention, the non-mammalian DNA virus is preferably an "invertebrate virus" (i.e., a virus that infects, and replicates in, an invertebrate). For example, the DNA viruses listed in Table 1 can be engineered to have an altered coat protein(s) and used in the invention. Preferably, the invertebrate DNA virus is a baculovirus, e.g., a nuclear polyhedrosis virus, such as an *Autographa californica* multiple nuclear polyhedrosis virus. If desired, the nuclear polyhedrosis virus may be engineered such that it lacks a functional polyhedrin gene. Either or both the occluded form and budded form of virus (e.g., baculovirus) can be used. Another preferred virus is *Bombyx mori* Nuclear Polyhedrosis Virus (BmNPV).

TABLE 1

NON-MAMMALIAN DNA VIRUSES THAT CAN BE USED IN THE INVENTION.[1]

I. FAMILY: BACULOVIRUSES BACULOVIRIDAE
SUBFAMILY:
OCCLUDED BACULOVIRUSES EUBACULOVIRINAE
Genus:
Nuclear polyhedrosis virus (NPV)
Subgenus:
Multiple Nucleocapsid Viruses (MNPV)
Preferred Species:
Autographa californica nuclear polyhedrosis virus (AcMNPV)
Other Members:

*Choristoneura fumiferana* MNPV (CfMNPV)
*Mamestra brassicae* MNPV (MbMNPV)
*Orgyia pseudotsugata* MNPV (OpMNPV)
and approximately 400-500 species
isolated from seven insect orders and Crustacea.
Subgenus:
Single Nucleocapsid Viruses (SNPV)
Preferred Species:
*Bombyx mori* S Nuclear Polyhedrosis Virus (BmNPV)
Other Members:

*Heliothis zea* SNPV (HzSnpv)
*Trichoplusia ni* SNPV (TnSnpv)
and similar viruses isolated from seven insect
orders and Crustacea.
Genus:
Granulosis virus (GV)
Preferred Species:
*Plodia interpunctella* granulosis virus (PiGV)
Other Members:

*Trichoplusia ni* granulosis virus (TnGV)
*Pieris brassicae* granulosis virus (PbGV)
*Artogeia rapae* granulosis virus (ArGV)
*Cydia pomonella* granulosis virus (CpGV)
and similar viruses from about 50 species in the Lepidoptera
SUBFAMILY:
NON-OCCLUDED BACULOVIRUSES NUDIBACULOVIRINAE
Genus:
Non-occluded baculoviruses (NOB)
Preferred Species:
*Heliothis zea* NOB (HzNOB)
Other Members:

*Oryctes rhinoceros* virus
Additional viruses have been observed in a fungus
(*Strongwellsea magna*), a spider, the European crab
(*Carcinus maenas*), and the blue crab (*Callinectes sapidus*).
II. FAMILY: ICOSAHEDRAL CYTOPLASMIC DEOXYRIBO-VIRUSES IRIDOVIRIDAE
Genus:
Small iridescent Iridovirus insect virus group
Preferred Species:
Chilo iridescent virus TABLE 1-continued

NON-MAMMALIAN DNA VIRUSES THAT CAN BE USED IN THE INVENTION.[1]

Other Members:

| | |
|---|---|
| Insect iridescent virus 1 | Insect iridescent virus 2 |
| Insect iridescent virus 6 | Insect iridescent virus 9 |
| Insect iridescent virus 10 | Insect iridescent virus 16 |
| Insect iridescent virus 17 | Insect iridescent virus 18 |
| Insect iridescent virus 19 | Insect iridescent virus 20 |
| Insect iridescent virus 21 | Insect iridescent virus 22 |
| Insect iridescent virus 23 | Insect iridescent virus 24 |
| Insect iridescent virus 25 | Insect iridescent virus 26 |
| Insect iridescent virus 27 | Insect iridescent virus 28 |
| Insect iridescent virus 29 | Insect iridescent virus 30 |
| Insect iridescent virus 31 | Insect iridescent virus 32 |

Genus:
Large iridescent Chloriridovirus insect virus group
Preferred Species:

Mosquito iridescent virus (iridescent virus - type 3, regular strain)
Other Members:

| | |
|---|---|
| Insect iridescent virus 3 | Insect iridescent virus 4 |
| Insect iridescent virus 5 | Insect iridescent virus 7 |
| Insect iridescent virus 8 | Insect iridescent virus 11 |
| Insect iridescent virus 12 | Insect iridescent virus 13 |
| Insect iridescent virus 14 | Insect iridescent virus 15 |

Putative member:
Chironomus plumosus iridescent
Genus:
Frog virus group Ranavirus
Preferred Species:
Frog virus 3 (FV3)
Other Members:

| | | | |
|---|---|---|---|
| Frog virus 1 | Frog virus 2 | Frog virus 5 | |
| Frog virus 6 | Frog virus 7 | Frog virus 8 | |
| Frog virus 9 | Frog virus 10 | Frog virus 11 | |
| Frog virus 12 | Frog virus 13 | Frog virus 14 | |
| Frog virus 15 | Frog virus 16 | Frog virus 17 | |
| Frog virus 18 | Frog virus 19 | Frog virus 20 | |
| Frog virus 21 | Frog virus 22 | Frog virus 23 | |
| Frog virus 24 | L2 | L4 | L5 |
| LT 1 | LT 2 | LT 3 | LT 4 |
| T 21 | T 6 | T 7 | T 8 |
| T 9 | T 10 | T 11 | T 12 |
| T 13 | T 14 | T 15 | T 16 |
| T 17 | T 18 | T 19 | T 20 |

Tadpole edema virus from newts
Tadpole edema virus from *Rana catesbriana*
Tadpole edema virus from Xenopus
Genus:
Lymphocystis disease virus group
Lymphocystisvirus
Preferred Species:
Flounder isolate (LCDV-1)
Other Members:
Lymphocystis disease virus dab isolate (LCDV-2)
Putative member:
*Octopus vulgaris* disease virus
Genus
Goldfish virus group
Preferred Species:
Goldfish virus 1 (GFV-1)
Other Member:
Goldfish virus 2 (GF-2)
III. FAMILY: PARVOVIRIDAE
Genus
Insect parvovirus group Densovirus
Preferred Species:
Galleria densovirus
Other Members:

Junonia Densovirus
Agraulis Densovirus
Bombyx Densovirus
Aedes Densovirus

TABLE 1-continued

NON-MAMMALIAN DNA VIRUSES THAT CAN BE USED IN THE INVENTION.[1]

Putative Members:

| | |
|---|---|
| Acheta Densovirus | Simulium Densovirus |
| Diatraea Densovirus | Euxoa Densovirus |
| Leucorrhinia Densovirus | Periplanata Densovirus |
| Pieris Densovirus | Sibine Densovirus |

PC 84 (parvo-like virus from the crab Carcinus mediterraneus)
Hepatopancreatic parvo-like virus of penaeid shrimp
IV. FAMILY: POXVIRUS GROUP POXVIRIDAE
SUBFAMILY:
POXVIRUSES OF VERTEBRATES CHORDOPOXVIRINAE
Genus:
*Molluscum contagiosum* subgroup Molluscipoxvirus
Preferred Species:
*Molluscum contagiosum* virus
SUBFAMILY:
POXVIRUS OF INSECTS ENTOMOPOXVIRINAE
Putative Genus:
Entomopoxvirus A Poxvirus of Coleoptera
Preferred Species:
Poxvirus of Melolontha
Other Members:
Coleoptera:

*Anomala cuprea*
*Aphodius tasmaniae*
*Demodema boranensis*
*Dermolepida albohirtum*
*Figulus sublaevis*
*Geotrupes sylvaticus*
Putative Genus:
Entomopoxvirus B Poxvirus of Lepidoptera and Orthoptera
Preferred Species:
Poxvirus of Amsacta moorei (Lepidoptera)
Other Members:
Lepidoptera:

*Acrobasis zelleri*
*Choristoneura biennis*
*Choristoneura conflicta*
*Choristoneura diversuma*
*Chorizagrotis auxiliaris*
*Operophtera brumata*
Orthoptera:

*Arphia conspersa*
*Locusta migratoria*
*Melanoplus sanguinipes*
*Oedaleus senugaiensis*
*Schistocerca gregaria*
Putative Genus:
Entomopoxvirus C Poxvirus of Diptera
Preferred Species:
Poxvirus of Chironomus luridus (Diptera)
Other Members:
Diptera:

*Aedes aegypti*
*Camptochironomus tentans*
*Chironomus attenuatus*
*Chironomus plumosus*
*Goeldichironomus holoprasimus*
Other members of family Poxviridae Albatrosspox (Avipoxvirus)
Cotia
Embu
Marmosetpox
Marsupialpox (Australian 'quokkas')
Mule deer poxvirus (*Odocoileus hemionus*; Capripoxvirus)
Volepox (*Microtus oeconomus, Microtus pennsylvanicus*)

TABLE 1-continued

NON-MAMMALIAN DNA VIRUSES THAT CAN BE USED IN THE INVENTION.[1]

Skunk poxvirus (Mephitis; Orthopoxvirus)
V. GROUP CAULIFLOWER CAULIMOVIRUS MOSAIC VIRUS
Preferred Member:

Cauliflower mosaic virus (CaMV) (cabbage b, davis isolate)
Other Members:

| | |
|---|---|
| Blueberry red ringspot (327) | Carnation etched ring (182) |
| Dahlia mosaic (51) | Figwort mosaic |
| Horseradish latent | Mirabilis mosaic |
| Peanut chlorotic streak | Soybean chlorotic mottle (331) |
| Strawberry vein banding (219) | Thistle mottle |

Putative Members:

| | |
|---|---|
| Aquilegia necrotic mosaic | Cassava vein mosaic |
| Cestrurm virus | Petunia vein clearing |
| Plantago virus 4 | Sonchus mottle |

VI. GROUP GEMINIVIRUS
Subgroup I (i.e., Genus)
Maize streak virus
Preferred Member:
Maize streak virus (MSV) (133)
Other Members:

Chloris striate mosaic (221)
Digitaria streak
Miscanthus streak
Wheat dwarf
Putative Members:

Bajra streak
Bromus striate mosaic
Digitaria striate mosaic
Oat chlorotic stripe
Paspalum striate mosaic
Subgroup II (i.e., Genus):
Beet curly top virus
Preferred Member:
Beet curly top virus (BCTV)(210)
Other Members:

Tomato pseudo-curly top virus
Bean summer death virus
Tobacco yellow dwarf virus
Tomato leafroll virus
Subgroup III (i.e., Genus):
Bean golden mosaic virus
Preferred Member:
Bean golden mosaic virus (BGMV) (192)
Other Members:

| | |
|---|---|
| Abutilon mosaic virus | African cassava mosaic virusCotton |
| leaf crumple virus | Euphorbia mosaic virusHorsegram |
| yellow mosaic virus | Indian cassava mosaic virusJatropha |
| mosaic virus | Limabean golden mosaic virus |
| Malvaceous chlorosis virus | Melon leaf curl virus |
| Mungbean yellow mosaic virus | Potato yellow mosaic virus |
| Rhynochosia mosaic virus | Squash leaf curl virus |
| Tigre disease virus | Tobacco leaf curl virus |
| Tomato golden mosaic virus | Tomato leaf curl virus |
| Tomato yellow dwarf virus | Tomato yellow leaf curl virus |
| Tomato yellow mosaic virus | Watermelon curly mottle virus |
| Watermelon chlorotic stunt virus | |
| Honeysuckle yellow vein mosaic virus | |

Putative Members:

| | |
|---|---|
| Cotton leaf curl virus | Cowpea golden mosaic virus |
| Eggplant yellow mosaic virus | Eupatorium Yellow vein virus |
| Lupin leaf curl virus | Soyabean crinkle leaf virus |
| Solanum apical leaf curl virus | |
| Wissadula mosaic virus | |

VII. FAMILY: DSDNA ALGAL VIRUSES PHYCODNAVIRIDAE
Genus:
dsdna Phycovirus Phycodnavirus group Preferred Species:

*Paramecium bursaria* chlorella virus - 1 (PBCV - 1)
Viruses of:
*Paramecium bursaria* Chlorella NC64A viruses (NC64A viruses)
*Paramecium bursaria* Chlorella Pbi viruses (Pbi viruses)
Hydra virdis Chlorella viruses (HYCV)
Other Members:

Chlorella NC64A viruses (thirty-seven NC64A viruses, including PBCV-1)
Chlorella virus NE-8D (CV-NE8D; synonym NE-8D)

| | | |
|---|---|---|
| CV-NYb1 | CV-CA4B | CV-AL1A |
| CV-NY2C | CV-NC1D | CV-NCIC |
| CV-CA1A | CV-CA2A | CV-IL2A |
| CV-IL2B | CV-IL3A | CV-IL3D |
| CV-SC1A | CV-SC1B | CV-NC1A |
| CV-NE8A | CV-AL2C | CV-MA1E |
| CV-NY2F | CV-CA1D | CV-NC1B |
| CV-NYs1 | CV-IL5-2s1 | CV-AL2A |
| CV-MA1D | CV-NY2B | CV-CA4A |
| CV-NY2A | CV-XZ3A | CV-SH6A |
| CV-BJ2C | CV-XZ6E | CV-XZ4C |
| CV-XZ5C | CV-XZ4A | |

Chlorella Pbi viruses

| | | |
|---|---|---|
| CVA-1 | CVB-1 | CVG-1 |
| CVM-1 | CVR-1 | |

Hydra viridis Chlorella viruses

HVCV-1
HVCV-2
HVCV-3
VIII. FAMILY: POLYDNAVIRUS GROUP POLYDNAVIRIDAE
Genus:
Ichnovirus
Preferred Species:
Campoletis sonorensis virus (CsV)
Other Member:
Viruses of Glypta sp.
Genus:
Bracovirus
Preferred Species:
*Cotesia melanoscela* virus (CmV)

[1]These viruses are listin In: "Fifth Report of the International Committee on Taxonomy of Viruses" (ICTV) by Cornelia Buchen-Osmond, 1991, Research School of Biological Sciences, Canberra, Australia. Most viruses listed here are available from the American Type Culture Collection.

The genome of the non-mammalian DNA virus can be engineered to include one or more genetic elements. In general, these elements are selected based on their ability to facilitate expression of (i) an altered coat protein on the surface of a virus particle, and/or (ii) an exogenous gene in a mammalian cell.

Any transmembrane protein that binds to a target mammalian cell, or that mediates membrane fusion to allow escape from endosomes, can be used as the altered coat protein on the non-mammalian DNA virus. Preferably, the altered coat protein is the polypeptide (preferably a glycosylated version) of a glycoprotein that naturally mediates viral infection of a mammalian cell (e.g., a coat protein of a mammalian virus, such as a lentivirus, and influenza virus, a hepatitis virus, or a rhabdovirus). Other useful altered coat proteins include proteins that bind to a receptor on a mammalian cell and stimulate endocytosis. Examples of suitable altered coat proteins include, but are not limited to, the coat proteins listed in Table 2, which are derived from viruses such as HIV, influenza viruses, rhabdoviruses, and human respiratory viruses. An exemplary vesicular stomatitis virus glycoprotein G (VSV-G) is encoded by the plasmid BV-CZPG, the nucleotide sequence of which is shown in FIG. 23. If desired, more than one coat protein can be used as altered coat proteins. For example, a first altered coat protein may be a transmembrane protein that binds to a mammalian cell, and a second coat protein may mediate membrane fusion and escape from endosomes.

TABLE 2

EXAMPLES OF SUITABLE ALTERED COAT PROTEINS

| Viral Coat Protein | Reference |
|---|---|
| Vesicular Stomatitis Virus glycoprotein G | GenBank Accession # M21416[a] |
| Herpes Simplex Virus 1 (KOS) glycoprotein B | GenBank Accession # K01760 |
| Human Immunodeficiency Virus type 1 gp120 | GenBank Accession # U47783 |
| Influenza A Virus hemagglutinin | GenBank Accession # M38242 |
| Human Respiratory Syncytial Virus membrane glycoprotein | GenBank Accession # M86651 |
| Human Respiratory Syncytial Virus fusion protein | GenBank Accession # D00334 |
| Tick-Borne Encephalitis Virus glycoprotein E | GenBank Accession # S72426 |
| Pseudorabies Virus glycoprotein gH | GenBank Accession # M61196 |
| Rabies Virus G5803FX glycoprotein | GenBank Accession # U11753 |
| Human Rhinovirus 1B viral coat proteins VP1, VP2, and VP3 | GenBank Accession # D00239 |
| Semliki Forest Virus coat proteins E1, E2, and E3 | GenBank Accession # Z48163 |
| Human immunodeficiency Virus-1 envelope spike protein | Mebatsion et al., 1996, PNAS 93:11366–1370 |
| Herpes Simplex Virus-1 Entry Mediator | Montgomery et al., 1996, Cell 87:427–436 |
| Pseudorabies Virus Glycoprotein gE | Enquist et al., 1994, J. Virol. 68:5275–5279 |
| Herpes Simplex Virus Glycoprotein gB | Norais et al., 1996, J. Virol. 70:7379–7387 |
| Bovine Syncytial Virus Envelope Protein | Renshaw et al., 1991, Gene 105:179–184 |
| Human Foamy Virus (HFV) | GenBank Accession # Y07725 |
| Rabies Virus glycoprotein G | Gaudin et al., 1996, J. Virol. 70:7371–7378 |

[a]The GenBank accession numbers refer to nucleic acid sequences encoding the viral coat proteins.

In a preferred embodiment, the altered coat protein is produced as a fusion (i.e., chimeric) protein. A particularly useful fusion protein includes (i) a transmembrane polypeptide (e.g., antibodies such as IgM, IgG, and single chain antibodies) fused to (ii) a polypeptide that binds to a mammalian cell (e.g., VCAM, NCAM, integrins, and selectins) or to a growth factor. Included among the suitable transmembrane polypeptides are various coat proteins that naturally exist on the surface of a non-mammalian or mammalian virus particle (e.g., baculovirus gp64, influenza hemagglutinin protein, and Vesicular stomatitis virus glycoprotein G). All or a portion of the transmembrane polypeptide can be used, provided that the polypeptide spans the membrane of the virus particle, such that the polypeptide is anchored in the membrane. Non-viral transmembrane polypeptides also can be used. For example, a membrane-bound receptor can be fused to a polypeptide that binds a mammalian cell and used as the altered coat protein. Preferably, the fusion protein includes a viral coat protein (e.g., gp64) and a targeting molecule (e.g., VSV-G). Fusion polypeptides that include all or a cell-binding portion of a cell adhesion molecule also are included within the invention (e.g, a gp64-VCAM fusion protein).

Typically, the gene encoding the altered coat protein is operably linked to a promoter that is not active in the mammalian cell to be infected with the virus but is active in a non-mammalian cell used to propagate the virus (i.e., a "non-mammalian-active" promoter). By contrast, a mammalian-active promoter is used to drive expression of the exogenous gene of interest (e.g., a therapeutic gene), as is discussed below. Generally, promoters derived from viruses that replicate in non-mammalian cells, but which do not replicate in mammalian cells, are useful as non-mammalian active promoters. For example, when using a baculovirus as the non-mammalian DNA virus, a baculovirus polyhedrin promoter can be used to drive expression of the altered coat protein, since baculoviruses do not replicate in mammalian cells. Other examples of suitable non-mammalian active promoters include p10 promoters, p35 promoters, etl promoters, and gp64 promoters, all of which are active in baculoviruses. When insect cells are used to prepare a virus stock, this non-mammalian-active promoter allows the altered coat protein to be expressed on the surface of the resulting virus particles. Upon infecting a mammalian cell with the non-mammalian DNA virus having an altered coat protein, the polyhedrin promoter is inactive. Examples of suitable non-mammalian-active promoters for driving expression of altered coat proteins include baculoviral polyhedrin promoters (e.g., from pAcAb4 from Pharmingen, Inc.), p10 promoters (eg., from pAcAb4 from Pharmingen, Inc.), p39 promoters (see Xu et al., 1995, J. Virol. 69:2912–2917), gp64 promoters (including TATA-independent promoters; see Kogan et al., 1995, J. Virol. 69:1452–1461), baculoviral IE1 promoters (see Jarvis et al., 1996, Prot. Expr. Purif 8:191–203), and Drosophila alcohol dehydrogenase promoters (see Heberlein et al., 1995, Cell 41:965–977).

If desired, the non-mammalian-active promoter that is operably linked to the gene encoding the altered coat protein can be an inducible promoter that is activated in the non-mammalian cell in which the virus is propagated. Examples of suitable inducible promoters include promoters based on progesterone receptor mutants (Wang et al., 1994, Proc. Natl. Acad. Sci. 91:8180–8184), tetracycline-inducible promoters (Gossen et al., 1995, Science 268:1766–1760; 1992, Proc. Natl. Acad. Sci. 89:5547–5551, available from Clontech, Inc.), rapamycin-inducible promoters (Rivera et al., 1996, Nat. Med. 2:1028–1032), and ecdysone-inducible promoters (No et al., 1996, Proc. Natl. Acad. Sci. 93:3346–3351).

In principle, an inducible promoter that can be activated in either a non-mammalian or mammalian cell can be used in this embodiment of the invention, although in practice an inducer of the promoter typically would be added to the non-mammalian cell in which the virus is propagated, rather than the mammalian cell in which the exogenous gene is expressed. As an example, a gene encoding an altered coat protein can be operably linked to a promoter that is inducible by ecdysone (No et al., 1996, Proc. Natl. Acad. Sci. 93:3346–3351). In this case, the genome of the non-mammalian DNA virus is engineered to include a paired ecdysone response element operably linked to the gene encoding the altered coat protein. Expression of a heterodimeric ecdysone receptor in the presence of ecdysone (or an ecdysone analog) that is added to the cell activates gene expression from a promoter that is operably linked to a gene encoding an altered coat protein. The use of an inducible promoter to drive expression of the gene encoding the altered coat protein offers the advantage of providing an additional mechanism for controlling expression of the altered coat protein.

The genome of the non-mammalian DNA virus can be engineered to include additional genetic elements, such as a mammalian-active promoter of a long-terminal repeat of a transposable element or a retrovirus (e.g., Rous Sarcoma Virus); an inverted terminal repeat of an adeno-associated virus and an adeno-associated rep gene; and/or a cell-immortalizing sequence, such as the SV40 T antigen or c-myc. If desired, the genome of the non-mammalian DNA virus can include an origin of replication that functions in a mammalian cell (e.g., an Epstein Barr Virus (EBV) origin of replication or a mammalian origin of replication). Examples of mammalian origins of replication include sequences near the dihydrofolate reductase gene (Burhans et al., 1990, Cell 62:955–965), the β-globin gene (Kitsberg et al., 1993, Cell 366:588–590), the adenosine deaminase gene (Carroll et al., 1993, Mol. Cell. Biol. 13:2927–2981), and other human sequences (see Krysan et al., 1989, Mol. Cell. Biol. 9:1026–1033). If desired, the origin of replication can be used in conjunction with a factor that promotes replication of autonomous elements, such as the EBNA1 gene from EBV. The genome of the non-mammalian DNA virus used in the invention can include a polyadenylation signal and an RNA splicing signal that functions in mammalian cells (i.e., a "mammalian RNA splicing signal), positioned for proper processing of the product of the exogenous gene. In addition, the virus may be engineered to encode a signal sequence for proper targeting of the gene product.

The exogenous gene that is to be expressed in a mammalian cell is operably linked to a "mammalian-active" promoter (i.e., a promoter that directs transcription in a mammalian cell). Where cell-type specific expression of the exogenous gene is desired, the exogenous gene in the genome of the virus can be operably linked to a mammalian-active, cell-type-specific promoter, such as a promoter that is specific for liver cells, brain cells (e.g., neuronal cells), glial cells, Schwann cells, lung cells, kidney cells, spleen cells, muscle cells, or skin cells. For example, a liver cell-specific promoter can include a promoter of a gene encoding albumin, α-1-antitrypsin, pyruvate kinase, phosphoenol pyruvate carboxykinase, transferrin, transthyretin, α-fetoprotein, α-fibrinogen, or β-fibrinogen. Alternatively, a hepatitis virus promoter (e.g., hepatitis A, B, C, or D viral promoter) can be used. If desired, a hepatitis B viral enhancer may be used in conjunction with a hepatitis B viral promoter. Preferably, an albumin promoter is used. An α-fetoprotein promoter is particularly useful for driving expression of an exogenous gene when the invention is used to express a gene for treating a hepatocellular carcinoma Other preferred liver-specific promoters include promoters of the genes encoding the low density lipoprotein receptor, α2-macroglobulin, α1-antichymotrypsin, α2-HS glycoprotein, haptoglobin, ceruloplasmin, plasminogen, complement proteins (Clq, Clr, C2, C3, C4, C5, C6, C8, C9, complement Factor I and Factor H), C3 complement activator, β-lipoprotein, and α1-acid glycoprotein. For expression of an exogenous gene specifically in neuronal cells, a neuron-specific enolase promoter can be used (see Forss-Petter et al., 1990, Neuron 5: 187–197). For expression of an exogenous gene in dopaminergic neurons, a tyrosine hydroxylase promoter can be used. For expression in pituitary cells, a pituitary-specific promoter such as POMC may be useful (Hammer et al., 1990, Mol. Endocrinol. 4:1689–97). Typically, the promoter that is operably linked to the exogenous gene is not identical to the promoter that is operably linked to the gene encoding an altered coat protein.

Promoters that are inducible by external stimuli also can be used for driving expression of the exogenous gene. Such promoters provide a convenient means for controlling expression of the exogenous gene in a cell of a cell culture or within a mammal. Preferred inducible promoters include enkephalin promoters (e.g., the human enkephalin promoter), metallothionein promoters, mouse mammary tumor virus promoters, promoters based on progesterone receptor mutants, tetracycline-inducible promoters, rapamycin-inducible promoters, and ecdysone-inducible promoters. Methods for inducing gene expression from each of these promoters are known in the art.

Essentially any mammalian cell can be used in the invention; preferably, the mammalian cell is a human cell. The cell can be a primary cell (e.g., a primary hepatocyte, primary neuronal cell, or primary myoblast) or it may be a cell of an established cell line. It is not necessary that the cell be capable of undergoing cell division; a terminally differentiated cell can be used in the invention. If desired, the virus can be introduced into a primary cell approximately 24 hours after plating of the primary cell to maximize the efficiency of infection. Preferably, the mammalian cell is a liver-derived cell, such as a HepG2 cell, a Hep3B cell, a Huh-7 cell, an FTO2B cell, a Hepal-6 cell, or an SK-Hep-1 cell) or a Kupffer cell; a kidney cell, such as a cell of the kidney cell line 293, a PC12 cell (e.g., a differentiated PC12 cell induced by nerve growth factor), a COS cell (e.g., a COS7 cell), or a Vero cell (an African green monkey kidney cell); a neuronal cell, such as a fetal neuronal cell, cortical pyramidal cell, mitral cell, a granule cell, or a brain cell (e.g., a cell of the cerebral cortex; an astrocyte; a glial cell; a Schwann cell); a muscle cell, such as a myoblast or myotube (e.g., a $C_2C_{12}$ cell); an embryonic stem cell, a spleen cell (e.g., a macrophage or lymphocyte); an epithelial cell, such as a HeLa cell (a human cervical carcinoma epithelial line); a fibroblast, such as an NIH3T3 cell; an endothelial cell; a WISH cell; an A549 cell; or a bone marrow stem cell. Other preferred mammalian cells include CHO/dhfr$^-$ cells, Ramos, Jurkat, HL60, and K-562 cells.

The virus can be introduced into a cell in vitro or in vivo. Where the virus is introduced into a cell in vitro, the infected cell can subsequently be introduced into a mammal, if desired. Accordingly, expression of the exogenous gene can be accomplished by maintaining the cell in vitro, in vivo, or in vitro and in vivo, sequentially. Similarly, where the invention is used to express an exogenous gene in more than one cell, a combination of in vitro and in vivo methods may be used to introduce the gene into more than one mammalian cell.

If desired, the virus can be introduced into the cell by administering the virus to a mammal that carries the cell. For example, the virus can be administered to a mammal by subcutaneous, intravascular, or intraperitoneal injection. If desired, a slow-release device, such as an implantable pump, may be used to facilitate delivery of the virus to cells of the mammal. A particular cell type within the mammal can be targeted by modulating the amount of the virus administered to the mammal and by controlling the method of delivery. For example, intravascular administration of the virus to the portal, splenic, or mesenteric veins or to the hepatic artery may be used to facilitate targeting the virus to liver cells. In another method, the virus may be administered to cells or an organ of a donor individual (human or non-human) prior to transplantation of the cells or organ to a recipient.

In a preferred method of administration, the virus is administered to a tissue or organ containing the targeted cells of the mammal. Such administration can be accomplished by injecting a solution containing the virus into a tissue, such as skin, brain (e.g., the cerebral cortex), kidney, bladder, liver, spleen, muscle, thyroid, thymus, lung, or colon tissue. Alternatively, or in addition, administration can be accomplished by perfusing an organ with a solution containing the virus, according to conventional perfusion protocols.

In another preferred method, the virus is administered intranasally, e.g., by applying a solution of the virus to the nasal mucosa of a mammal. This method of administration can be used to facilitate retrograde transportation of the virus into the brain. This method thus provides a means for delivering the virus to brain cells, (e.g., mitral and granule neuronal cells of the olfactory bulb) without subjecting the mammal to surgery.

In an alternative method for using the virus to express an exogenous gene in the brain, the virus is delivered to the brain by osmotic shock according to conventional methods for inducing osmotic shock.

Where the cell is maintained under in vitro conditions, conventional tissue culture conditions and methods may be used. In a preferred method, the cell is maintained on a substrate that contains collagen, such as Type I collagen or rat tail collagen, or a matrix containing laminin. As an alternative to, or in addition to, maintaining the cell under in vitro conditions, the cell can be maintained under in vivo conditions (e.g., in a human). Implantable versions of collagen substrates are also suitable for maintaining the virus-infected cells under in vivo conditions in practicing the invention (see, e.g., Hubbell et al., 1995, Bio/Technology 13:565–576 and Langer and Vacanti, 1993, Science 260: 920–925).

The invention can be used to express a variety of exogenous genes encoding gene products such as a polypeptides or proteins, antisense RNAs, and catalytic RNAs. If desired, the gene product (e.g., protein or RNA) can be purified from the mammalian cell. Thus, the invention can be used in the manufacture of a wide variety of proteins that are useful in the fields of biology and medicine.

Where the invention is used to express an antisense RNA, the preferred antisense RNA is complementary to a nucleic acid (e.g., an mRNA) of a pathogen of the mammalian cell (e.g., a virus, a bacterium, or a fungus). For example, the invention can be used in a method of treating a hepatitis viral infection by expressing an antisense RNA that hybridizes to an mRNA of an essential hepatitis virus gene product (e.g., a polymerase mRNA). Other preferred antisense RNAs include those that are complementary to a naturally-occurring gene in the cell, which gene is expressed at an undesirably high level. For example, an antisense RNA can be designed to inhibit expression of an oncogene in a mammalian cell. Similarly, the virus can be used to express a catalytic RNA (i.e., a ribozyme) that inhibits expression of a target gene in the cell by hydrolyzing an mRNA encoding the targeted gene product. Antisense RNAs and catalytic RNAs can be designed by employing conventional criteria.

If desired, the invention can be used to express a dominant negative mutant in a mammalian cell. For example, viral assembly in a cell can be inhibited or prevented by expressing in that cell a dominant negative mutant of a viral capsid protein (see, e.g., Scaglioni et al., 1994, Virology 205:112–120; Scaglioni et al., 1996, Hepatology 24:1010–1017; and Scaglioni et al., 1997, J. Virol. 71:345–353).

The invention can be used to express any of various "therapeutic" genes in a cell. A "therapeutic" gene is one that when expressed, confers a beneficial effect on the cell or tissue in which it is present, or on a mammal in which the gene is expressed. Examples of "beneficial effects" include amelioration of a sign or symptom of a condition or disease, prevention or inhibition of a condition or disease, or conferral of a desirable characteristic. Included among the therapeutic genes are those genes that correct a gene deficiency disorder in a cell or mammal. For example, carbamoyl synthetase I can correct a gene deficiency disorder when it is expressed in a cell that previously failed to express, or expressed insufficient levels of, carbamoyl synthetase I. "Correction" of a gene deficiency disorder need not be equivalent to curing a patient suffering from a disorder. All that is required is conferral of a beneficial effect, including even temporary amelioration of signs or symptoms of the disorder. Also included are genes that are expressed in one cell, yet which confer a beneficial effect on a second cell. For example, a gene encoding insulin can be expressed in a pancreatic cell, from which the insulin is then secreted to exert an effect on other cells of the mammal. Other therapeutic genes include sequences that encode antisense RNAs nucleic acid that inhibit transcription or translation of a gene that is expressed at an undesirably high level. For example, an antisense gene that inhibits expression of a gene encoding an oncogenic protein is considered a therapeutic gene. "Cancer therapeutic" genes are those genes that confer a beneficial effect on a cancerous cell or a mammal suffering from cancer. Particularly useful cancer therapeutic genes include the p53 gene, a herpes simplex virus thymidine kinase gene, and an antisense gene that is complementary to an oncogene.

The invention can be used to express a therapeutic gene in order to treat a gene deficiency disorder. Particularly appropriate genes for expression include those genes that are thought to be expressed at a less than normal level in the target cells of the subject mammal. Particularly useful gene products include carbamoyl synthetase I, ornithine transcarbamylase, arginosuccinate synthetase, arginosuccinate lyase, and arginase. Other desirable gene products include fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione β-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, -glucosidase, pyruvate carboxylase, hepatic phosphorylase, phosphorylase kinase, glycine decarboxylase (also referred to as P-protein), H-protein, T-protein, Menkes disease copper-transporting ATPase, Wilson's disease copper-transporting ATPase, and CFTR (e.g., for treating cystic fibrosis).

The invention can also be used to express in a mammalian cell a gene that is expected to have a biological effect in mammals but not in insects (i.e., a "mammal-specific" gene). For example, a baculovirus genome can be used to express a mammalian myoD gene and thereby produce muscle proteins; such a gene would be expected to have a biological effect in mammalian cells but not insect cells. Other examples of mammal-specific genes include, but are not limited to, transcription factors that function in mammalian, but not insect, cells. For example, the transcription factors c/ebp-alpha and chop10 will activate liver cell differentiation pathways when expressed from an insect genome (e.g., a baculovirus genome) in a mammalian cell. In contrast, expression of these mammal-specific transcription factors in an insect cell would be expected to have a minimal, or no, effect on the insect cell.

If desired, the vectors of the invention can be used to propagate genetic constructs in non-mammalian (e.g., insect) cells, with the advantage of inhibiting DNA methylation of the product. It has been observed that a promoter may become methylated in cell lines or tissues in which it is not normally expressed, and that such methylation is inhibitory to proper tissue specific expression (Okuse et al., 1997, Brain Res. Mol. Brain Res. 46:197–207; Kudo et al., 1995, J. Biol. Chem. 270:13298–13302). For example, a neural promoter may become methylated in a non-neural mammalian cell. By using, for example, insect cells (e.g., Sf9 cells) to propagate a baculovirus carrying an exogenous gene and a mammalian promoter (e.g., a neural promoter), the invention provides a means for inhibiting DNA methylation of the promoter prior to administration of the baculovirus and exogenous gene to the mammalian cell in which the exogenous gene will be expressed (e.g., a neural cell).

Definitions

By "non-mammalian" DNA virus is meant a virus that has a DNA genome (rather than RNA) and which is naturally incapable of replicating in a vertebrate, and specifically a mammalian, cell. Included are insect viruses (e.g., baculoviruses), amphibian viruses, plant viruses, and fungal viruses. Viruses that naturally replicate in prokaryotes are excluded from this definition. Examples of viruses that are useful in practicing the invention are listed in Table 1. As used herein, a "genome" can include all or some of the nucleic acid sequences present in a naturally-occurring non-mammalian DNA virus. If desired, genes or sequences can be removed from the virus genome or disabled (e.g., by mutagenesis), provided that the virus retains, or is engineered to retain, its ability to express an exogenous gene in a mammalian cell. For example, the virus can be engineered such that it lacks a functional polyhedrin gene. Such a virus can be produced by deleting all or a portion of the polyhedrin gene from a virus genome (e.g., a baculovirus genome) or by introducing mutations (e.g., a frameshift mutation) into the polyhedrin gene so that the activity of the gene product is inhibited.

By "insect" DNA virus is meant a virus that has a DNA genome and which is naturally capable of replicating in an insect cell (e.g., Baculoviridae, Iridoviridae, Poxviridae, Polydnaviridae, Densoviridae, Caulimoviridae, and Phycodnaviridae).

By "exogenous" gene or promoter is meant any gene or promoter that is not normally part of the non-mammalian DNA virus (e.g., baculovirus) genome. Such genes include those genes that normally are present in the mammalian cell to be infected; also included are genes that are not normally present in the mammalian cell to be infected (e.g., related and unrelated genes of other cells or species). As used herein, the term "exogenous gene" excludes a gene encoding an "altered coat protein."

By "altered coat protein" is meant any polypeptide that (i) is engineered to be expressed on the surface of a virus particle, (ii) is not naturally present on the surface of the non-mammalian DNA virus used to infect a mammalian cell, and (iii) allows entry to a mammalian cell by binding to the cell and/or facilitating escape from the mammalian endosome into the cytosol of the cell. Typically, a gene encoding an altered coat protein is incorporated into the genome of the non-mammalian DNA virus used in the invention. If desired, a virus genome can be constructed such that the virus expresses a polypeptide that binds a mammalian receptor or counterreceptor on a mammalian cell. An altered coat protein can include all or a portion of a coat protein of a "mammalian" virus, i.e., a virus that naturally infects and replicates in a mammalian cell (e.g., an influenza virus). If desired, the altered coat protein can be a "fusion protein," i.e., an engineered protein that includes part or all of two (or more) distinct proteins derived from one or multiple distinct sources (e.g., proteins of different species). Typically, a fusion protein used in the invention includes (i) a polypeptide that has a transmembrane region of a transmembrane protein (e.g., baculovirus gp64) fused to (ii) a polypeptide that binds a mammalian cell (e.g., an extracellular domain of VSV-G).

Although the term "altered" is used in reference to the coat protein (because it is altered in the sense that it is expressed on the surface of a virus particle on which it is not normally found), the protein itself need not differ in sequence or structure from a wild-type version of the protein. Thus, a wild-type transmembrane protein that binds a mammalian cell can be used as the altered coat protein (e.g., a wild-type influenza virus hemagglutinin protein). Indeed, wild-type proteins are preferred. Nonetheless, non-wild-type proteins also can be used as the "altered" coat protein, provided that the non-wild-type coat protein retains the ability to bind to a mammalian cell. Examples of non-wild-type proteins include truncated proteins, mutant proteins (e.g., deletion mutants), and conservative variations of transmembrane polypeptides that bind a mammalian cell.

"Conservative variation" denotes the replacement of an amino acid residue by another, functionally similar, residue. Examples of conservative variations include the substitution of one hydrophobic residue, such as alanine, isoleucine, valine, leucine, or methionine, for another, or the substitution of one polar residue for another, such as the substitution of arginine for lysine, glatamic acid for aspartic acid, or glutamine for asparagine, and the like. The term "conservative variation" also includes the use of a substituted amino acid (i.e., a modified amino acid, such as Hydroxylysine) in place of an unsubstituted parent amino acid.

By "positioned for expression" is meant that the DNA sequence that includes the reference gene (e.g., the exogenous gene) is positioned adjacent to a DNA sequence that directs transcription of the DNA and, if desired, translation of the RNA (i.e., facilitates the production of the desired gene product).

By "promoter" is meant at least a minimal sequence sufficient to direct transcription. A "mammalian-active" promoter is one that is capable of directing transcription in a mammalian cell. The term "mammalian-active" promoter includes promoters that are derived from the genome of a mammal, i.e., "mammalian promoters," and promoters of viruses that are naturally capable of directing transcription in mammals (e.g., an MMTV promoter). Other promoters that are useful in the invention include those promoters that are sufficient to render promoter-dependent gene expression controllable for cell-type specificity, cell-stage specificity, or tissue-specificity (e.g., liver-specific promoters), and those promoters that are "inducible" by external signals or agents (e.g., metallothionein, MMTV, and pENK promoters); such elements can be located in the 5' or 3' regions of the native gene. The promoter sequence can be one that does not occur in nature, so long as it functions in a mammalian cell. An "inducible" promoter is a promoter that, (a) in the absence of an inducer, does not direct expression, or directs low levels of expression, of a gene to which the inducible promoter is operably linked; or (b) exhibits a low level of expression in the presence of a regulating factor that, when removed, allows high-level expression from the promoter (e.g., the tet system). In the presence of an inducer, an inducible promoter directs transcription at an increased level.

By "operably linked" is meant that a gene and a regulatory sequence(s) (e.g., a promoter) are connected in such a way as to permit gene expression when the appropriate molecules (e.g., transcriptional activator proteins) are bound to the regulatory sequence(s).

By "cell-immortalizing sequence" is meant a nucleic acid that, when present in a mammalian cell, is capable of transforming the cell for prolonged inhibition of senescence. Included are SV40 T-antigen, c-myc, telomerase, and E1A.

By "antisense" nucleic acid is meant a nucleic acid molecule (i.e., RNA) that is complementary (i.e., able to hybridize) to all or a portion of a target nucleic acid (e.g., a gene or mRNA) that encodes a polypeptide of interest. If desired, conventional methods can be used to produce an antisense nucleic acid that contains desirable modifications. For example, a phosphorothioate oligonucleotide can be used as the antisense nucleic acid in order to inhibit degradation of the antisense oligonucleotide by nucleases in vivo. Where the antisense nucleic acid is complementary to only a portion of the target nucleic acid encoding the polypeptide to be inhibited, the antisense nucleic acid should hybridize close enough to some critical portion of the target nucleic acid (e.g., in the translation control region of the non-coding sequence, or at the 5' end of the coding sequence) such that it inhibits translation of a functional polypeptide (i.e., a polypeptide that carries out an activity that one wishes to inhibit (e.g., an enzymatic activity)). Typically, this means that the antisense nucleic acid should be complementary to a sequence that is within the 5' half or third of a target mRNA to which the antisense nucleic acid hybridizes. As used herein, an "antisense gene" is a nucleic acid that is transcribed into an antisense RNA. Typically, such an antisense gene includes all or a portion of the target nucleic acid, but the antisense gene is operably linked to a promoter such that the orientation of the antisense gene is opposite to the orientation of the sequence in the naturally-occurring gene.

Use

The invention is useful for expressing an exogenous gene(s) in a mammalian cell in vitro or in vivo (e.g., a HepG2 cell). This method can be employed in the manufacture of proteins to be purified, such as proteins that are administered as pharmaceutical agents (e.g., insulin). The virus of the invention can also be used therapeutically. For example, the invention can be used to express in a patient a gene encoding a protein that corrects a deficiency in gene expression. In alternative methods of therapy, the invention can be used to express any protein, antisense RNA, or catalytic RNA in a cell.

The non-mammalian viral expression system of the invention offers several advantages. The altered coat protein on the virus enhances the ability of the non-mammalian DNA virus to infect and express a gene in a mammalian cell. Such a coat protein also can be used to confer cell-type specificity on the engineered virus. For example, expression of CD4$^+$ on a cell enhances the ability of a virus expressing an HV envelope gp120 protein to infect such CD4$^+$ cells (Mebatsion et al., 1996, Proc. Natl. Acad. Sci. 93:11366–11370).

The invention allows for de novo expression of an exogenous gene; thus, detection of the exogenous protein (e.g., β-galactosidase) in an infected cell represents protein that was actually synthesized in the infected cell, as opposed to protein that is carried along with the virus aberrantly. Because the non-mammalian viruses used in the invention are not normally pathogenic to humans and do not replicate in mammalian cells, concerns about safe handling of these viruses are minimized. Similarly, because the majority of naturally-occurring viral promoters are not normally active in a mammalian cell, production of undesired viral proteins is minimized. While traditional gene therapy vectors are based upon defective viruses that are propagated with helper virus or on a packaging line, the invention employs a virus that is not defective for growth on insect cells for purposes of virus propagation, but is intrinsically, and desirably, defective for growth on mammalian cells. Accordingly, in contrast to some mammalian virus-based gene therapy methods, the non-mammalian virus-based methods of the invention should not provoke a host immune response to proteins expressed by the virus in the mammalian cells.

The non-mammalian virus used in the invention can be propagated with cells grown in serum-free media, eliminating the risk of adventitious infectious agents occasionally present in the serum contaminating a virus preparation. In addition, the use of serum-free media eliminates a significant expense faced by users of mammalian viruses. Certain non-mammalian viruses, such as baculoviruses, can be grown to a high titer (i.e., $10^8$ pfu/ml). Generally, the large virus genomes that can be used in the invention (e.g., the baculovirus genome at 130 kbp) can accept large exogenous DNA molecules (e.g., 100 kb). In certain embodiments, the invention employs a virus whose genome has been engineered to contain an exogenous origin of replication (e.g., the EBV oriP). The presence of such sequences on the virus genome allows episomal replication of the virus, increasing persistence in the cell. Where the invention is used in the manufacture of proteins to be purified from the cell, the invention offers the advantage that it employs a mammalian expression system. Accordingly, one can expect proper post-translational processing and modification (e.g., glycosylation) of the product of the exogenous gene.

Other features and advantages of the invention will be apparent from the following detailed description, and from the claims.

BRIEF DESCRIPTION OF THE DRAWINGS

FIG. 1 is a schematic representation of the AcMNPV RSV-lacZ transfer plasmid pZ4.

FIG. 2 is a schematic representation of the occluded AcMNPV RSV-lacZ transfer plasmid pZ5.

FIG. 3 is a schematic representation of the episomal transfer plasmid pZ-EBV#1, a chimera of baculovirus and Epstein Barr Virus sequences. A virus produced with this transfer plasmid is capable of replicating in a mammalian cell.

FIG. 4A is a schematic representation of a transfer plasmid that allows excision of a gene cassette.

FIG. 4B is a schematic representation of the gene cassette excised by the transfer plasmid of FIG. 4A. Excision of the gene cassette is mediated by cre-lox recombination. This strategy allows persistence of an exogenous gene in the absence of viral sequences.

FIG. 5 is a schematic representation of the transfer plasmid, pBV-AVneo, a chimera of baculovirus and Adeno-associated virus sequences. This plasmid is capable of integrating into the genome of the infected cell.

FIG. 6 is a schematic representation of the AcMNPV transfer plasmid pCMV-BV.

FIG. 7 is a schematic representation of the AcMNPV transfer plasmid pCMVZ-BV.

FIG. 8 is a schematic representation of the AcMNPV transfer plasmid pAct-BV.

FIG. 9 is a schematic representation of the AcMNPV transfer plasmid pAZ-BV.

FIG. 10 is a schematic representation of the AcMNPV transfer plasmid pIE45-BV.

FIGS. 14A–D are photographs of cells that were stained with X-gal one day post-infection with an AcMNPV virus containing a RSV-lacZ cassette. Cells expressing the lacZ gene stain darkly with X-gal.

Figure 14A:

FIG. 14A is a photograph of a typical field of HepG2 cells infected at a multiplicity of infection of 15.

Figure 14B:
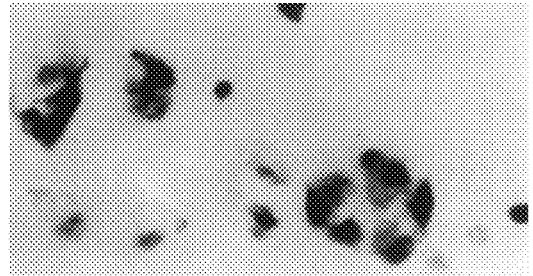

FIG. 14B is a photograph of a typical field of HepG2 cells infected at a multiplicity of infection of 125; over 25% of the cells were stained.

Figure 14C:
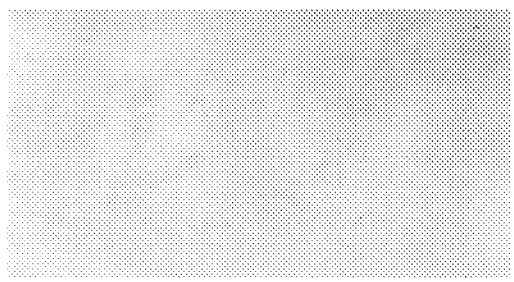

FIG. 14C is a typical field of Sk-Hep-1 cells infected at a multiplicity of infection of 125, showing no positively-stained cells.

Figure 14D:

FIG. 14D is a less typical field of Sk-Hep-1 cells infected at a multiplicity of infection of 125 showing a positively-stained cell. Bar=55 μm.

Figure 15:

FIG. 15 is a photograph of cells obtained following baculovirus-mediated gene transfer into primary cultures of rat hepatocytes. Over 70% of the cells were stained blue.

Figure 16:
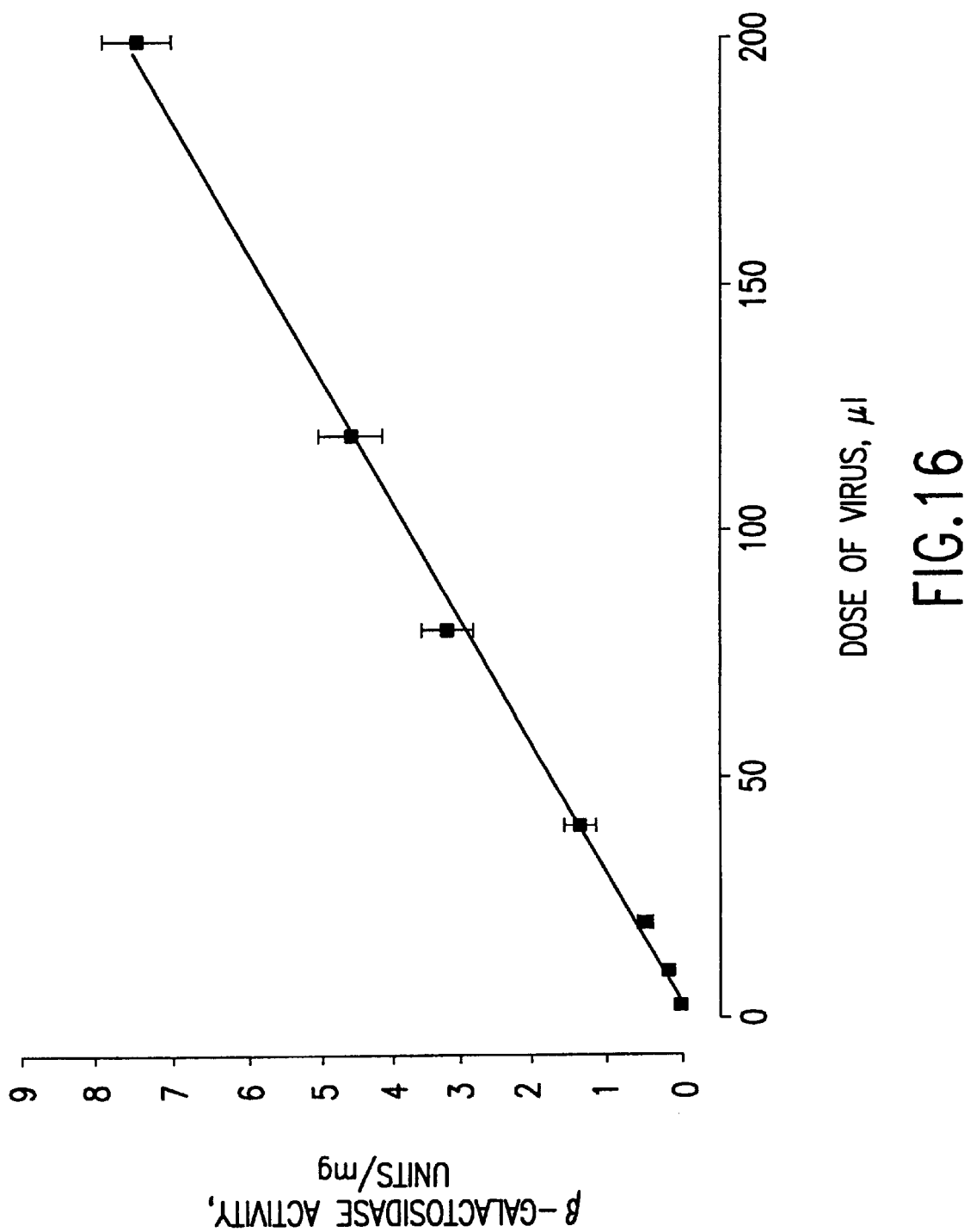

FIG. 16 is a graph displaying the dose-dependence of baculovirus-mediated gene transfer. Here, $10^6$ HepG2 cells were seeded into 60 mm petri dishes, and one day later the cells were exposed to the indicated dose of an AcMNPV virus containing a RSV-lacZ cassette (viral titer=$1.4 \times 10^9$ pfu/ml). At one day post-infection, the cells were harvested, and extracts were prepared and assayed for β-galactosidase enzyme activity. Extract activity is expressed in units of β-galactosidase activity as previously defined (Norton-and Coffin, 1985, Mol. Cell. Biol. 5:281–290). Enzyme activity was normalized for the protein content of each extract. Each point is the average of three independent assays, with the error bars representing the standard deviation.

Figure 17:
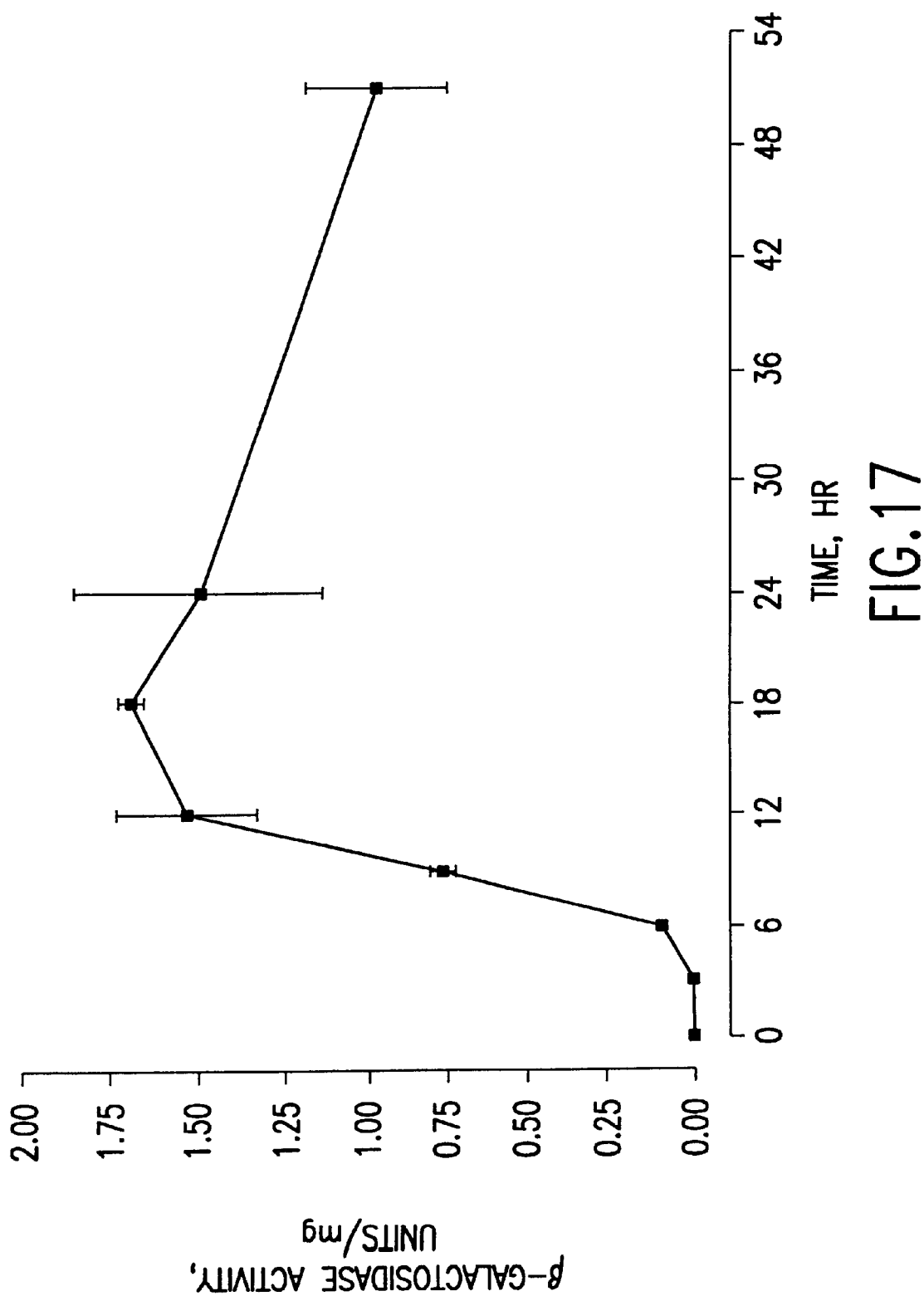

FIG. 17 is a graphic representation of results obtained in a time course of baculovirus-mediated expression. HepG2 cells were infected with AcMNPV virus containing a RSV-lacZ cassette (multiplicity of infection=15) at time zero. After one hour, the medium containing the virus was removed and replaced with fresh medium. Infected cells were harvested at the indicated time points and assayed for P-galactosidase activity as is described above. Each plotted point is expressed as the average of three independent assays, with the error bars representing the standard deviation. Expression from the virus peaked 12–24 hours post-infection and declined thereafter when normalized to total cellular protein.

Figure 18:
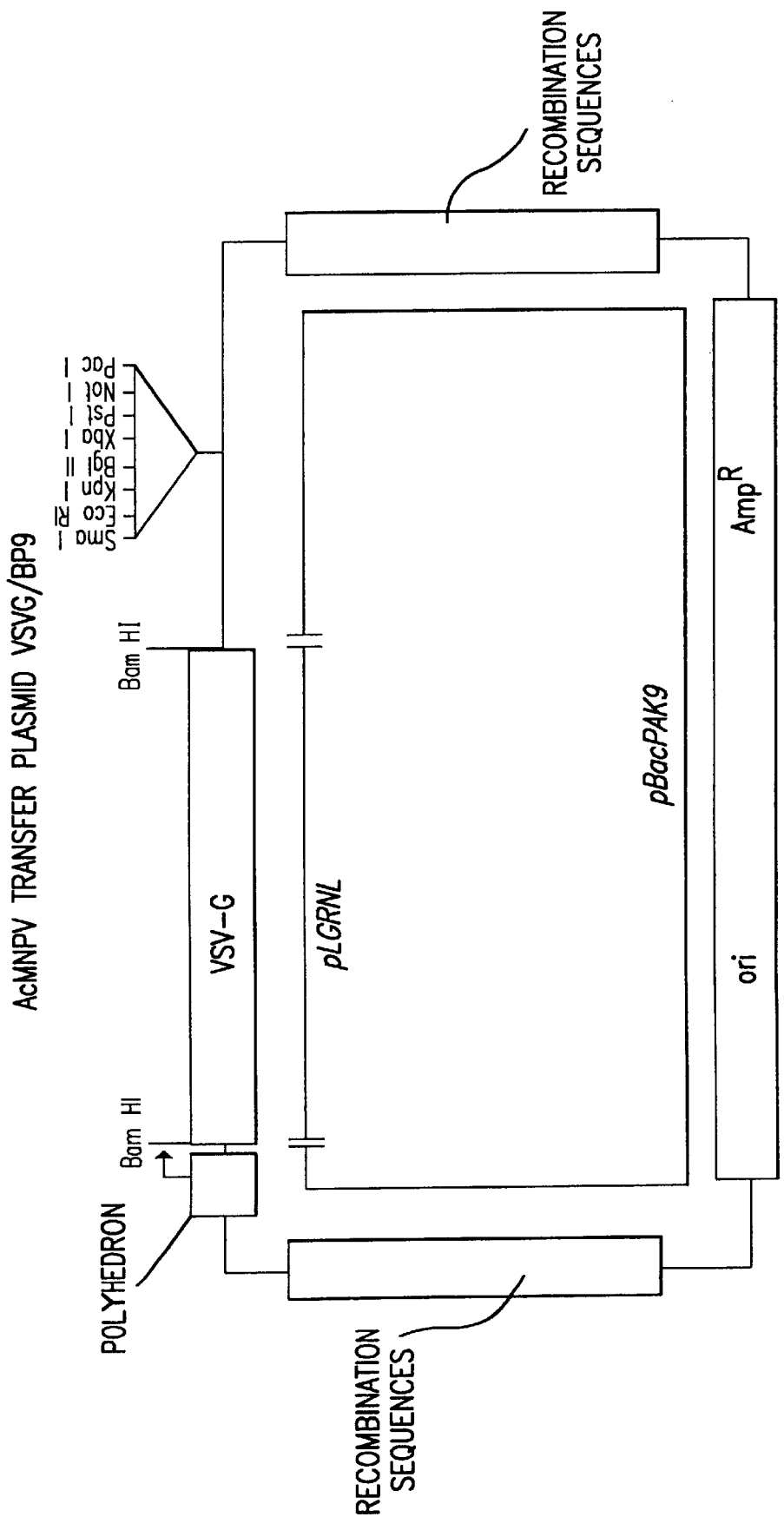

FIG. 18 is a schematic representation of the AcMNPV transfer plasmid VSVG/BP9.

Figure 19:
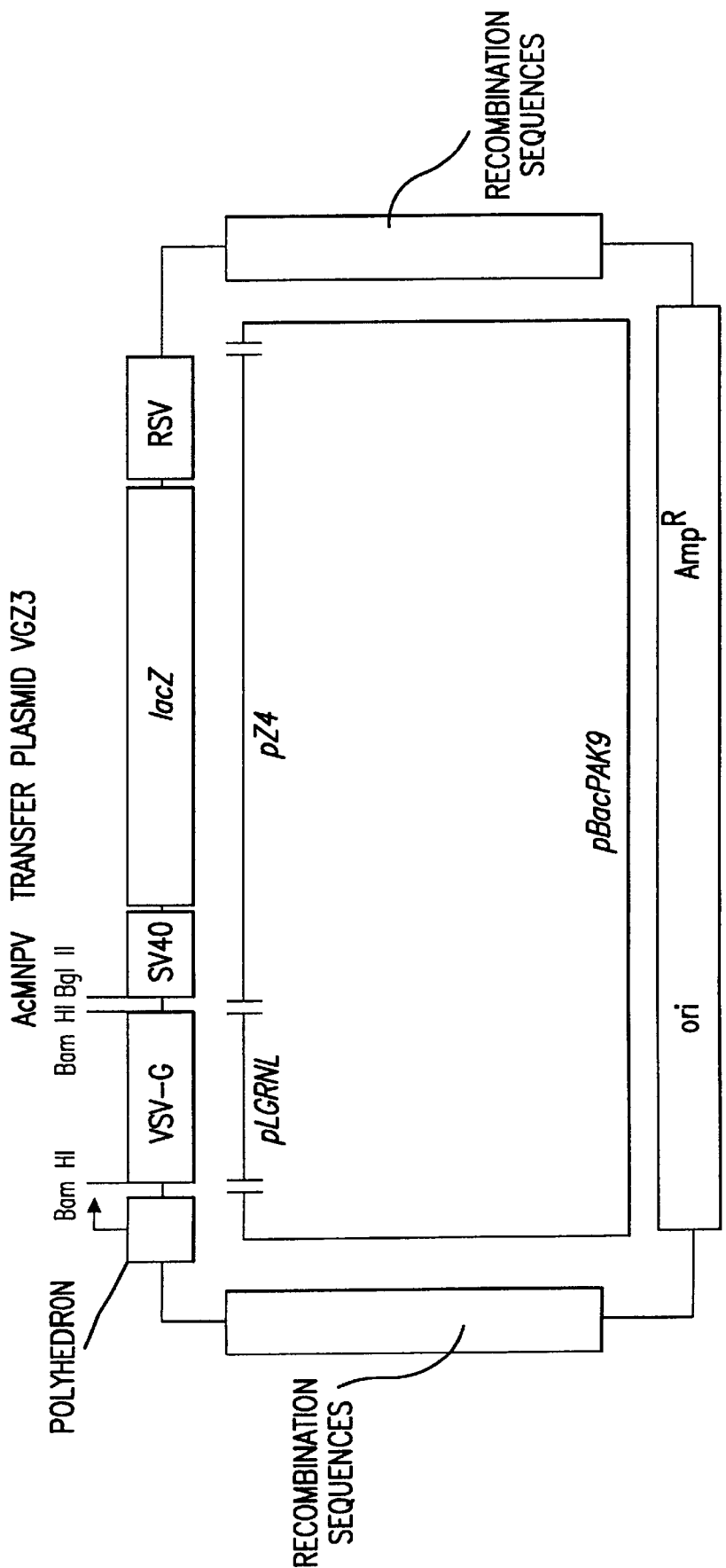

FIG. 19 is a schematic representation of the AcMNPV transfer plasmid VGZ3.

Figure 20:
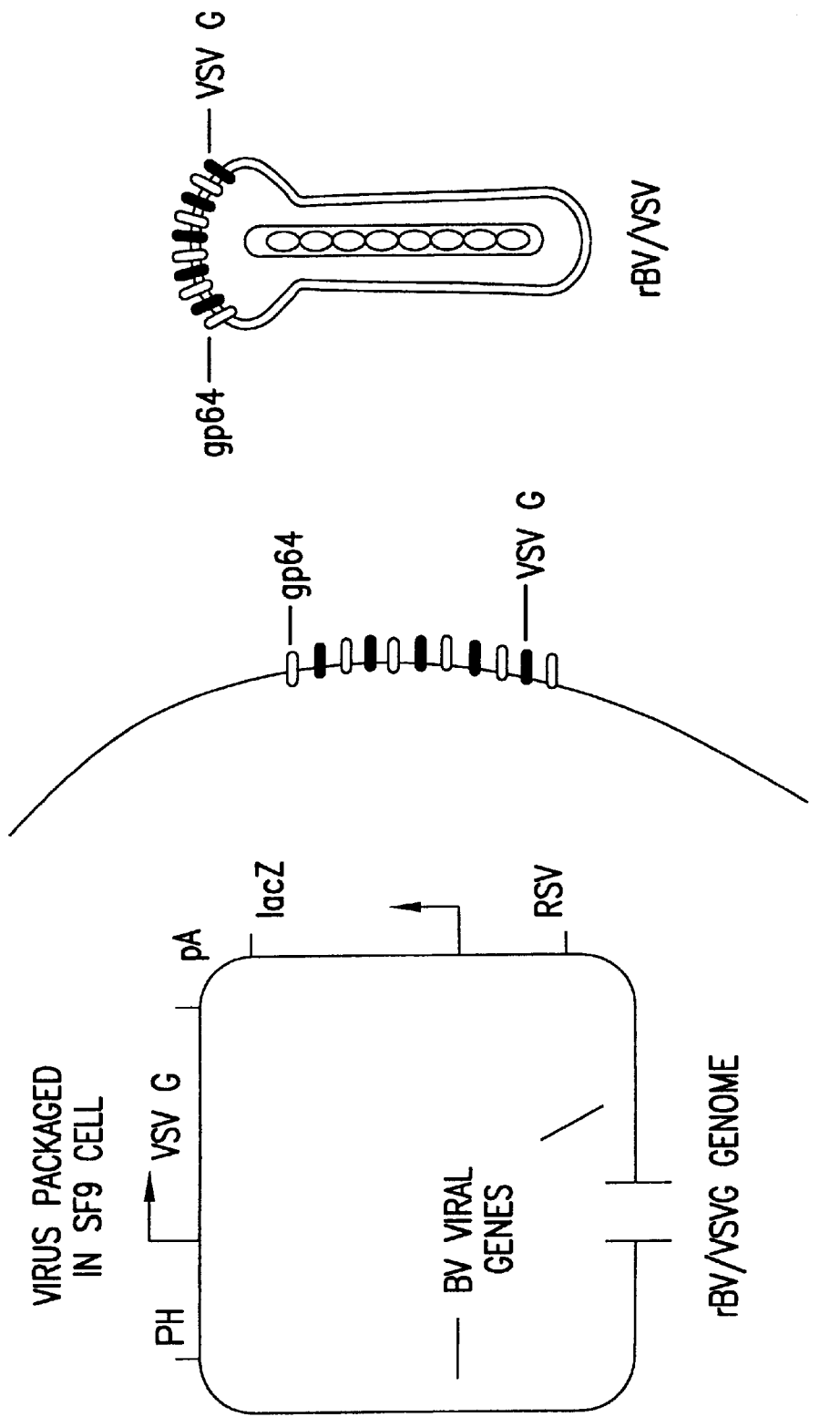
Figure 21A:
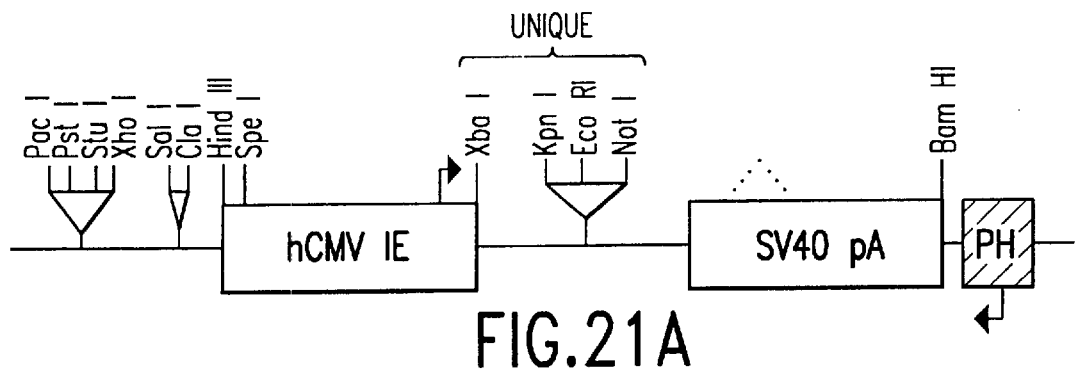
Figure 21B:
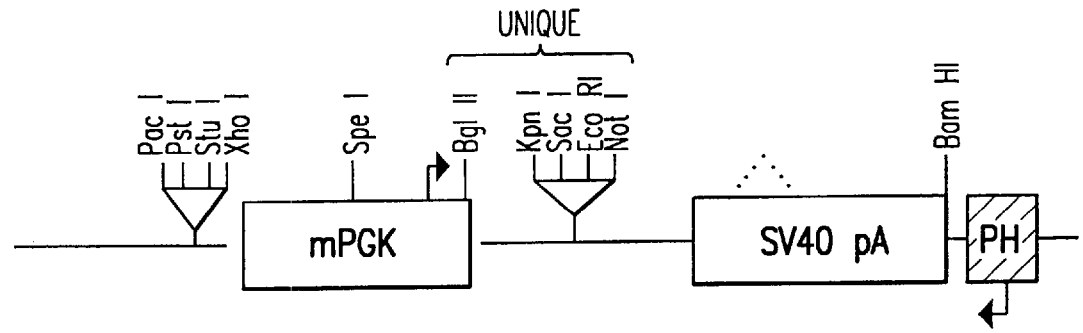
Figure 21C:
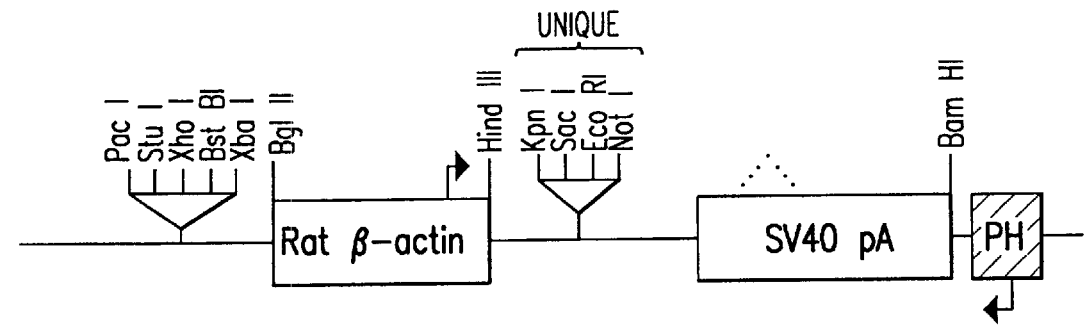
Figure 21D:
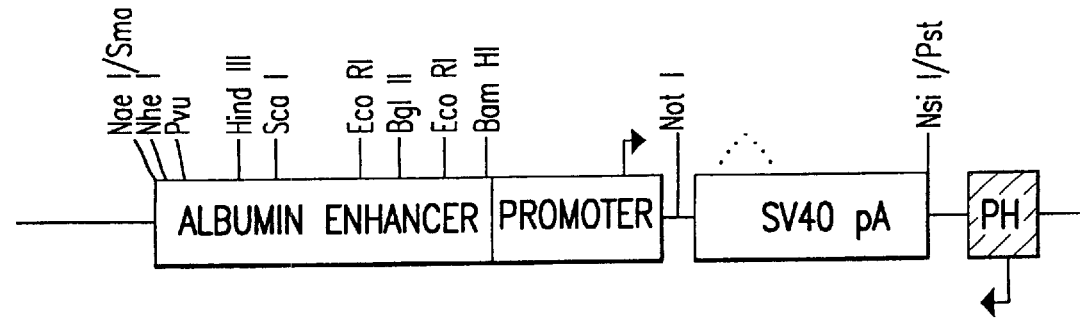

FIG. 20 is a schematic representation of a budding baculovirus having an altered coat protein. The natural baculovirus cell surface protein (gp64) and the VSV-G protein are represented by "gp64" and "VSV G."

FIG. 21 is a schematic representation of various baculoviral transfer vectors, in which an exogenous gene is operably linked to a viral or mammalian promoter.

Figure 22:
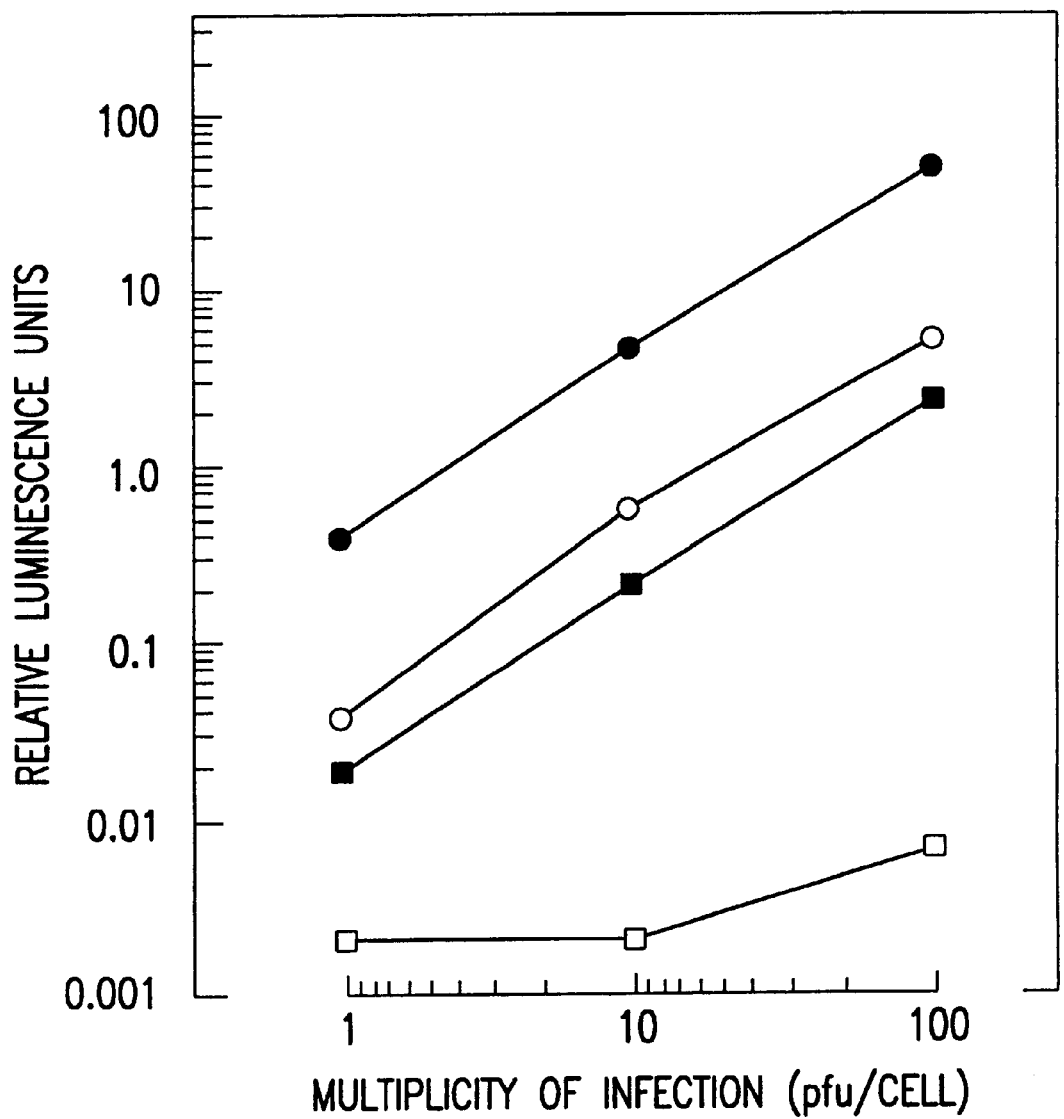

FIG. 22 is a graphic representation of the relative transduction efficiencies of Z4 and VGZ3 in HeLa and HepG2 cells. HeLa and HepG2 cells were treated with the VSV G-lacking baculovirus Z4 or the VSV G-containing baculovirus VGZ3 at multiplicities of infection of 1, 10, and 100. Expression of the lacZ gene was determined on the following day by a in vitro chemiluminescence assay. -•-, HepG2 cells treated with VGZ3; -○-, HepG2 treated with Z4; -■-, HeLa treated with VGZ3; -□-, HeLa treated with Z4.

FIG. 23 is a listing of the nucleotide sequence of plasmid BV-CZPG, which encodes a vesicular stomatitis virus G glycoprotein.

DETAILED DESCRIPTION

Genetic Manipulation of Viruses

Figure 1:
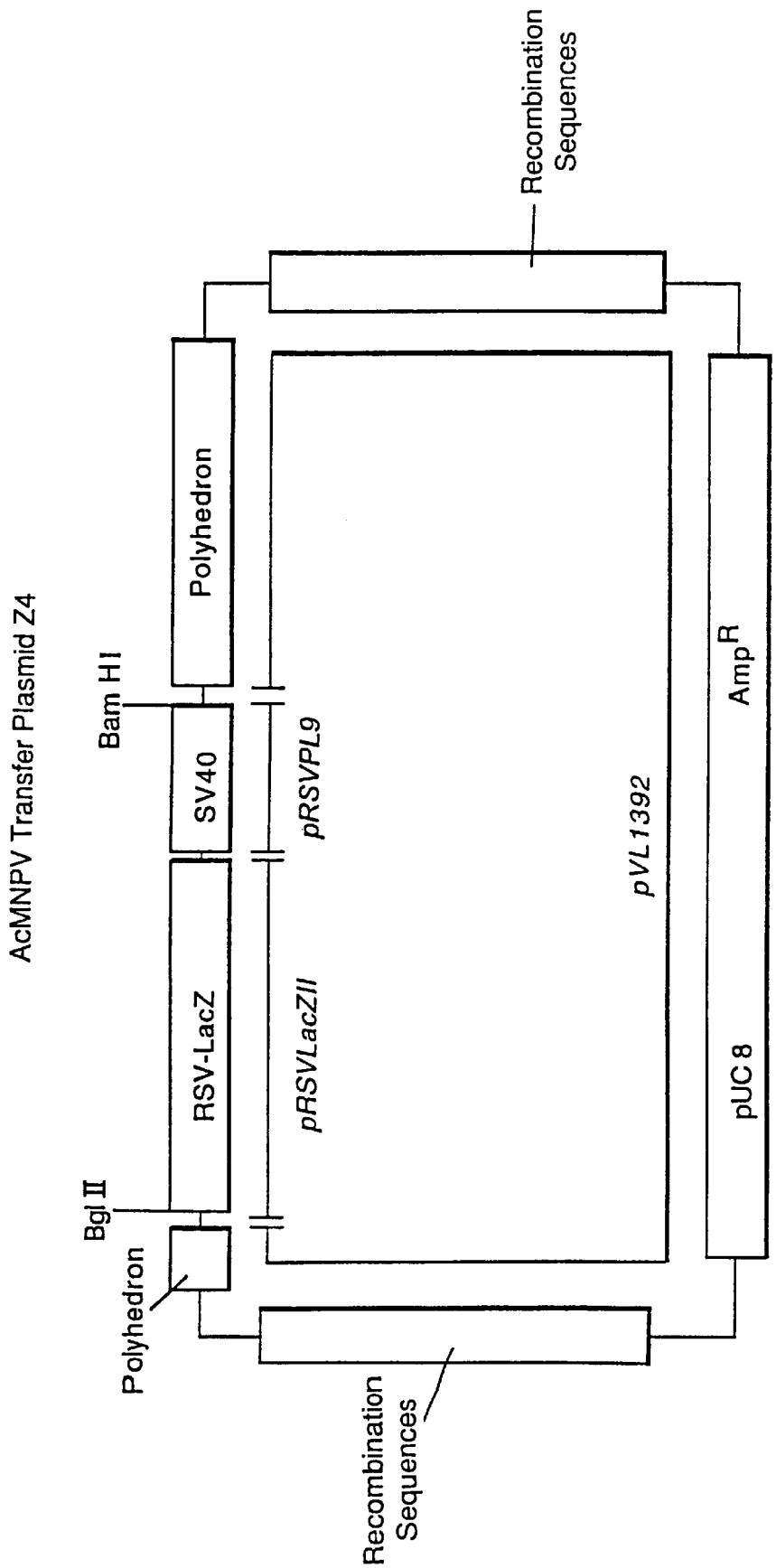
Figure 2:
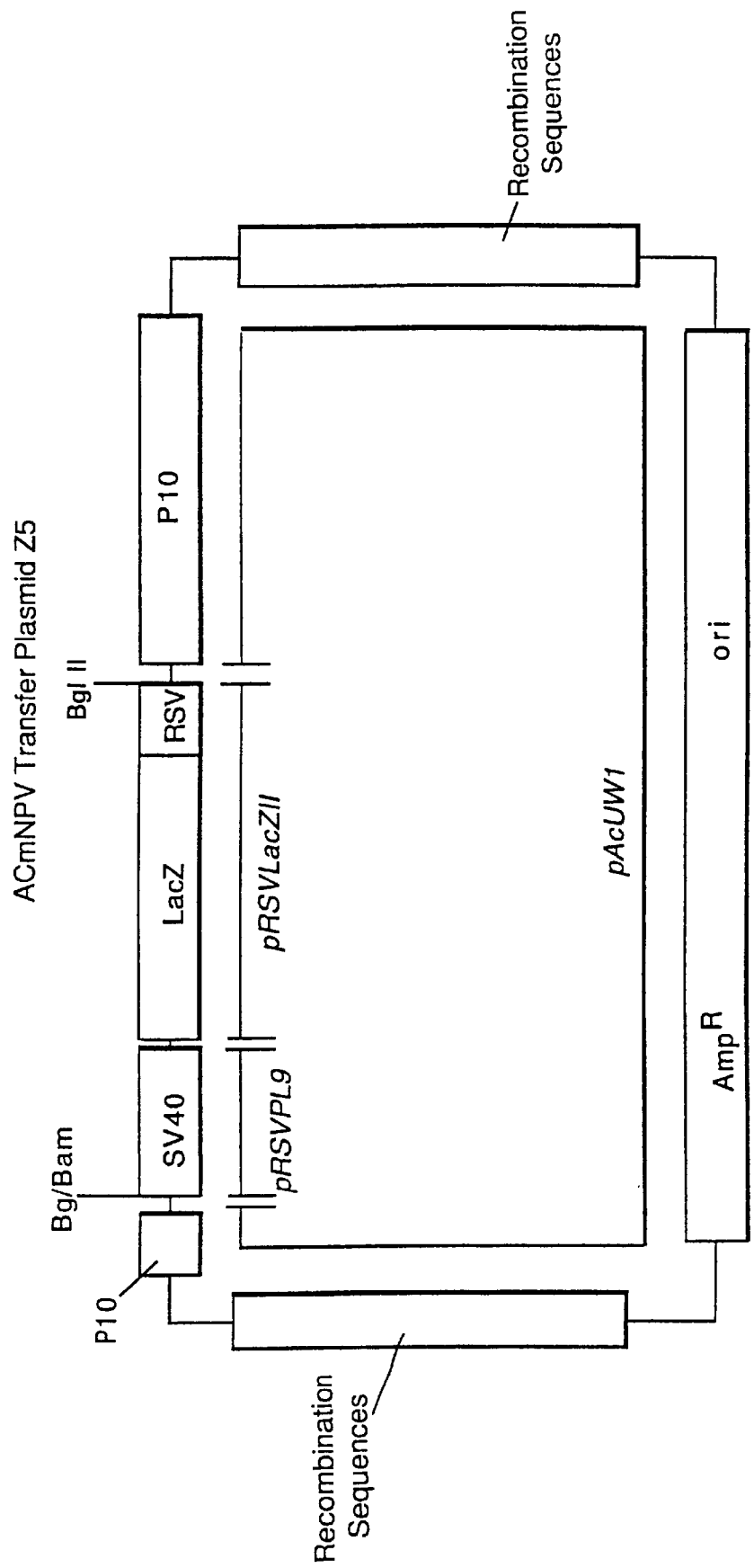

In contrast to conventional gene expression methods, the invention involves modifying non-mammalian DNA viruses that do not naturally infect and replicate in mammalian cells. Thus, the invention is based on the addition of new properties to a non-mammalian DNA virus that allow it to deliver a gene to a mammalian cell and direct gene expression within the mammalian cell. In contrast, conventional gene therapy vectors require that one disable viral functions, such as expression of viral genes and viral genome replication.

In the present method, the viral particle serves as a "shell" for the delivery of DNA to the mammalian cell. The viral DNA is engineered to contain transcriptional control sequences that are active in a mammalian cell, to allow expression of the gene of interest in the target cell. Conventional recombinant DNA techniques can be used for inserting such sequences. Because the non-mammalian DNA viruses used in the invention are not capable of replicating in mammalian cells, it is not necessary to delete essential viral functions to render them defective. It is preferred, however, that the virus naturally replicate in a eukaryotic species (e.g., an insect, a plant, or a fungus). Examples of viruses that can be engineered to express an exogenous gene in accordance with the invention are listed in Table 1. Preferably, the genome of the virus used in the invention is normally transported to the nucleus in its natural host species because nuclear localization signals function similarly in invertebrate and in mammalian cells. The data summarized below show that, in contrast to conventional wisdom, a non-mammalian DNA virus can (1) infect a wide variety of mammalian cells, and (2) direct expression of an exogenous gene in the cells. In addition, expression of an altered coat protein on the surface of a virus particle enhances the ability of the virus to express an exogenous gene in a mammalian cell.

Established methods for manipulating recombinant viruses may be incorporated into these new methods for expressing an exogenous gene in a mammalian cell. For example, viral genes can be deleted from the virus and supplied in trans via packaging lines. Deletion of such genes may be desired in order to (1) suppress expression of viral gene products that may provoke an immune response, (2) provide additional space in the viral vector, or (3) provide additional levels of safety in maintaining the virus in a cell.

This invention involves the expression of an altered coat protein(s) on the surface of virus particle to enhance the ability of a non-mammalian DNA virus to infect a mammalian cell and express an exogenous gene in the mammalian cell. Conventional molecular biology techniques and criteria can be used for identifying and expressing on the virus a polypeptide that binds a mammalian cell. Typically, a gene encoding the altered coat protein is operably linked to a non-mammalian-active promoter, and is expressed from the viral genome. Alternatively, the altered coat protein can be encoded by a sequence contained within a chromosome of a non-mammalian cell in which the virus is propagated. Upon expression of the altered coat protein from the cellular chromosome, the altered coat protein is packaged along with the non-mammalian DNA virus. In yet another alternative method, the altered coat protein can be expressed from the genome of a second virus that co-infects the non-mammalian cell in which the non-mammalian DNA virus is propagated. Thus, upon co-infection and expression of the altered coat protein from the genome of the second virus, the altered coat protein is packaged along with the non-mammalian DNA virus. Regardless of the method used to express the altered coat protein, the non-mammalian DNA virus is maintained under conditions such that the altered coat protein is expressed on the surface of the virus particle. To this end, conventional methods for propagating viruses (further discussed below) in non-mammalian cells can be used. If desired, expression of the altered coat protein on the surface of a virus particle can be confirmed using conventional techniques, such as immunoblotting, immunofluorescence, and the like.

Conventional molecular biology techniques can be used to produce a suitable fusion protein that is used as the altered coat protein. For example, where a baculovirus is used as the non-mammalian DNA virus, a wide variety of fusion proteins can be made employing the baculovirus coat protein gp64 (Whitford et al., 1989, J. Virol. 63:1393–1399 and Ayres et al., 1994, Virology 202:586–605). The baculovirus expression vector pAcSurf-2 provides a gp64 gene having a multiple cloning site positioned in-phase between the gp64 signal sequence and the sequence encoding the mature glycoprotein (Boublik et al., 1995, Biotechnology 13:1079–1084). Sequences encoding a polypeptide that binds a mammalian cell can readily be inserted into the multiple cloning site of this vector, and expression of the resulting fusion protein is driven by the polyhedrin promoter to which the gp64 sequences are operably linked.

If desired, the viral capsid or envelope can contain, as part of the altered coat protein, or as a separate molecule in addition to the altered coat protein, a ligand that binds to mammalian cells to facilitate entry. For example, the virus can include as a ligand an asialoglycoprotein that binds to mammalian lectins (e.g., the hepatic asialoglycoprotein receptor), facilitating entry into mammalian cells.

Because most promoters of non-mammalian viruses are not active in mammalian cells, the exogenous gene should be operably linked to a promoter that is capable of directing gene transcription in a mammalian cell (i.e., a "mammalian-active" promoter). Examples of suitable promoters include the RSV LTR, the SV40 early promoter, CMV IE promoters (e.g., the human CMV IE1 promoter), the adenovirus major late promoter, and the Hepatitis B viral promoter. Other suitable "mammalian-active" promoters include "mammalian promoters," i.e., sequences corresponding to promoters that naturally occur in, and drive gene expression in, mammalian cells. Often, "mammalian promoters" are also cell-type-specific, stage-specific, or tissue-specific in their ability to direct transcription of a gene, and such promoters can be used advantageously in the invention as a means for controlling expression of the exogenous gene. For example, several liver-specific promoters, such as the albumin promoter/enhancer, have been described and can be used to achieve liver-specific expression of the exogenous gene (see, e.g., Shen et al., 1989, DNA 8:101–108; Tan et al., 1991, Dev. Biol. 146:24–37; McGrane et al., 1992, TIBS 17:40–44; Jones et al., J. Biol. Chem. 265:14684–14690; and Shimada et al., 1991, FEBS Letters 279:198–200). Where the invention is used to treat a hepatocellular carcinoma, an α-fetoprotein promoter is particularly useful. This promoter is normally active only in fetal tissue; however, it is also active in liver tumor cells (Huber et al., 1991, Proc. Natl. Acad. Sci. 88:8039–8043). Accordingly, an α-fetoprotein promoter can be used to target expression of a liver-cancer therapeutic to liver tumor cells.

If desired, the virus genome can be engineered to carry an origin of replication in order to facilitate persistence of the exogenous gene in the mammalian cell. Origins of replication derived from mammalian cells (i.e., "mammalian origins of replication," have been identified (Burhans et al., 1994, Science 263:639–640). Other origins of replication that function in mammals (i.e., "mammalian-active" origins, e.g., the Epstein-Barr Virus oriP) can also facilitate maintenance of expression in the presence of appropriate trans-acting factors (e.g., EBNA-1). If desired, the virus can be engineered to express more than one exogenous gene (e.g., the virus can be engineered to express both OTC and AS) or more than one altered coat protein.

Descriptions of several viruses used in the examples described below now follow. These examples are provided for illustrative purposes, and are not meant to limit the scope of invention.

EXAMPLES OF TRANSFER PLASMIDS

Construction of the pZ4 Transfer Plasmid: Genetic manipulation of a baculovirus for use in the invention can be accomplished with commonly-known recombination techniques originally developed for expressing proteins in baculovirus (see, e.g., O'Reilly et al., 1992, In: Baculovirus expression vectors, W. H. Freeman, New York). In this example, an AcMNPV was constructed by interrupting the polyhedrin gene of the virus with a cassette that directs expression of a reporter gene. The reporter gene cassette included DNA sequences corresponding to the Rous Sarcoma Virus (RSV) promoter operably linked to the *E. coli* lacZ gene (FIG. 1). The reporter gene cassette also included sequences encoding Simian Virus 40 (SV40) RNA splicing and polyadenylation signals.

The RSV-lacZ AcMNPV transfer plasmid used in several examples set forth below is named Z4 and was constructed as follows. An 847 bp fragment of pRSVPL9 including the SV40 RNA splicing signal and polyadenylation signal was excised using BglII and BamHI. Plasmid pRSVPL9 was derived from pRSVglobin (Gorman et al., Science 221:551–553) by digesting pRSVglobin with BglII, adding a HindIII linker, and then cleaving the DNA with HindIII. A double-stranded polylinker made by hybridization of the oligonucleotides 5'AGCTGTCGACTCGAGGTACCA-GATCTCTAGA3' (SEQ ID NO: 1) and 5'AGCTTCTA-GAGATCTGGTACCTCGAGTCGAC3' (SEQ ID NO: 2) was ligated to the 4240 bp fragment having the RSV promoter and SV40 splicing and polyadenylation signals. The resulting plasmid has the polylinker in place of the globin sequences. The SV40 sequence of pRSVPL9 was cloned into the BamHI site of pVL1392 (Invitrogen and Pharmingen) using standard techniques. The resulting intermediate plasmid was named pVL/SV40. An RSV-lacZ cassette was excised from pRSVlacZII (Lin et al., 1991, Biotechniques 11:344–348, and 350–351) with BglII and SpeI and inserted into the BglII and XbaI sites of pVL/SV40.

The AcMNPV RSV-lacZ virus, termed Z4, was prepared by homologous recombination of the Z4 transfer plasmid with linearized AcMNPV DNA. The AcMNPV virus used to prepare this DNA was AcV-EPA (Hartig et al., 1992, J. Virol. Methods 38:61–70).

Construction of the pZ5 Transfer Plasmid: Certain non-mammalian viruses (e.g., baculoviruses) may be occluded in a protein inclusion body (i.e., occluded-derived viruses (ODV)), or they may exist in a plasma membrane budded form. Where an occluded virus is used in the invention, the virus may first be liberated from the protein inclusion body, if desired. Conventional methods employing alkali may be used to release the virus (O'Reilly et al., 1992, In: Baculovirus expression vectors, W. H. Freeman, New York). An occluded, alkali-liberated baculovirus may be taken up by a cell more readily than is the non-occluded budded virus (Volkman and Goldsmith, 1983, Appl. and Environ. Microbiol. 45:1085–1093). To construct the pZ5 transfer plasmid (FIG. 2), for using an occluded virus in the invention, the RSV-lacZ cassette was excised from the pZ4 transfer plasmid using BglII and BamHI and then inserted into the BglII site of pAcUW1 (Weyer et al., 1990, J. Gen. Virol. 71:1525–1534).

Figure 3:
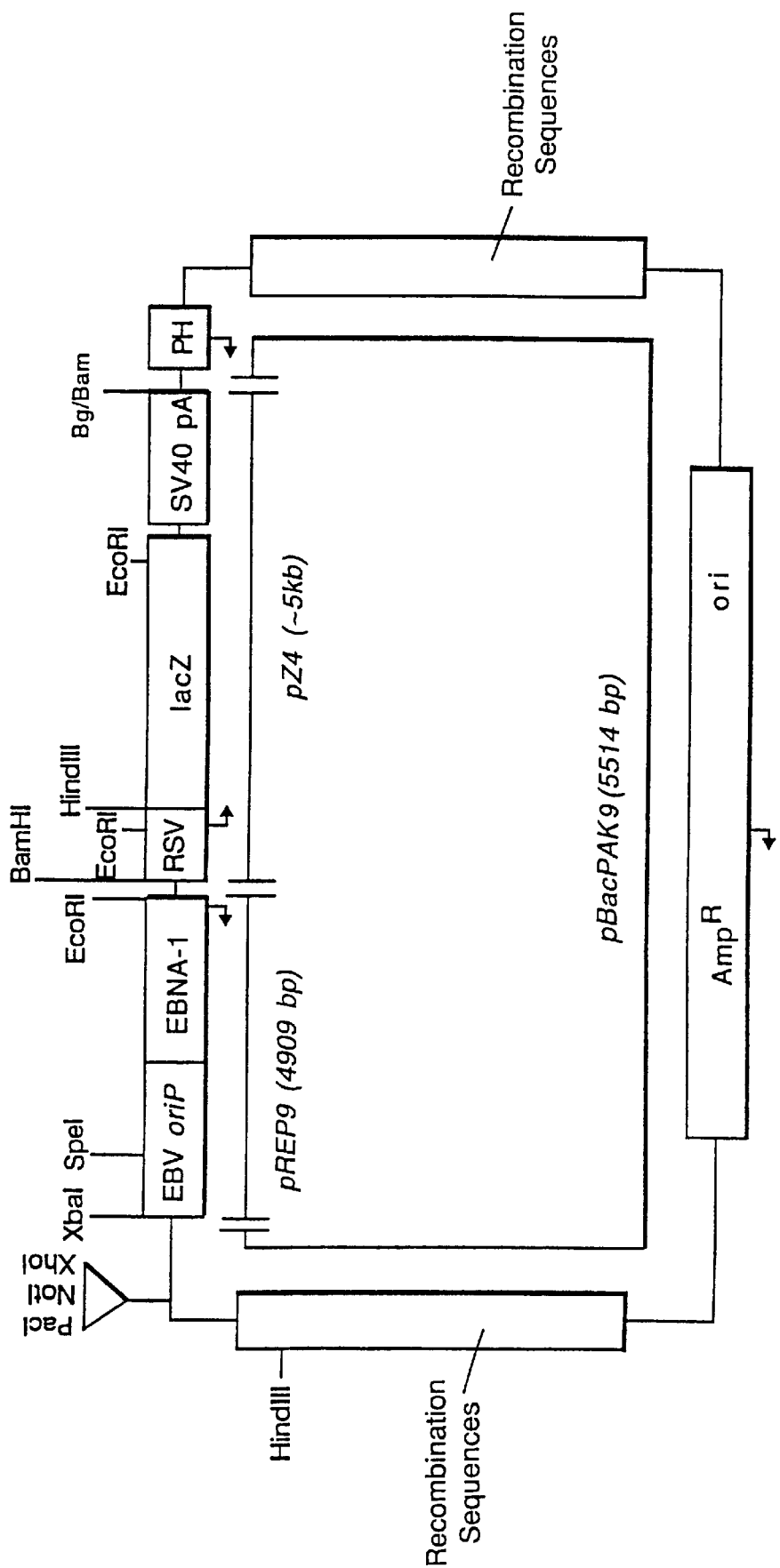

Construction of the pZ-EBV#1 Transfer Plasmid: The non-mammalian DNA viruses used in the invention may be engineered to permit episomal replication of the virus in the mammalian cell. Such a virus would persist longer, thereby optimizing methods for long-term expression of an exogenous gene in a cell. An example of such a replicating virus is pZ-EBV#1 (FIG. 3), which was constructed as follows. The EBV oriP and EBNA-1 region was excised from pREP9 (Invitrogen) using EcoRI and XbaI and then inserted into the baculoviral transfer plasmid pBacPAK9 (Clontech) at its EcoRI and XbaI sites, yielding pEBVBP9. The RSV-lacZ cassette was excised from transfer plasmid Z4 with BglII and BamHI and then inserted into the BamHI site of pEBVBP9 to yield the plasmid pZ-EBV#1.

Construction of pZ4loxP: The Z4loxP viral genome is a substrate for recombination with bacteriophage P1 cre recombinase. This virus can be used to insert gene cassettes bearing a loxp site into the virus using standard procedures (Patel et al., 1992, Nucl. Acids Res. 20:97–104). A variation of this insertion system may be engineered so that the viral sequences are excised from the remaining gene expression sequences. For example, an auto-excising transfer plasmid may be constructed (FIGS. 4A–4B) to express an exogenous gene in a mammalian cell. This plasmid contains loxp sequences which facilitate excision of the baculoviral sequences. The pZ4loxP transfer plasmid was constructed by inserting a synthetic loxp site into the pZ4 transfer plasmid. Two loxp oligonucleotides were synthesized and annealed to each other. The oligonucleotides were:

5'GATCTGACCTAATAACTTCGTATAGCATACAT TATACGAAGTTATATTAAGG3' (SEQ ID NO: 3) and

5'GATCCCTTAATATAACTTCGTATAATGTATGC TATACGAAGTTATTAGGTCA3' (SEQ ID NO:4).

The oligonucleotides were annealed by heating them to 80° C. in the presence of 0.25 M NaCl and then allowing the mixture to cool slowly to room temperature before use in the ligation reactions. The annealed oligonucleotides were then ligated to the pZ4 transfer plasmid that had been digested with BglII. The ligations and analysis of the resulting clones were performed with standard cloning techniques. Recombinant Z4loXP baculovirus was then generated with conventional methods for recombination into linear baculoviral DNA.

Figure 5:
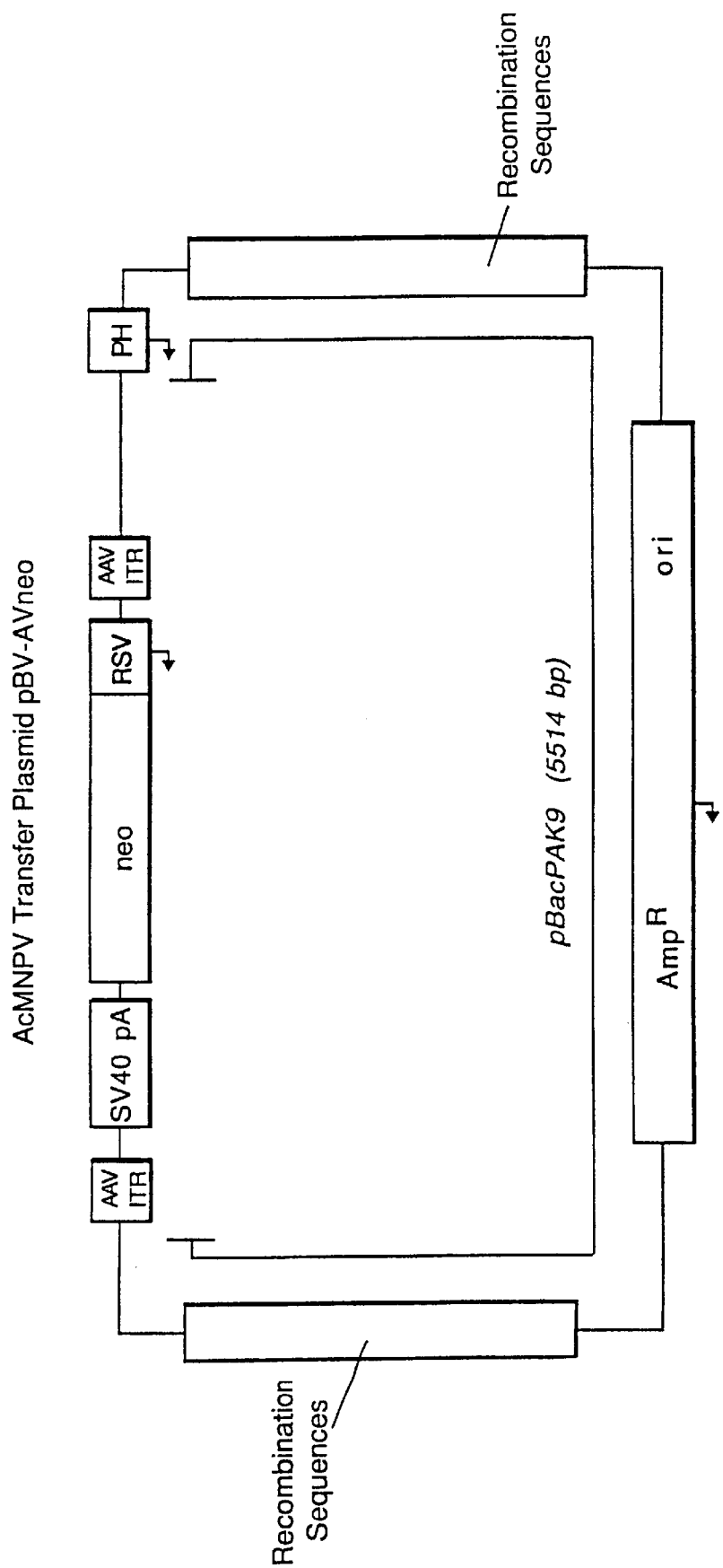

Construction of pBV-AVneo, an AAV Chimera Transfer Plasmid: A baculovirus genome that is capable of integrating into a chromosome of the host cell can also be used in the invention. Such an integrated virus may persist in the cell longer than a non-integrated virus. Accordingly, methods of gene expression involving such viruses may obviate the need for repeated administration of the virus to the cell, thereby decreasing the likelihood of mounting an immune response to the virus. The transfer plasmid pBV-AVneo (FIG. 5) includes the inverted terminal repeats of an Adeno-associated virus (AAV). This transfer plasmid was constructed by excising the neo gene, which encodes G418-resistance, as a BglII-BamHI fragment from pFasV.neo and inserting the fragment into the BamHI site of pAVgal in place of the lacZ gene. Plasmid pAVgal was constructed by replacing the rep and cap coding sequences of AAV with a CMV promoter and a lacZ gene. The resulting intermediate fragment, termed pAV.neo, was digested with PvuI. The large PvuI fragment, which has the CMV promoter driving expression of the neo gene, flanked by the AAV ITRs, then was inserted into the PacI site of pBacPAK9. If desired, a suitable promoter operably linked to an AAV rep gene may be inserted into this construct (e.g., between the AAV ITR and the polyhedrin promoter) to facilitate excision and recombination into the genome. Examples of rep genes that may be inserted into this construct include rep40, rep52, rep68, and rep78.

Figure 6:
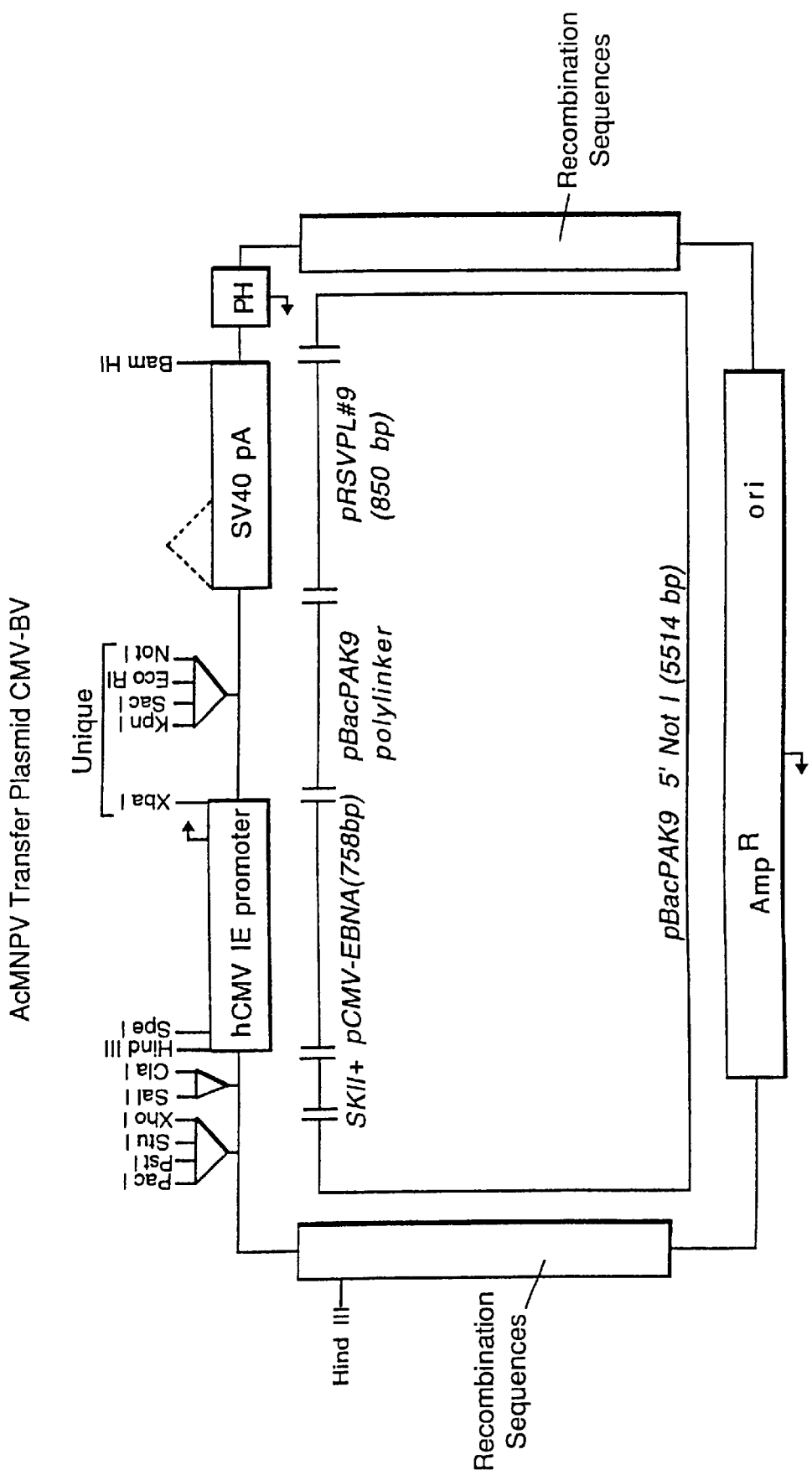

Construction of the pCMV-BV Transfer Plasmid: The human cytomegalovirus immediate early promoter, a 758 bp HindIII-XbaI fragment, was excised from pCMV-EBNA (Invitrogen) at HindIII, BamHI and inserted into the HindIII sites of pBluescript (SKII$^+$), yielding plasmid pCMV-SKII$^+$. The promoter was then excised from CMV-SKII$^+$ at the XhoI, BamHI sites and inserted into the XhoI, BglII sites of pSV/BV, yielding plasmid pCMV-BV (FIG. 6). pSV/BV is a modified version of the baculovirus transfer plasmid pBacPAK9 (Clontech), containing an altered polylinker and SV40 splice and polyadenylation signals. pSV/BV was constructed by restriction of pBacPAK9 with NotI, treatment with T4 DNA polymerase to create blunt ends, and self-ligation to remove the NotI site. A new NotI site was then added by ligation of the linker pGCGGCCGC into the SmaI site. Finally, SV40 splice and polyadenylation sequences were added by digestion of pRSVPL with BglII-BamHI, and insertion of the 847 bp fragment into the BamHI site of the modified BacPAK9, yielding pSV/BV.

Figure 7:
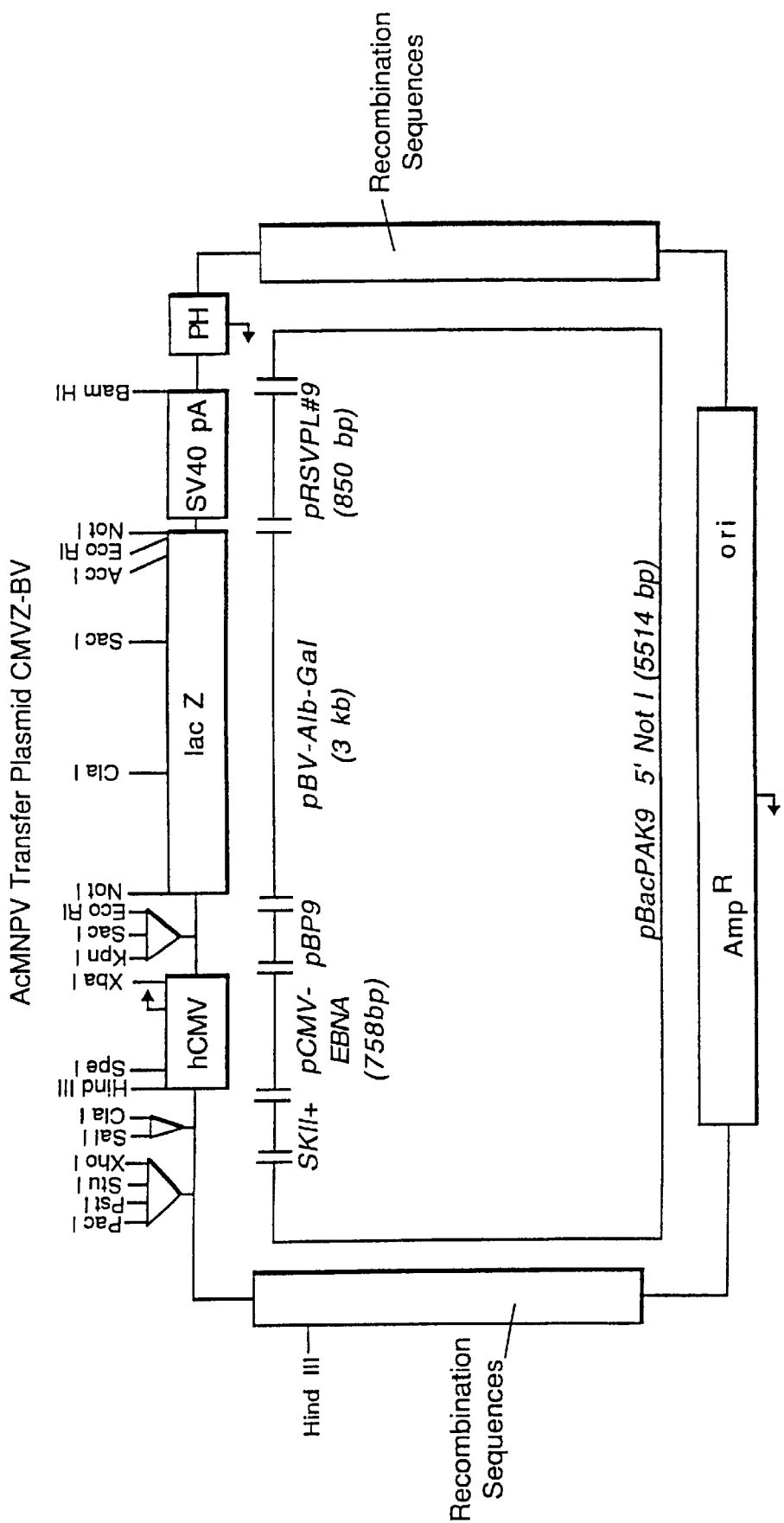

Construction of the pCMVZ-BV Transfer Plasmid: pCMVZ-BV (FIG. 7) was constructed by restriction of pCMV-BV with NotI and ligation insertion of a 3 kb lacZ fragment. The lacZ fragment was prepared by restriction of pAlb-Gal with NotI.

Figure 8:
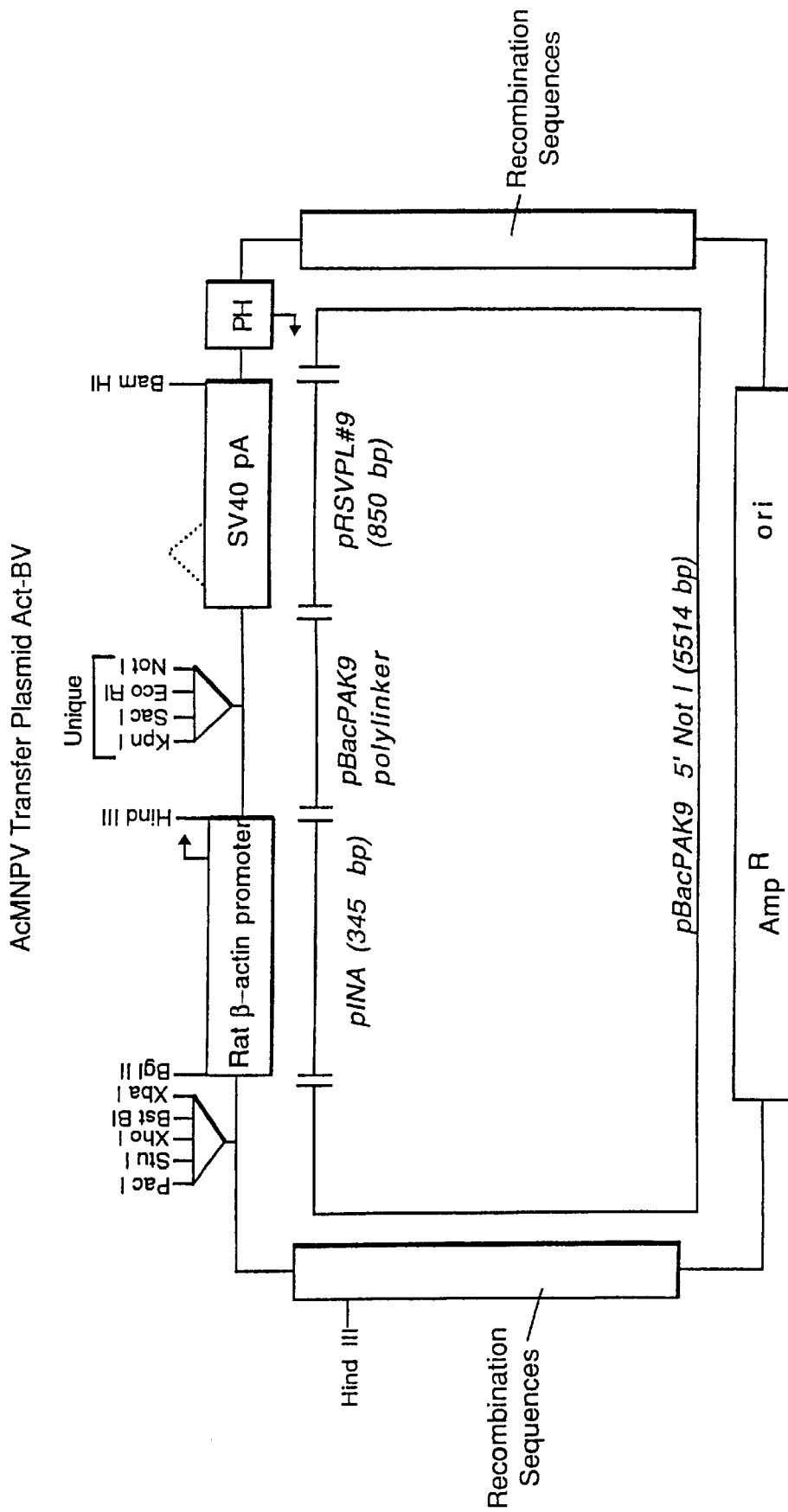

Construction of the pAct-BV Transfer Plasmid: The 345 bp rat β-actin promoter was excised from pINA (Morgenstern, J. P., 1989, Ph.D. Thesis, University College, London, UK) at BglII, BamHI and inserted into the BglII site of pSV/BV, yielding pAct-BV (FIG. 8).

Figure 9:
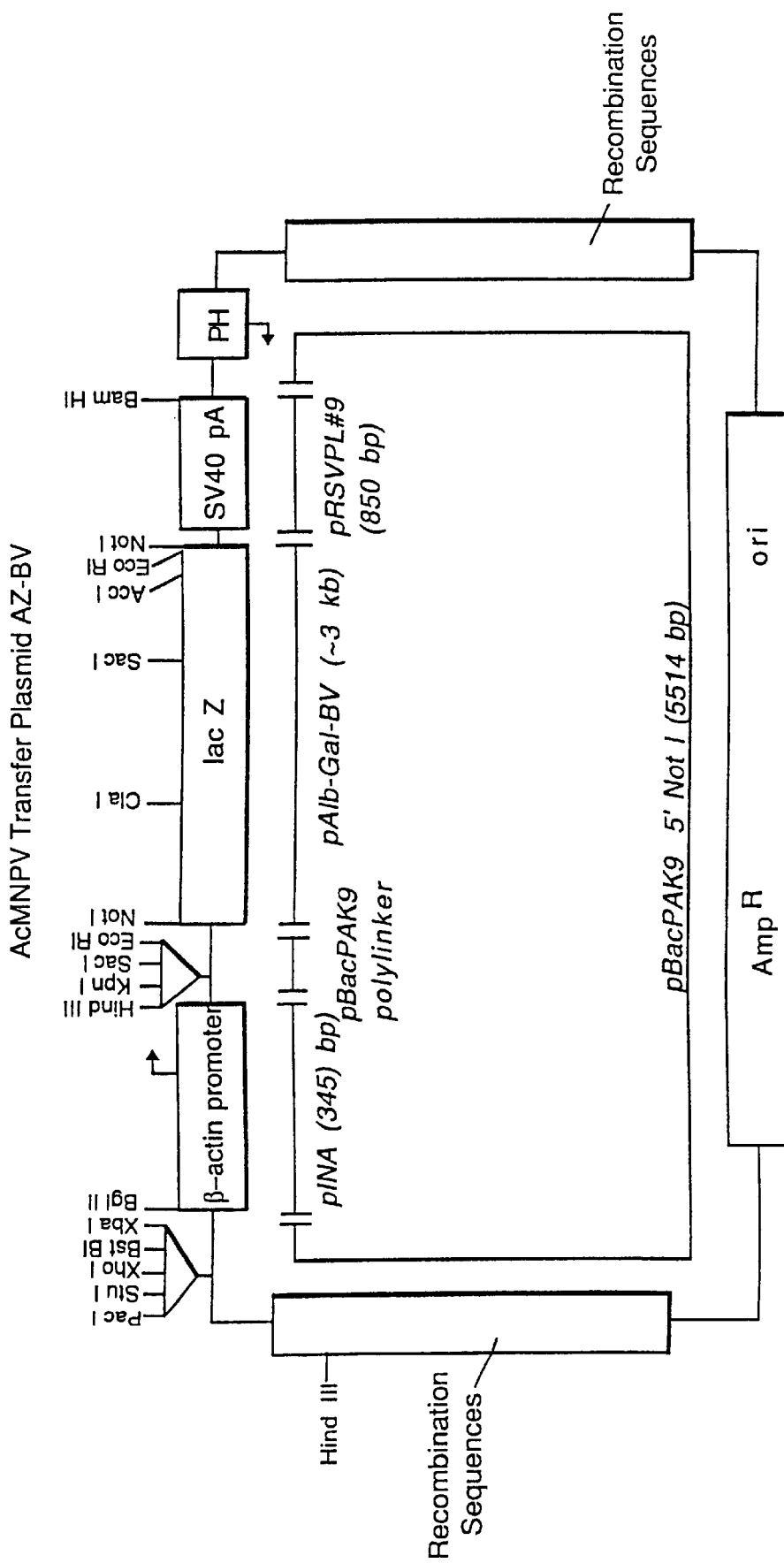

Construction of the pAZ-BV Transfer Plasmid: pAZ-BV (FIG. 9) was constructed by restriction of pAct-BV with NotI and ligation insertion of a 3 kb lacZ fragment. The lacZ fragment was prepared by restriction of pAlb-Gal with NotI.

Figure 10:
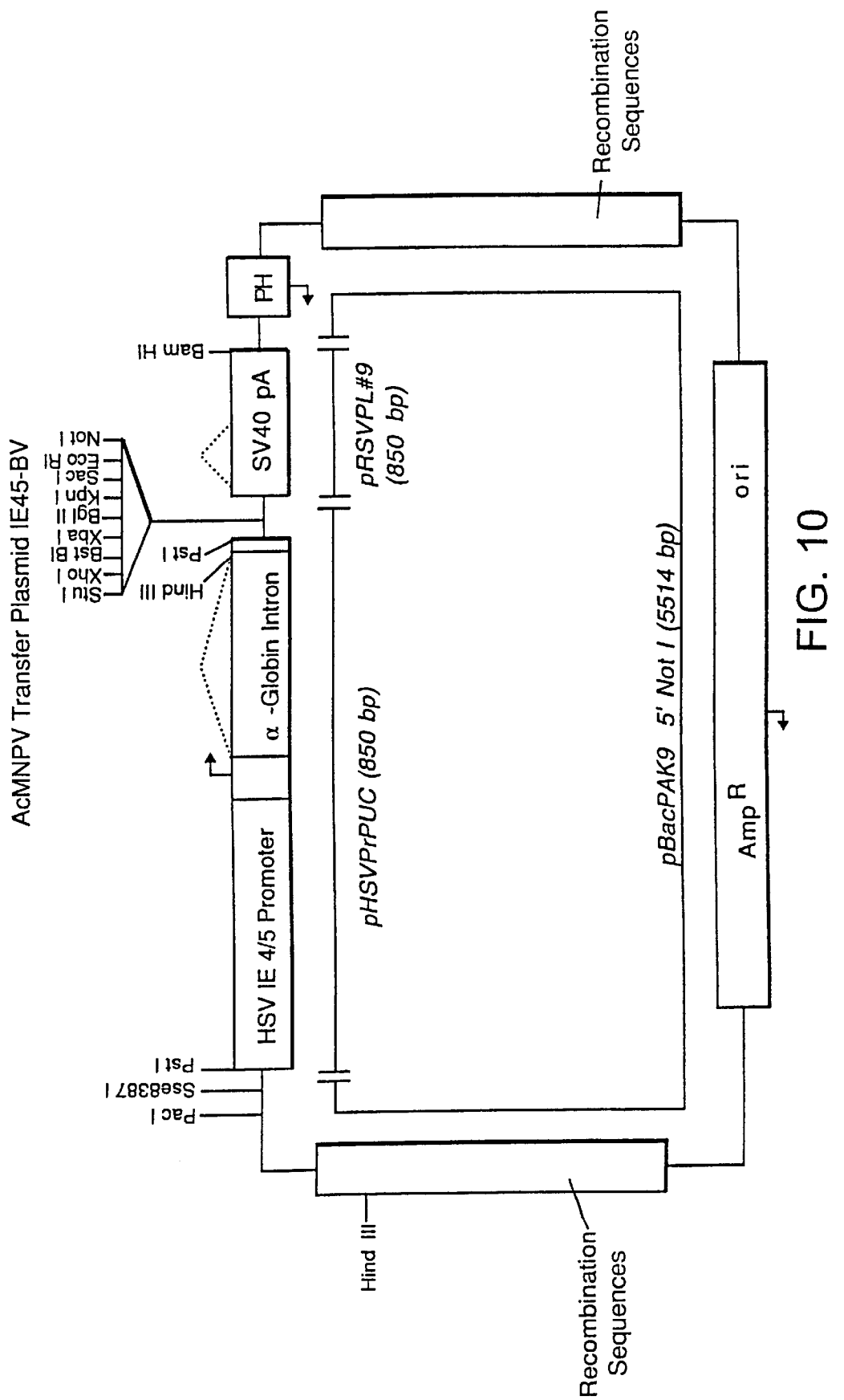

Construction of the pIE45-BV Transfer Plasmid: pIE45-BV (FIG. 10) was constructed by restriction of pHSVPrPUC (Neve et al., 1997, Neuroscience 79:435–447) with SphI, followed by treatment with T4 DNA polymerase in the presence of nucleotide triphosphates to create blunt ends. PstI linkers (New England Biolabs, Catalog #1024, PGCTGCAGC) were then added by treatment with T4 DNA ligase, the fragment of approximately 850 bp was subjected to digestion with PstI, and cloned into the PstI site of pSV/BV.

Figure 11:
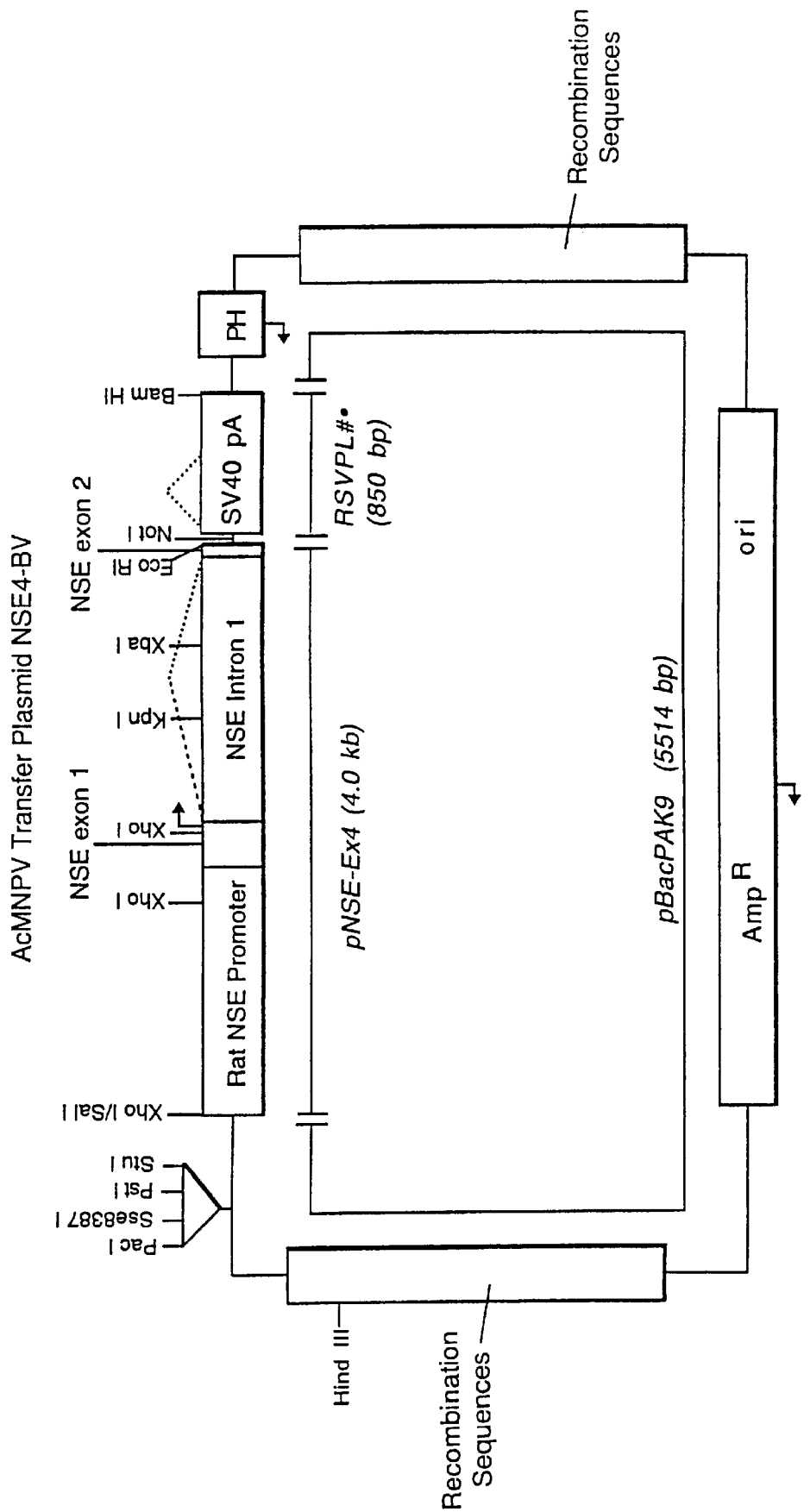
FIG. 11 is a schematic representation of the AcMNPV transfer plasmid pNSE4-BV.

Construction of the pNSE4-BV Transfer Plasmid: pNSE4-BV (FIG. 11) was constructed by restriction of pNSE4 (see, e.g., Quon et al., 1991, Nature 352::239–241 and Forss-Petter et al., 1990, Neuron 5:187–197) with SalI and EcoRI, followed by ligation into the XhoI and EcoRI sites of pSV/BV.

Figure 12:
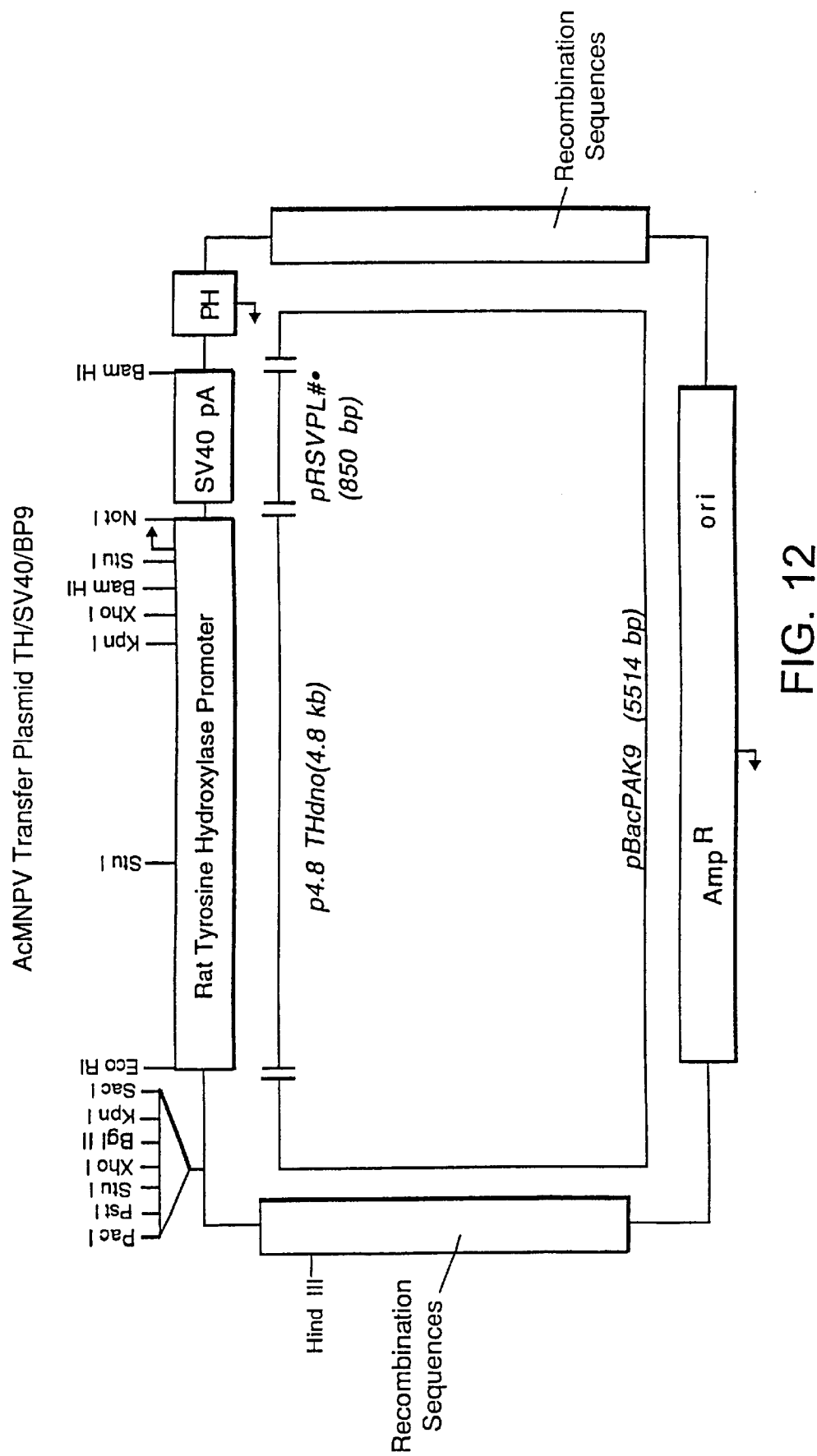
FIG. 12 is a schematic representation of the AcMNPV transfer plasmid pTH/SV40/BP9.

Construction of the pTH/SV40/BP9 Transfer Plasmid: p-TH/SV40/BP9 (FIG. 12) was constructed by restriction of pTH4.8 Thdno (Banerjee et al., 1992, J. Neuroscience 12:4460–4467) with EcoRI and NotI, and ligation of the 4.0 kb promoter fragment into pSV/BV, which was also digested with EcoRI and NotI.

Figure 13:
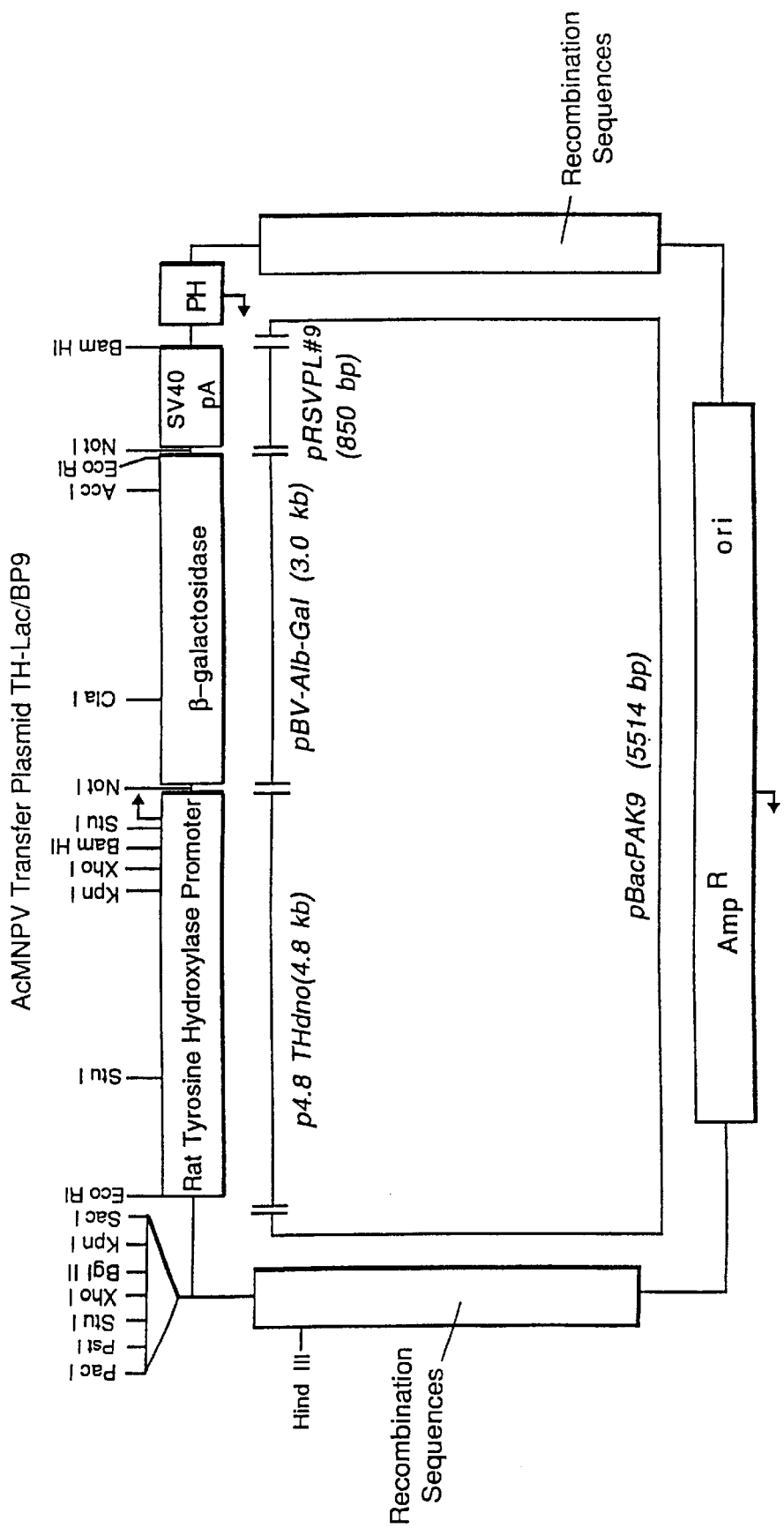
FIG. 13 is a schematic representation of the AcNPV transfer plasmid pTH-Lac/BP9.

Construction of the pTH-Lac/BP9 Transfer Plasmid: pTh-lac (FIG. 13) was constructed by restriction of pALB-Gal with Not I and isolation of the 3 kb lacZ fragment, which was then ligated into pTH/SV40/BP9 which was also restricted with Not I using T4 DNA ligase.

Propagation of Viruses: Conventional methods can be used to propagate the viruses used in the invention (see, e.g., Burleson, et al., 1992, Virology: A Laboratory Manual, Academic Press, Inc., San Diego, Calif. and Mahy, ed., 1985, Virology: A Practical Approach, IRL Press, Oxford, UK). Conventional conditions for propagating viruses are suitable for allowing expression of an altered coat protein on the surface of a virus particle used in the invention. For example, the baculoviruses used in the experiments described below were plaque purified and amplified according to standard procedures (see, e.g., O'Reilly et al. infra and Summers and Smith, 1987, A Manual of Methods for Baculovirus Vectors and Insect Cell Culture Procedures, Texas Agricultural Experiment Station Bulletin No. 1555, College Station, Texas). AcMNPV and Sf21 cells were propagated by spinner culture in Hinks TNM-FH media (JRH Biosciences) containing 10% fetal bovine serum (FBS) and 0.1% PLURONIC F-68™. Amplified virus can be concentrated by ultracentrifugation in an SW28 rotor (24,000 rpm, 75 minutes) with a 27% (w/v) sucrose cushion in 5 mM NaCl, 10 mM Tris pH 7.5, and 10 mM EDTA. The viral pellet is then resuspended in phosphate-buffered saline (PBS) and sterilized by passage through a 0.45 $\mu$m filter (Nalgene). If desired, the virus may be resuspended by sonication in a cup sonicator. AcMNPV was titered by plaque assay on Sf21 insect cells.

EXAMPLES OF EXOGENOUS GENE EXPRESSION

Because non-mammalian DNA viruses were long thought not to be capable of infecting and directing gene expression in mammalian cells, Part A of the Examples below provides evidence that a non-mammalian DNA virus (e.g., a baculovirus) can, in fact, be used to express an exogenous gene in a mammalian cell. Although the examples described in Part A employ viruses in which the protein coat was not altered, these examples provide support for the assertions that a non-mammalian DNA virus can be used to express an exogenous gene in a mammalian cell. In addition, these examples provide guidance for practicing the invention with a virus having an altered coat protein.

The examples in Part B, below, utilize non-mammalian DNA viruses that have an altered coat protein. Because the presence of the altered coat protein is the only significant difference between the viruses of the invention and the viruses that lack an altered coat protein, these examples demonstrate that the expression of the altered coat protein enhances the ability of a non-mammalian DNA virus to express an exogenous gene in a mammalian cell. Accordingly, in each of the methods described below (e.g., in vivo expression of an exogenous gene), the viruses having an altered coat protein are expected to be superior to the viruses lacking the altered coat protein.

PART A: A NON-MAMMALIAN DNA VIRUS CAN BE USED TO EXPRESS AN EXOGENOUS GENE IN A MAMMALIAN CELL

I. Examples of Expression of an Exogenous Gene in Mammalian Cells In Vitro

Nearly all mammalian cells are potential targets of non-mammalian viruses, and any cultured or primary cell can rapidly be tested. In the following example, the ability of the Z4 baculovirus to infect 19 different types of cells was tested. In this example, the baculovirus was the Z4 virus, prepared by homologous recombination of the Z4 transfer plasmid with linearized AcMNPV DNA. The tested cells were HepG2, Sk-Hep-1, NIH3T3, NIH3T3 cells expressing a cell-surface asialoglycoprotein receptor, HeLa, CHO/dhfr$^-$, 293, COS, Ramos, Jurkat, HL60, K-562, $C_2C_{12}$ myoblasts, $C_2C_{12}$ myotubes, primary human muscle myoblasts, Hep3B cells, FTO2B cells, Hepal-6 cells, and nerve growth factor-differentiated PC12 cells.

Growth of Cells: Conventional tissue culture methods can be used to grow mammalian cells to be infected (Freshney, 1987, Culture of Animal Cells: A Manual of Basic Techniques, 2nd ed., Alan R. Liss, Inc. New York, N.Y.). These cells were grown and infected as is described above. The cells were grown as follows. HepG2 and Sk-Hep-1 cells were cultured in minimal essential medium as modified by Eagle (EMEM) containing 10% FBS. NIH3T3, HeLa, 293, and COS cells were cultured in DMEM containing 10% FBS. CHO/dhfr$^-$ cells were cultured in MEM alpha containing 10% FBS. Ramos, Jurkat, HL60, and K-562 cells were cultured in RPMI 1640 medium containing 10% FBS. HL60 cells were induced to differentiate by culture in the same medium containing 0.5% dimethyl sulfoxide and 1 $\mu$M retinoic acid (Sigma). $C_2C_{12}$ myoblasts were propagated in DMEM containing 20% FBS and differentiated to myotubes during culture in DMEM containing 10% horse serum. PC12 cells were propagated in DMEM containing 5% FBS and 10% horse serum, and were induced to differentiate during culture in DMEM containing 10% FBS, 5% horse serum, and 100 ng/ml nerve growth factor. All cells were seeded one day prior to infection with AcMNPV, and multiplicities of infection were calculated assuming a doubling in cell number during this time. The $C_2C_{12}$ and PC12 cells may have increased in cell number during differentiation, and therefore reflect a somewhat lower moi.

In vitro Infection of Cells: In vitro infection of mammalian cells with a virus can be accomplished by allowing the virus to adsorb onto the cells for 0.1 to 6 hours; preferably, adsorption proceeds for 1 to 2 hours. Generally, a multiplicity of infection of 0.1 to 1,000 is suitable; preferably, the moi is 100 to 500. For relatively refractory cells, a moi of 100 to 1,000 is preferable. For the viruses used in the invention, the titer may be determined with conventional methods which employ the non-mammalian cells that the virus naturally infects. If desired, the mammalian cell to be infected may be maintained on a matrix that contains collagen (e.g., rat tail Type I collagen). Based on cell counting after culture and infection of cells on collagen-coated plates and comparison with cells grown on a conventional EHS matrix, I have found that a collagen matrix increases the susceptibility of cells (e.g., liver cells) to infection by a non-mammalian virus by 10 to 100 fold, relative to a conventional EHS matrix. Commercially-available plates containing a collagen matrix are available (e.g., BIO-COAT™ plates, Collaborative Research), and rat tail collagen is also commercially available (Sigma Chemical and Collaborative Research).

In the in vitro assays described below, standard conditions for infection utilized 2×10$^6$ cells and RSV-lacZ AcMNPV at a moi of 15. Adherent cell lines were seeded one day prior to infection. Cells were exposed to virus in 2 ml of medium for 90 minutes, and then the virus-containing medium was removed and replaced with fresh medium. Mock-infected cells were treated with 2 ml medium lacking the viral inoculum.

Detection of Infection and Gene Expression: Delivery of a virus to a cell and expression of the exogenous gene can be monitored using standard techniques. For example, delivery of a virus (e.g., AcMNPV) to a cell can be measured by detecting viral DNA or RNA (e.g., by Southern or Northern blotting, slot or dot blotting, or in situ hybridization, with or without amplification by PCR). Suitable probes that hybridize to nucleic acids of the virus, regulatory sequences (e.g., the promoter), or the exogenous gene can be conveniently prepared by one skilled in the art of molecular biology. Where the invention is used to express an exogenous gene in a cell in vivo, delivery of the virus to the cell can be detected by obtaining the cell in a biopsy. For example, where the invention is used to express a gene in a liver cell(s), a liver biopsy can be performed, and conventional methods can be used to detect the virus in a cell of the liver.

Expression of an exogenous gene in a cell of a mammal can also be followed by assaying a cell or fluid (e.g., serum) obtained from the mammal for RNA or protein corresponding to the gene. Detection techniques commonly used by molecular biologists (e.g., Northern or Western blotting, in situ hybridization, slot or dot blotting, PCR amplification, SDS-PAGE, immunostaining, RIA, and ELISA) can be used to measure gene expression. If desired, a reporter gene (e.g., lacz) can be used to measure the ability of a particular baculovirus to target gene expression to certain tissues or cells. Examination of tissue can involve: (a) snap-freezing the tissue in isopentane chilled with liquid nitrogen; (b) mounting the tissue on cork using O.C.T. and freezing; (c) cutting the tissue on a cryostat into 10 $\mu$m sections; (d) drying the sections and treating them with 4% paraformaldehyde in PBS, followed by rinsing in PBS; (e) staining the tissue with X-gal (0.5 mg/ml)/ ferrocyanide (35 nM)/ ferricyanide (35 mM) in PBS; and (f) analyzing the tissue by microscopy.

To measure expression of the reporter gene in the infected cells, colorimetric assays of $\beta$-galactosidase enzymatic activity were performed with standard methods (Norton et al., 1985, Molecular & Cellular Biology 5:281–290). Other conventional methods for measuring $\beta$-galactosidase activity could be used in lieu of the methods employed in this example. Cell extracts were prepared at one day post-infection. Cell monolayers were rinsed three times with PBS, scraped from the dish, and collected by low-speed centrifugation. The cell pellets were resuspended in 25 mM Tris pH 7.4/0.1 mM EDTA and then subjected to three cycles of freezing in liquid nitrogen and thawing in a 37° C. water bath. The extracts were then clarified by centrifugation at 14,000× g for 5 minutes. Standard conditions for assaying $\beta$-galactosidase activity utilized 0.1 ml of cell extract, 0.8 ml of PM-2 buffer, and 0.2 ml of o-nitrophenyl-$\alpha$-D-galactopyranoside (4 mg/ml) in PM-2 buffer for 10 minutes at 37° C. (Norton et al., 1985, Mol. & Cell. Biol. 5:281–290). The reaction was stopped by the addition of 0.5 ml of 1 M sodium carbonate. The amount of substrate hydrolyzed was detected spectrophotometrically at 420 nm, and $\beta$-galactosidase enzymatic activity was calculated with conventional methods (Norton et al., 1985, Mol. & Cell. Biol. 5:281–290). The assay was verified to be linear with respect to extract concentration and time. Extract protein concentrations were determined using the Coomassie Plus protein assay (Pierce) with bovine serum albumin as a standard, and the level of $\beta$-galactosidase activity was expressed as units of $\beta$-galactosidase activity per mg of protein. Other standard protein assays can be used, if desired.

For histochemical staining of $\beta$-galactosidase activity, cells were fixed in 2% (w/v) formaldehyde-0.2% (v/v) paraformaldehyde in PBS for 5 minutes. After several rinses with PBS, the cells were stained by the addition of 0.5 mg/ml of X-gal (BRL) in PBS for 2–4 hours at 37° C.

Assay of 19 Mammalian Cell Types: The following 19 examples illustrate that expression of an exogenous gene can be detected in 14 of the 19 mammalian cell types that were tested. These assays employed two different tests of $\beta$-galactosidase activity. By X-gal staining, the more sensitive assay, exogenous gene expression was detected in 14 of the 19 mammalian cell types. Using an ONPG assay of cell extracts, which is a less sensitive assay, three of the cell lines (HepG2, 293, and PC12) showed statistically significant ($P<0.05$, Student's t-test) higher $\beta$-galactosidase activity after exposure to the virus (Table 3). The human liver tumor line HepG2 exposed to the RSV-lacZ baculovirus expressed greater than 80-fold higher levels of $\beta$-galactosidase than did mock-infected controls. The adenovirus-transformed human embryonal kidney cell line 293 expressed the lacZ reporter gene at a level of about four-fold over background. In addition, PC12 cells, which were differentiated to a neuronal-like phenotype with nerve growth factor, exhibited about two-fold higher P-galactosidase levels after infection with the RSV-lacZ baculovirus. This difference was statistically significant ($P=0.019$).

TABLE 3

BACULOVIRUS-MEDIATED EXPRESSION OF AN RSV-LACZ REPORTER GENE IN MAMMALIAN CELL LINES.

| | $\beta$-galactosidase activity (units/mg) Mean ± SD | |
| --- | --- | --- |
| Cell Line | Mock Infected | RsV-lacZ Virus |
| HepG2 | 0.030 ± 0.004 | 2.628 ± 0.729 |
| Sk-Hep-1 | 0.019 ± 0.003 | 0.019 ± 0.004 |
| NIH3T3 | 0.026 ± 0.003 | 0.023 ± 0.005 |
| HeLa | 0.034 ± 0.009 | 0.036 ± 0.005 |
| CHO/dhfr- | 0.020 ± 0.002 | 0.026 ± 0.005 |
| 293 | 0.092 ± 0.014 | 0.384 ± 0.024 |
| COS | 0.029 ± 0.002 | 0.032 ± 0.007 |
| Ramos | 0.008 ± 0.002 | 0.011 ± 0.004 |
| Jurkat | 0.012 ± 0.004 | 0.007 ± 0.001 |
| HL60 | 0.042 ± 0.039 | 0.014 ± 0.015 |
| K-562 | 0.018 ± 0.006 | 0.017 ± 0.002 |
| $C_2C_{12}$ myoblast | 0.015 ± 0.001 | 0.014 ± 0.003 |
| $C_2C_{12}$ myotube | 0.049 ± 0.011 | 0.042 ± 0.004 |
| PC12 (+NGF) | 0.019 ± 0.005 | 0.033 ± 0.004 |

By histochemical staining, a more sensitive assay, $\beta$-galactosidase activity was detected in 14 of the 19 cell lines exposed to virus. Thus, certain of the cell lines that did not yield statistically significantly higher levels of $\beta$-galactosidase, as measured in extracts, were, in fact, able to express $\beta$-galactosidase at low, but reproducible, frequencies, as detected by the more sensitive X-gal staining procedure. This frequency could be increased by using higher multiplicities of infection such that cells that, at a low moi appear not to express the gene, stain blue at a higher moi. Examples of cell lines that could be transfected in this manner include SK-Hep-1, NIH3T3, HeLa, CHO/dhfr⁻, 293, Cos, and $C_2C_{12}$ cells. In addition, $\beta$-galactosidase activity was detected in primary human muscle myoblasts that were exposed to virus. This finding indicates that baculovirus was able to mediate gene transfer both to primary cells and the corresponding established cell line ($C_2C_{12}$), indicating that expression of the exogenous gene in an established cell line has predictive value for the results obtained with primary cells. β-galactosidase activity was also detected in Hep3B cells treated with the virus; the level of expression in these cells was nearly equivalent to the level detected with HepG2 cells. In addition, β-galactosidase activity was found in FTO2B (rat hepatoma) cells and Hepal-6 (human hepatoma) cells exposed to virus. -galactosidase activity was also detected in NIH3T3 cells that were engineered to express the asialoglycoprotein receptor on the cell surface. These cells expressed approximately two times the level of β-galactosidase as did normal NIH3T3 cells. This observation suggests that an asialoglycoprotein receptor may be used to increase susceptibility to viral-mediated gene transfer.

At the moi employed, the Ramos, Jurkat, HL60, and K-562 cell lines did not express statistically significant levels of β-galactosidase, as revealed by β-galactosidase enzyme assays after infection. Based on the results with other mammalian cell lines, it is expected that β-galactosidase activity would be detected in these apparently refractory cell lines when a higher dose (i.e., moi) of virus or longer adsorption time period is utilized.

Even when exposure of cells to the virus results in expression of the exogenous gene in a relatively low percentage of the cells (in vitro or in vivo), the invention can be used to identify or confirm the cell- or tissue-type specificity of the promoter that drives expression of the exogenous gene (e.g., a reporter gene such as a chloramphenicol acetyltransferase gene, an alkaline phosphatase gene, a luciferase gene, or a green fluorescent protein gene). Once identified, such a promoter may be employed in any of the conventional methods of gene expression. Similarly, only relatively low levels of expression are necessary for provoking an immune response (i.e., produce antibodies) in a mammal against the heterologous gene product. Thus, the gene expression method of the invention can be used in the preparation of antibodies against a preferred heterologous antigen by expressing the antigen in a cell of a mammal. Such antibodies may be used inter alia to purify the heterologous antigen. The gene expression method may also be used to elicit an immunoprotective response in a mammal (i.e., be used as a vaccine) against a heterologous antigen. In addition, the invention can be used to make a permanent cell line from a cell in which the virus mediated expression of a cell-immortalizing sequence (e.g., SV40 T antigen).

Histochemical staining using X-gal provided a highly sensitive method for detecting P-galactosidase expression in cells exposed to the modified AcMNPV. When HepG2 cells were exposed to the modified AcMNPV at a moi of 15, about 5–10% of the cells stained with X-gal (FIG. 14A). At a multiplicity of infection (moi) of 125, about 25–50% of the cells were stained (FIG. 14B). No adverse effects of exposure to the virus, such as nuclear swelling, were observed. These data demonstrate that the modified AcMNPV is highly effective at gene transfer into HepG2 cells when a sufficient dose of virus is used. When the Sk-Hep-1 line was exposed to virus at a moi of 15, no stained cells were observed (data not shown). While the majority of Sk-Hep-1 cells that were exposed to virus at a moi of 125, did not stain blue (FIG. 14C), a few cells were found that stained darkly after treatment with this higher doses of virus (FIG. 14D). These data indicate that cells that appear to be refractory to the virus at a relatively low moi can, in fact, be infected, and express the exogenous gene, at a higher moi. Stained cells were not found in mock-infected cultures (data not shown). The frequency of stained cells in the Sk-Hep-1 cell line was estimated to be 2,000–4,000 fold less than in HepG2 cells after exposure to equivalent doses of the modified virus, as determined by cell counting. Thus, the cell type-specificity demonstrated by the modified AcMNPV is relative rather than absolute. These data also indicate that, where a mixture of cells is contacted with the virus (in vitro or in vivo), the dosage of the virus can be adjusted to target the virus to the cells that are infected at a lower moi.

Expression in Primary Cultures of Rat Hepatocytes: This example illustrates that a non-mammalian DNA virus can also be used to express an exogenous gene at high levels in primary cultures of rat hepatocytes. In this experiment, freshly prepared rat hepatocytes were plated onto dishes coated with rat tail collagen as previously described (Rana et al., 1994, Mol. Cell. Biol. 14:5858–5869). After 24 hours, the cells were fed with fresh medium containing RSV-lacZ baculovirus at a multiplicity of infection of approximately 430. After an additional 24 hours, the cells were fixed and stained with X-gal. Over 70% of the cells were stained blue, indicating that they have taken up and expressed the RSV-lacZ cassette (FIG. 15). The frequency of expression obtained in this example is higher than the frequency reported with conventional viral vectors used in gene therapy (e.g., retroviral and Herpes Simplex Virus vectors). Mock-infected cultures did not contain any positively-stained cells (data not shown). Other preferred exogenous genes can be used in lieu of the lacZ gene. In addition, other primary cells can readily be plated and incubated with a non-mammalian cell in lieu of the primary rat hepatocytes.

Expression in Cortex Cultures: The following two examples illustrate that a non-mammalian DNA virus can be used to express an exogenous gene in cultured neuronal and glial cells. For this example, the Z4 virus was prepared from Sf9 cells grown in Hink's TNM-FH media containing 10%-FCS, as described above. The virus was purified by banding on a 20–60% sucrose gradient in phosphate-buffered saline. The titer of the virus employed in the following experiments was $3\times10^8$ pfu/ml (for virus stock #1) or $2\times10^9$ pfu/ml (for virus stock # 2), as measured on Sf9 cells. Each virus stock was sonicated prior to use. For the first example, rat cerebral cortex cultures were prepared from E16 embryonic pups. A 24-well dish was seeded with 300,000 cells/well, and, at 4 days post-plating, the cells were infected by adding varying amounts of virus in serum-containing medium to the wells, as is indicated in Table 4. The virus was allowed to adsorb onto the cells for 24 hours.

TABLE 4

EXPRESSION OF AN EXOGENOUS GENE IN RAT CORTICAL CELLS

| VIRUS | 1 µl | 2 µl | 5 µl | 10 µl | 50 µl | 100 µl |
|---|---|---|---|---|---|---|
| Z4 Stock #1 | moi = 1<br>no blue<br>cells | moi = 2<br>no blue<br>cells | moi = 5<br>~5 blue cells | moi = 10<br>~20 blue cells | moi = 50<br>~500 blue cells | moi = 100<br>~2200 blue cells<br>(~0.75%) |

TABLE 4-continued

EXPRESSION OF AN EXOGENOUS GENE IN RAT CORTICAL CELLS

| VIRUS | 1 µl | 2 µl | 5 µl | 10 µl | 50 µl | 100 µl |
|---|---|---|---|---|---|---|
| Z4 Stock #2 | moi = 6.7 few blue cells | moi = 13.3 ~100 blue cells | moi = 34 ~200 blue cells | moi = 67 ~450 blue cells | moi = 335 ~1000 blue cells | moi = 667 ~1300 blue cells |
| PBS | | | | no blue cells | no blue cells | no blue cells |

Expression of the exogenous β-galactosidase gene was measured by counting the number of blue cells after staining the cells with X-gal. Table 4 provides the number of blue cells observed in five fields of the microscope at 10× magnification; each well contained approximately 65 fields. In some wells, the cells at the periphery of the well were preferentially stained.

These data indicate that the exogenous β-galactosidase gene was expressed from the virus in the cultured neuronal cells. In contrast, no blue cells were detected when the cell cultures were mock-infected with PBS. Thus, this non-mammalian virus can be used to express an exogenous gene in neuronal and glial cells, as determined by the detection of blue cells that were, by cell morphology, identified as neurons and glia according to standard criteria.

In the second example, the Z4 baculovirus was used to express an exogenous gene in cultured cortical cells obtained from rat pups at the E20 and P1 stages. The cells from E20 pups were plated in 24-well dishes at 380,000 cells/well. The cells from P1 pups were plated at 300,000 cells/well. The E20 cultures were treated with araC (to inhibit the growth of glia) at 6 days post-plating, and they were infected at 10 days post-plating. The P1 cultures were treated with araC at 2 days post-plating, and they were infected at 6 days post-plating. Samples of each culture were infected with various dilutions of Z4 virus at titer $2 \times 10^9$ pfu/ml. To measure the strength of the RSV promoter, the cells were also infected, in separate experiments, with Herpes Simplex Virus (HSV) expressing the lacZ gene under two different promoters. In one case, cells were infected with a HSV in which the lacZ gene was placed under the control of an RSV promoter. The titer of this HSV stock was $2 \times 10^7$ IU/ml, as measured on PC12 cells with X-gal histochemistry. For comparison, the cells were infected with a HSV in which the lacZ gene was placed under control of the HSV IE4/5 promoter. The titer of this virus was $2 \times 10^8$ IU/ml, as measured on PC12 cells with X-gal histochemistry. For a negative control, the cells were mock-infected with PBS. Expression of the exogenous lacZ gene was measured by counting the number of blue cells obtained upon staining the cells with X-gal.

The non-mammalian Z4 virus of the invention successfully expressed the exogenous lacZ gene in cultured cortical cells obtained from rat pups at both the E20 and P1 stages of development. With 1–100 µl of the Z4 virus, 4.9–10% of the cortical cells at the E20 stage, and 2.1–5.75% of the cortical cells at the P1 stage, were stained blue with X-gal, indicating expression of the exogenous gene in those cells. Of the cells infected with 0.1–5.0 µl of the HSV RSVlacZ virus, as a positive control, 1.9–3.4% of the E20 cells, and 0.45–4.2% of the P1 cells stained blue with X-gal. When the cells were infected with a 5 µl sample of HSV expressing lacZ from the IE4/5 promoter, nearly 100% of the cells stained blue. When E20 or P1 cortical cells were mock-infected with PBS, as a negative control, no blue cells were detected. These data provide additional evidence that the non-mammalian Z4 baculovirus can be used to express an exogenous gene in cortex cells. These data also indicate that the level of expression obtained with the Z4 virus is comparable to the level of expression obtained with HSV.

Dose-response of Baculovirus-mediated Gene Transfer: The histochemical data presented above indicate that increasing amounts of β-galactosidase are produced after exposure of mammalian cells to increasing amounts of virus. To quantitate the dose-dependence of baculovirus-mediated gene expression, HepG2 cells were exposed to increasing doses of virus and assayed for β-galactosidase enzyme activity. The amount of enzyme produced was linearly related to the inoculum of virus used over a wide range of doses (FIG. 16). This suggests that entry of each virus particle occurs independently of entry of other virus particles. The maximum dose of virus used in this assay was limited by the titer and volume of the viral stock, and no plateau in the amount of expression was observed using higher doses of virus. Accordingly, these data indicate that, in practicing the invention, one can modulate the level expression (i.e., the percent of cells in which the exogenous gene is expressed) by adjusting the dosage of virus used.

Time Course of Baculovirus-mediated Gene Transfer: HepG2 cells were exposed to the RSV-lacZ virus for 1 hour, after which the cells were harvested at various times and quantitatively assayed for β-galactosidase activity. As is shown in FIG. 17, β-galactosidase activity was detected as early as 6 hours after exposure to the virus, and expression peaked 12–24 hours post-infection. As is expected for an episomal DNA molecule, expression from the RSV-lacZ cassette gradually subsided at later time (FIG. 17 and data not shown). LacZ expression remained detectable by X-gal staining at 12 days post-transfection in fewer than 1 in 1,000 cells (data not shown). This expression of LacZ was not the result of viral spread, because culture supernatants taken from HepG2 cells 10 days post-infection had titers of 10 pfu/ml as determined by plaque assay on Sf21 cells. These data suggest that, where the invention is used in the manufacture of proteins that are purified from HepG2 cells, it may be desirable to isolate the protein from the cell at a time not sooner than 6 hours after infection of the cell. Depending on the half-life of the protein, it may be desirable to isolate the protein shortly after the peak in protein expression (i.e., after approximately 22–26 hours (e.g., approximately 24 hours) post-infection for HepG2 cells). The optimal time period for maximizing isolating the manufactured protein can readily be determined for each protein, virus, and cell.

Expression Occurs De Novo in Mammalian Cells: These examples confirm that expression of the exogenous gene occurs de novo in mammalian cells. To demonstrate that the detected reporter gene activity in the mammalian cells was not simply the result of β-galactosidase being physically associated with AcMNPV virions as they enter the mammalian cell, several experiments were performed that demonstrate that the observed expression of the lacZ reporter gene was the result of de novo synthesis of β-galactosidase.

First, the RSV-lacZ virus inoculum was assayed for β-galactosidase activity, and the level of β-galactosidase activity was found to be less than 10% of that expressed after infection of HepG2 cells. Second, HepG2 cells were infected with the RSV-lacZ virus and then cultured in the presence of the protein synthesis inhibitor cycloheximide. Inclusion of cycloheximide after infection inhibited the accumulation of β-galactosidase enzyme activity by more than 90% (Table 5). Third, HepG2 cells were infected at an equivalent moi with BacPAK6 (Clontech), a baculovirus in which the lacZ gene was under control of the viral polyhedrin promoter rather than the RSV promoter (Table 5). The latter virus expresses extremely high levels of β-galactosidase activity in insect cells where the promoter is active (data not shown). In mammalian cells, the viral polyhedrin promoter is inactive, and the virus containing this promoter failed to provide any enzyme activity in mammalian cells (Table 5). In contrast to prior studies of baculovirus interactions with mammalian cells, these data demonstrate that de novo synthesis of lacZ occurs after baculovirus-mediated gene transfer into a mammalian cell.

TABLE 5

BACULOVIRUS-MEDIATED GENE EXPRESSION OCCURS DE NOVO.

| Virus | Drug During Infection | Drug Post Infection | β-galactosidase (% of RSV-lacZ, mean ± SD) |
|---|---|---|---|
| RSV-lacZ | none | none | 100 ± 5.8 |
| none | none | none | 3.2 ± 0.4 |
| RSV-lacZ | none | cycloheximide | 10.3 ± 1.0 |
| BacPAK6 | none | none | 2.8 ± 0.4 |
| RSV-lacZ | chloroquine | chloroquine | 2.9 ± 0.1 |
| RSV-lacZ | none | chloroquine | 25.1 ± 6.2 |

Baculovirus-mediated Gene Transfer is Inhibited by Lysomotropic Agents: To gain insight into the mechanism by which baculoviruses express an exogenous gene in a mammalian cell, the susceptibility of gene expression to a lysomotropic agent was examined. Like other enveloped viruses, the budded form of AcMNPV normally enters cells via endocytosis, followed by low pH-triggered fusion of the viral envelope with the endosomal membrane, thus allowing escape into the cytoplasm (Blissard et al., 1993, J. Virol. 66:6829–6835; Blissard et al., 1990, Ann. Rev. of Entomol. 35:127–155). To determine whether endosome acidification was necessary for baculovirus-mediated gene transfer into mammalian cells, HepG2 cells were infected with RSV-lacZ AcMNPV in the presence of chloroquine, a lysomotropic agent. HepG2 cells were exposed to AcMNPV virus in media containing or lacking inhibitor for 90 minutes, then the virus-containing media were removed and replaced with fresh media containing or lacking inhibitors as listed.

At one day post-infection, the cells were harvested and extracts were assayed for β-galactosidase activity and protein content. Each value in the table represents the average of three independent assays, with the amount of β-galactosidase produced by the RSV-lacZ AcMNPV virus in the absence of inhibitors assigned a value of 100%. β-galactosidase activity was normalized for protein content of each extract. When 25 μM chloroquine was continuously present during and after exposure of HepG2 cells to the virus, de novo expression of β-galactosidase was completely prevented (Table 5). This suggests that baculovirus-mediated gene transfer is dependent upon endosomal acidification. When chloroquine was added to the cells at 90 minutes after exposure to the virus, only partial inhibition of β-galactosidase expression was observed. Apparently, a portion (≈22%) of the viral particles were able to proceed through the endosomal pathway during the 90 minutes of exposure to the virus.

Baculovirus-mediated Gene Transfer is Enhanced by Butyrate: This example illustrates that butyrate enhances the ability of a baculovirus to express an exogenous gene in a mammalian cell. Five transfer plasmids containing different mammalian promoters were created, as diagrammed in FIG. 21. These vectors were constructed using pSV/BV, a modified version of the baculovirus transfer plasmid pBacPAK9 (Clontech), containing an altered polylinker and SV40 splice and polyadenylation signals. pSV/BV was constructed by restriction of pBacPAK9 with NotI, treatment with T4 DNA polymerase to create blunt ends, and self-ligation to remove the NotI site. A new NotI site was then added by ligation of the linker pGCGGCCGC into the SmaI site. Finally, SV40 splice and polyadenylation sequences were added by digestion of a variant of pRSVglobin with BglII-BamHI, and insertion of the 850 bp fragment into the BamHI site of the modified BacPAK9, yielding pSV/BV. The human cytomegalovirus immediate early promoter, 758 bp HindIII-XbaI fragment, was excised from pCMV-EBNA (Invitrogen) at HindIII, BamHI and inserted into the HindIII, BamHI sites of pBluescript (SKII+), yielding plasmid pCMV-SKII+. The promoter was then excised from CMV-SK II+ at the XhoI, BamHI sites and inserted into the XhoI, BglII sites of pSV/BV, yielding plasmid pCMV/BV. The 500 bp mouse phosphoglycerate kinase (PGK) promoter was prepared by cutting pKJ1-neo (Tybulewicz, 1991, Cell 65: 1153–1163) with EcoRI and made blunt with T4 DNA polymerase to remove the EcoRI site. The resulting pKJ1 plasmid lacking the EcoRI site was amplified by pfu polymerase chain reaction using the primers 5'ACCGCGGATCCAATACGACTCACTATAG3' (SEQ ID NO: 5) and

5'CGGAGATCTGGAAGAGGAGAACAGCGCGGCAG3' (SEQ ID NO: 6).

The amplified PGK promoter was then digested with XhoI and BglII and inserted into the same sites of pSV/BV yielding PKJ1/BV. The 345 bp rat β-actin promoter was excised from pINA (6) at BglII, BamHI and inserted into the BglII site of pSV/BV yielding pβ-actin/BV. The 2.3 kb albumin enhancer and 700 bp albumin promoter were excised from pGEMAlbSVPA (Zaret et al., 1988, Proc. Natl. Acad. Sci. 85: 9076–9080) at NaeI, NsiI and inserted into the SmaI, PstI sites of pSV/BV. The RSVlacZ transfer plasmid used (also referred to herein as the Z4 virus) is described above. A 3.0 kb Lac Z cassette was inserted into the NotI site of all of the plasmids constructed (See FIG. 21).

Recombinant viruses were generated by contransfection of the baculovirus transfer vectors with linear BP6 viral DNA (Clontech) into Sf21 cells. The recombinant viruses were purified through three rounds of plaque isolation and amplified on Sf21 cells. The amplified viruses were concentrated by ultracentrifugation as described above and titered by a 96-well method on Sf21 insect cells (O'Reilly et al., 1992, Baculovirus Expression Vectors: A Laboratory Manual, W.H. Freeman, New York, NY).

The human hepatocellular carcinoma cell line HepG2 was infected with each recombinant virus at a multiplicity of infection of 100. Two million cells were infected in a final volume of 1 ml Eagle's Minimum Essential Medium in a 60 mm tissue culture dish. The infection was allowed to proceed for two hours, then 4 ml of complete medium was added to the cells. In a second series of HepG2 infections, the conditions of the first infections were repeated with the exception that after the infection had proceeded for 2 hours 25 µl of sodium butyrate (100 mM) was added to the cells with 1.5 ml complete media. As a control, cells were mock-infected to assess background β-galactosidase enzyme activity. The cell monolayers were collected after 24 hours and prepared for a colorimetric assay (with ONPG) of β-galactosidase enzymatic activity as described above. Hepatocytes were isolated by collagenase perfusion and plated on rat tail collagen as previously described (Boyce et al., 1996, Proc. Natl. Acad. Sci. 93:2348–2352). Assay conditions (time and amount of extract used) were varied to be within the linear range of the assay. The amount of product was determined by spectrophotometry and β-galactosidase enzyme activity was calculated. The Coomassie Plus protein assay (Pierce) was used to determine the protein concentration of the extracts, and results were expressed as units of β-galactosidase normalized to total protein content of the extract. The amount of background activity from the mock-infected cells was subtracted from the total amount of enzyme activity for each of the promoters. Each infection was performed in triplicate, and expressed as the mean average with standard deviation (Table 6).

As shown in Table 6, the incorporation of viral or mammalian cellular promoters into baculoviruses allows for expression of an exogenous gene product in mammalian cells. The CMV promoter led to the highest level of β-galactosidase activity, with the RSV and β-actin promoters producing lower levels of β-galactosidase activity. At the moi of virus employed in this example, the albumin and PGK promoters showed no activity above background levels in extracts of cells that were not treated with butyrate, although positively stained cells were detected by X-gal staining. The addition of sodium butyrate to the cells after infection led to detectable levels of β-galactosidase expression with all of the promoters tested. After treating cells with sodium butyrate, the CMV promoter showed a five-fold increase in expression of the β-galactosidase reporter gene. The RSV LTR, albumin, pGK1, and β-actin promoters all led to increased gene expression after treatment with butyrate. Without being bound to any particular theory, it is postulated that sodium butyrate increases cellular differentiation and histone acetylation, which increases transcription.

TABLE 6

COMPARISON OF VARIOUS PROMOTER STRENGTHS WITH AND WITHOUT SODIUM BUTYRATE

| Promoter | Hep G2 −butyrate | Hep G2 +butyrate | Rat Hepatocytes −butyrate |
|---|---|---|---|
| CMV | 17 ± 1.4[a] | 86 ± 33 | 18 ± 1.2 |
| RSV | 1.0 ± 0.1 | 2.2 ± 0.1 | 0.25 ± 0.11 |
| pGK1 | 0.0 ± 0.0 | 0.02 ± 0.02 | 0.64 ± 0.58 |
| Albumin | 0.0 ± 0.0 | 0.08 ± 0.04 | 0.15 ± 0.08 |
| β-actin | 0.1 ± 0.01 | 0.05 ± 0.02 | 0.25 ± 0.07 |

[a]Promoter strength is expressed in Units/mg of β-galactosidase.

Analysis of RNA Expression From Viral Promoters in HepG2 Cells: One advantage of using a non-mammalian virus to express an exogenous gene in a mammalian cell is that, due to a lack of appropriate host cell factors, the non-mammalian viral promoters may not be active in the mammalian cell. To determine whether AcMNPV viral gene are expressed in HepG2 cells, the viral RNA was analyzed. In these experiments, HepG2 cells were infected with the Z4 virus at a moi of approximately 30. At 18 hours post-infection, the cells were harvested, and total cellular RNA was extracted from the cells. The total cellular RNA was analyzed by Northern blotting for expression of viral genes. The probe included a 1.7 kbp PacI-SalI fragment from pAcUW1 (Pharmingen) which contains the viral late gene, p74, as well as the very late (hyperexpressed) gene, p10. Total cellular RNA from Z4-infected Sf9 insect cells was employed as a positive control. While extremely strong signals were detected for p10 and p74 for the control insect cells, no signal was observed for Z4-infected HepG2 cells or uninfected control cells.

Additional experiments that used reverse transcriptase-PCR (RT-PCR), a highly sensitive method, provided further evidence that the majority of viral genes are not transcribed in the mammalian HepG2 cells. RT-PCR analysis was performed with RNA prepared from Z4-infected HepG2, uninfected HepG2, or infected Sf9 cells at 6 or 24 hours post-infection. HepG2 cells were infected at a moi of 10 or 100. At 6 hours post-infection, no RT-PCR product was observed from the viral p39, ETL, LEF1, IE1, or IE-N genes at either dose of virus in Z4-infected HepG2 cells. In contrast, RT-PCR products were readily detected in Z4-infected Sf9 cells. At 24 hours post-infection, no expression of these gene was detected in HepG2 cells infected at a moi of 10. At 24 hours post-infection, no expression of the viral p39, ETL, or LEFI genes was observed in HepG2 cells infected at an moi of 100. However, at this high does of virus, low levels of expression from the viral IE1 and E-N genes was observed. The low level of expression detected at an moi of 100 was nonetheless significantly lower than the level of expression in insect cells.

Expression of these genes may result from recognition of the viral TATA box by mammalian transcription factors (i.e., transcription of the immediate early genes by RNA polymerase II (see, e.g., Hoopes and Rorhman, 1991, Proc. Natl. Acad. Sci. 88:4513–4517). In contrast to the immediate early genes, the late or very late viral genes are transcribed by a virally-encoded RNA polymerase that, instead of requiring a TATA box, initiates transcription at a TAAG motif (O'Reilly et al., supra). Accordingly, expression of the viral late or very late genes is naturally blocked in mammalian cells. If desired, expression of the immediate early genes can be blocked by deleting those genes, using conventional methods.

While certain viruses have an intrinsic ability to infect liver cells, infection of liver cells by other viruses may be facilitated by a cellular receptor, such as a cell-surface asialoglycoprotein receptor (ASGP-R). HepG2 cells differ from Sk-Hep-1 human hepatocytes and NIH3T3 mouse fibroblast cells by the presence of ASGP-R on the cell surface. In certain of the above experiments, β-galactosidase was expressed in fewer Sk-Hep-1 cells (FIG. 14B) or NIH3T3 cells than HepG2 cells. The lacZ gene was expressed in HepG2 cells at a frequency estimated as greater than 1,000 fold more than that in Sk-Hep-1 cells, based on quantitative counts of X-gal stained cells. Normal hepatocytes have 100,000 to 500,000 ASGP-R, with each receptor internalizing up to 200 ligands per day. The ASGP-R may facilitate entry of the virus into the cell by providing a cell-surface receptor for glycoproteins on the virion. The glycosylation patterns of insect and mammalian cells differ, with the carbohydrate moieties on the surface of the virion produced in insect cells lacking terminal sialic acid. Those carbohydrate moieties may mediate internalization and trafficking of the virion. In addition to the ASGP-R, other galactose-binding lectins that exist in mammals (see, e.g., Jung et al., 1994, J. Biochem. (Tokyo) 116:547–553) may mediate uptake of the virus.

If desired, the cell to be infected can be modified to facilitate entry of the baculovirus into the cell. For example, ASGP-R can be expressed on the surface of a cell to be infected by the virus (e.g., baculovirus). The genes encoding the ASGP-R have been cloned (Spiess et al., 1985, J. Biol. Chem. 260:1979 and Spiess et al., 1985, Proc. Natl. Acad. Sci. 82:6465), and standard methods (e.g., retroviral, adeno-associated virus, or adenoviral vectors or chemical methods) can be used for expression of the ASGP-R in the cell to be infected by a virus. Other suitable mammalian lectins can be substituted for the ASGP-R in such methods (see, e.g., Ashwell et al., 1982, Ann. Rev. Biochem. 51:531–534). Other receptors for ligands on the virion, such as receptors for insect carbohydrates or the CD4 receptor for HIV, can also be expressed on the surface of the mammalian cell to be infected to facilitate infection (see, e.g., Monsigny et al., 1979, Biol. Cellulaire 33:289–300).

Entry into the cell also can be facilitated by modifying the virion, e.g., through chemical means, to enable the virion to bind to other receptors on the mammalian cell (see, e.g., Neda, et al., 1991, J. Biol. Chem. 266:14143–14146 and Burns et al., 1993, Proc. Natl. Acad. Sci. 90:8033–8037). Alternatively, the glycosylation patterns and levels of baculovirus can be modified by growing the virus on Ea4 cells, which are derived from *Estigmena acrea* (e.g., as described by Rooney et al. in Nature Biotech). In addition, one can modify the virus such that it expresses mammalian glycosylation enzymes (Jarvis et al., 1996, Nature Biotech. 14:1288–1292).

II. Therapeutic Use of a Non-mammalian DNA Virus Expressing an Exogenous Gene

The discovery that a non-mammalian DNA virus efficiently expressed a lacz reporter gene in several mammalian cells indicates that a non-mammalian DNA virus can be used therapeutically to express an exogenous gene in a cell of a mammal. For example, the method of the invention can facilitate expression of an exogenous gene in a cell of a patient for treatment of a disorder that is caused by a deficiency in gene expression. Numerous disorders are known to be caused by single gene defects (see Table 7), and many of the genes involved in gene deficiency disorders have been identified and cloned. Using standard cloning techniques (see, e.g., Ausubel et al., Current Protocols in Molecular Biology, John Wiley & Sons, (1989)), a non-mammalian virus can be engineered to express a desired exogenous gene in a mammalian cell (e.g., a human cell).

TABLE 7

EXAMPLES OF DISORDERS THAT CAN BE TREATED WITH THE INVENTION AND GENE PRODUCTS THAT CAN BE MANUFACTURED WITH THE INVENTION

| Gene Product | Disorder |
| --- | --- |
| fumarylacetoacetate hydrolase | hereditary tyrosinemia |
| phenylalanine hydroxylase | phenylketonuria |
| LDL receptor | familial hypercholesterolemia |
| alpha-1 antitrypsin | alpha-1 antitrypsin deficiency |
| glucose-6-phosphatase | glycogen storage diseases |
| porphobilinogen deaminase | diseases caused by errors in porphyrin metabolism, e.g., acute intermittent porphyria |
| CPS-1, OTC, AS, ASL, or arginase | disorders of the urea cycle |
| factors VIII & IX | hemophilia |
| cystathione β-synthase | homocystinuria |
| branched chain ketoacid decarboxylase | maple syrup urine disease |
| albumin | hypoalbuminemia |

TABLE 7-continued

EXAMPLES OF DISORDERS THAT CAN BE TREATED WITH THE INVENTION AND GENE PRODUCTS THAT CAN BE MANUFACTURED WITH THE INVENTION

| Gene Product | Disorder |
| --- | --- |
| isovaleryl-CoA dehydrogenase | isovaleric acidemia |
| propionyl CoA carboxylase | propionic acidemia |
| methyl malonyl CoA mutase | methylmalonyl acidemia |
| glutaryl CoA dehydrogenase | glutaric aciderma |
| insulin | insulin dependent diabetes |
| β-glucosidase | Gaucher's disease |
| pyruvate carboxylase | pyruvate catboxylase deficiency |
| hepatic phosphorylase or phosphorylase kinase | glycogen storage diseases |
| glycine decarboxylase, H-protein, or T-protein | non-ketotic hyperglycinemias |
| Wilson's disease copper-transporting ATPase | Wilson's disease |
| Menkes disease copper-transporting ATPase | Menkes disease |
| cystic fibrosis transmembrane conductance regulator | cystic fibrosis |

The invention can also be used to facilitate the expression of a desired gene in a cell having no obvious deficiency. For example, the invention can be used to express insulin in a hepatocyte of a patient in order to supply the patient with insulin in the body. Other examples of proteins that can be expressed in a mammalian cell (e.g., a liver cell) for delivery into the system circulation of the mammal include hormones, growth factors, and interferons. The invention can also be used to express a regulatory gene or a gene encoding a transcription factor (e.g., a VP16-tet repressor gene fusion) in a cell to control the expression of another gene (e.g., genes that are operably-linked to a tet operator sequence; see, e.g., Gossen et al., 1992, Proc. Natl. Acad. Sci. 89:5547–5551). In addition, the invention can be used in a method of treating cancer by expressing in a cell a cancer therapeutic gene, such as a gene encoding a tumor suppressor (e.g., p53), tumor necrosis factor, thymidine kinase, diphtheria toxin chimera, or cytosine deaminases (see, e.g., Vile and Russell, 1994, Gene Therapy 1:88–98).

Other useful gene products include RNA molecules for use in RNA decoy, antisense, or ribozyme-based methods of inhibiting gene expression (see, e.g., Yu et al., 1994, Gene Therapy 1:13–26). If desired, the invention can be used to express a gene, such as cytosine deaminase, whose product will alter the activity of a drug or prodrug, such as 5-fluorocytosine, in a cell (see, e.g., Harris et al., 1994, Gene Therapy 1: 170–175). Methods such as the use of ribozymes, antisense RNAs, transdominant repressors, polymerase mutants, or core or surface antigen mutants can be used to suppress hepatitis viruses (e.g., hepatitis virus A, B, C, or D) in a cell. Other disorders such as familial hemachromatosis can also be treated with the invention by treatment with the normal version of the affected gene.

Preferred genes for expression include those genes that encode proteins that are expressed in normal mammalian cells (e.g., hepatocytes or lung cells). For example, genes encoding enzymes involved in the urea cycle, such as the genes encoding carbamoyl phosphate synthetase (CPS-I), ornithine transcarbamylase (OTC), arginosuccinate synthetase (AS), arginosuccinate lyase (ASL), and arginase are useful in this method. All of these genes have been cloned (for OTC, see Horwich et al., 1984, Science 224:1068–1074 and Hata et al., 1988, J. Biochem (Tokyo) 103:302–308; for AS, see Bock et al., 1983, Nucl. Acids Res. 11:6505; Surh et al., 1988, Nucl. Acids Res. 16:9252; and Dennis et al., 1989, Proc. Natl. Acad. Sci. 86:7947; for ASL, see O'Brien et al., 1986, Proc. Natl. Acad. Sci. 83:7211; for CPS-I, see Adcock et al., 1984, (Abstract) Fed. Proc. 43:1726; for arginase, see Haraguchi et al., Proc. Natl. Acad. Sci. 84:412). Subcloning these genes into a baculovirus can be readily accomplished with common techniques.

The therapeutic effectiveness of expressing an exogenous gene in a cell can be assessed by monitoring the patient for known signs or symptoms of a disorder. For example, amelioration of OTC deficiency and CPS deficiency can be detected by monitoring plasma levels of ammonium or orotic acid. Similarly, plasma citrulline levels provide an indication of AS deficiency, and ASL deficiency can be followed by monitoring plasma levels of arginosuccinate. Parameters for assessing treatment methods are known to those skilled in the art of medicine (see, e.g., Maestri et al., 1991, J. Pediatrics, 119:923–928).

The non-mammalian DNA virus (e.g., baculovirus) can be formulated into a pharmaceutical composition by admixture with a pharmaceutically acceptable non-toxic excipient or carrier (e.g., saline) for administration to a mammal. In practicing the invention, the virus can be prepared for use in parenteral administration (e.g., for intravenous injection (e.g., into the portal vein)), intra-arterial injection (e.g., into the femoral artery or hepatic artery), intraperitoneal injection, intrathecal injection, or direct injection into a tissue or organ (e.g., intramuscular injection). In particular, the non-mammalian virus can be prepared in the form of liquid solutions or suspensions in conventional excipients. The virus can also be prepared for intranasal or intrabronchial administration, particularly in the form of nasal drops or aerosols in conventional excipients. If desired, the virus can be sonicated in order to minimize clumping of the virus in preparing the virus.

In practicing the invention, the virus can be used to infect a cell outside of the mammal to be treated (e.g., a cell in a donor mammal or a cell in vitro), and the infected cell then is administered to the mammal to be treated. In this method, the cell can be autologous or heterologous to the mammal to be treated. For example, an autologous hepatocyte obtained in a liver biopsy can be used (see, e.g., Grossman et al., 1994, Nature Genetics 6:335). The cell can then be administered to the patient by injection (e.g., into the portal vein). In such a method, a volume of hepatocytes totaling about 1%–10% of the volume of the entire liver is preferred. Where the invention is used to express an exogenous gene in a liver cell, the liver cell can be delivered to the spleen, and the cell can subsequently migrate to the liver in vivo (see, e.g., Lu et al., 1995, Hepatology 21:7752–759). If desired, the virus may be delivered to a cell by employing conventional techniques for perfusing fluids into organs, cells, or tissues (including the use of infusion pumps and syringes). For perfusion, the virus is generally administered at a titer of $1\times10^6$ to $1\times10^{10}$ pfu/ml (preferably $1\times10^9$ to $1\times10^{10}$ pfu/ml) in a volume of 1 to 500 ml, over a time period of 1 minute to 6 hours. If desired, multiple doses of the virus can be administered to a patient intravenously for several days in order to increase the level of expression as desired.

The optimal amount of virus or number of infected cells to be administered to a mammal and the frequency of administration are dependent upon factors such as the sensitivity of methods for detecting expression of the exogenous gene, the strength of the promoter used, the severity of the disorder to be treated, and the target cell(s) of the virus. Generally, the virus is administered at a multiplicity of infection of about 0.1 to 1,000; preferably, the multiplicity of infection is about 5 to 100; more preferably, the multiplicity of infection is about 10 to 50.

III. Examples of Use of a Non-mammalian Virus to Express an Exogenous Gene In Vivo The following examples demonstrate that a non-mammalian DNA virus can be used to express an exogenous gene in a cell in vivo. These examples also demonstrate that in vivo gene expression can be achieved by administering the virus by intravenous injection, intranasal administration, or direct injection of the virus into the targeted tissue. The first example demonstrates expression of an exogenous gene in brain cells in vivo. The second example provides evidence of expression of an exogenous gene in liver, following intravenous injection of the virus. In the third example, expression of the exogenous gene is detected in skin after topical application of the Z4 virus to injured skin. In the remaining examples, a virus carrying an exogenous gene was injected directly into an organ. These examples demonstrate in vivo expression of an exogenous gene in skin, liver, spleen, kidney, stomach, skeletal muscle, uterus, and pancreas.

Injection Into Portal Vein: For the first example, 0.5 ml of Z4 virus ($\approx 1.4\times10^9$ pfu/ml) was injected (at a rate of 1 ml/min) into the portal vein of a single rat. At approximately 72 hours after infection, lacZ expression was detectable in at least one liver cell of the cryosections that were examined by conventional histochemical methods. The efficiency of expression may be increased by any one, or a combination of, the following procedures: (1) pre-treating the animal with growth factors; (2) partial hepatectomy, (3) administration of immunosuppressants to suppress any immune response to the virus; (4) use of a higher titer or dose of the virus; (5) infusion of the virus by surgical perfusion to the liver (e.g., in order to limit possible non-specific binding of the virus to red blood cells); and/or (6) sonication of the virus to minimize clumping of the virus.

Expression in Brain: For the second example, a 2 $\mu$l sample of Z4 virus (at a titer of $4.8\times10^{10}$ pfu/ml) was injected, using stereotactic procedure, into the olfactory bulb in the brain of an anesthetized adult rat. The virus was injected slowly (over a 30 minute time period) to avoid compressing the brain tissue. At 1 day post-injection, the rat was euthanized, and the brain tissue was processed for detection of expression of the exogenous lacZ gene by X-gal histochemistry. Injection of the Z4 virus into the brain resulted in in vivo expression of lacZ, as was evidenced by patches of cells that were strongly stained blue. More than 104 cells were stained blue upon injection of approximately $10^7$ pfu. These data thus indicate that an exogenous gene can be expressed in the brain of a mammal by injecting into the brain a non-mammalian DNA virus whose genome includes the exogenous gene.

Topical Application and Expression in Skin: This example demonstrates that topical application of the Z4 virus to abraded skin of a mouse can result in expression of a heterologous gene in the skin. These experiments involved four differently-treated areas on the skin of a mouse. Two of the areas (an abraded and a non-abraded area) were treated with phosphate-buffered saline. The other two areas (an abraded and a non-abraded area) were treated with the Z4 virus (50 $\mu$l at $4.8\times10^{10}$ pfu/ml). After treatment, each area of the skin was cut into sections using a cryostat.

Topical application of the Z4 virus (50 $\mu$l at $4.8\times10^{10}$ pfu/ml) to injured skin of a mouse resulted in expression of the exogenous gene in nearly 100% of the cells of the basal layer of the epidermis. Staining of deeper structures was not detected. In one cryostat section, various areas of the epidermis were stained in multiple sections. In a second cryostat section, occasional blue cells were present. In a third cryostat section, patches of staining were detected, and in a fourth cryostat section, the staining was nearly continuous and very dark. Although the pattern of gene expression varied slightly between the four cryostat sections obtained from this area of skin, the example demonstrates that topical application of the Z4 virus to abraded skin consistently resulted in expression of the heterologous gene in skin.

Injection Into a Tissue or Organ: In the following examples, expression of an exogenous gene was detected in vivo after a non-mammalian DNA virus carrying the gene was injected directly into four distinct organs. For these examples, the Z4 virus was prepared from 1 L of Z4-infected (moi of 0.5) Sf9 cells grown in spinner culture in serum-free medium. The cells and debris were removed by centrifuging the cell culture at 2000 rpm for 10 minutes. The virus was pelleted by centrifugation through a sucrose cushion in an SW28 rotor at 24,000 rpm for 75 minutes. For preparation of this virus stock, 33 ml of cleared virus was layered over a 3 ml sucrose cushion (27% sucrose (w/v) in 10 mM Tris-HCl (pH 7.5), 1 mM EDTA (TE)). The virus was resuspended by overnight incubation at 4° C. in 0.3 ml TE per tube. The virus was purified by banding in a 20–60% sucrose (w/v in TE) gradient in SW41 tubes that were centrifuged at 38,000 rpm for 75 minutes. The virus bands were collected with a syringe and pelleted in SW50.1 rotor centrifuged at 30,000 rpm for 60 minutes. The virus pellet was resuspended in a total of 0.7 ml PBS by overnight incubation at 4° C. The titer of the concentrated Z4 stock, as determined in a conventional plaque assay, was $4.8 \times 10^{10}$ pfu/ml.

To assay for gene expression in vivo, the Z4 virus was administered Balb/c female mice by direct injection of a 50 μl aliquot of the concentrated virus ($2.4 \times 10^9$ pfu total) into either the liver, spleen, kidney, muscle, uterus, pancreas, or skin of a mouse. Surgery was required for administration to liver, spleen and kidney. To spread the virus throughout an organ, the 50 μl virus sample was injected into two or three sites in an organ. A 50 μl sample of PBS was used as a negative control. For assaying gene expression in the liver, only one lobe of the liver was injected, and a separate mouse received the PBS injection as a negative control. For assaying gene expression in the spleen, an uninjected mouse served as a negative control. For assaying gene expression in kidney, muscle, and skin, contralateral controls were performed (the Z4 virus was injected into the right side of the organ, and PBS was injected into the left of the organ). For assaying expression in muscle, the virus was injected into the tibealis anterior hind leg muscle after shaving the mouse. For assaying expression in skin, the abdomen of the mouse was shaved, and 50 μl of Z4 virus were injected into a marked section of the abdomen. At 24 hours post-injection, the mice were sacrificed and dissected. The Z4- and PBS-injected organs were frozen in liquid nitrogen, and 7 μm thin sections were prepared using a cryostat (Reichert-Jung Cryocut 1800). β-galactosidase activity was measured by fixing the thin sections and staining with X-gal, as described above. Each of the organs that received the Z4 virus expressed the exogenous lacZ gene in vivo. In each case, the PBS negative control did not promote expression of the exogenous gene.

Injection and Expression in Skin: In this example, in vivo expression of the exogenous lacZ gene of Z4 was observed in mouse skin after injection of $2.4 \times 10^9$ pfu into the skin. A high level of expression (over 25% of cells within the area of injection) was achieved in the dermis after subcutaneous injection of the virus. Although the muscle layer was predominantly unstained, positive staining of some skeletal muscle fibers was observed. As a negative control, PBS was injected into the skin. Although some staining was observed in the sebaceous glands, it is most probably due to the presence of bacteria A low level of staining was also detected in the dermis. Similar results were obtained when the Z4 virus was applied topically to uninjured (non-abraded) skin, although no clear epidermal staining was detected. Nonetheless, these data indicate that the Z4 virus can be used to express a heterologous gene in the skin of a mammal when the virus is injected subcutaneously into the mammal.

Expression in Liver: In this example, expression of the exogenous gene was detected in liver. Blue coloration, indicative of β-galactosidase expression, was detected in multiple areas of the injected lobe. Although the most intense coloration was at the point of injection, the internal areas of the liver sections exhibited the blue coloration that is indicative of gene expression. Expression of the exogenous gene appeared to be detected both in hepatocytes and Kupffer cells of the lobes that received the Z4 virus. In contrast, uninjected lobes from the same liver were negative. These results thus indicate that an exogenous gene can be expressed in a liver cell by injecting into the liver a non-mammalian DNA virus encoding the gene.

Expression in Spleen: In this example, thin sections of the spleen were assayed for gene expression following injection of the virus carrying the exogenous gene into the spleen. Spleen cells that had received the Z4 virus in vivo expressed the lacZ gene. The blue coloration was detected in cells located throughout the entire spleen. The intensity of blue coloration obtained with spleen cells was less than the intensity obtained with liver cells. Nonetheless, the blue coloration was indicative of significant expression of the exogenous gene. No blue coloration was detected in a spleen that did not receive the virus. These data thus indicate that an exogenous gene can be expressed in a spleen cell in vivo upon injection of a non-mammalian DNA virus whose genome carries the gene.

Expression in Kidney: In this example, in vivo expression of an exogenous gene was detected in a kidney that was injected with Z4 as described above. The Z4-injected kidney displayed clear blue coloring that is indicative of lacZ expression; in contrast, a PBS-injected control kidney displayed no blue coloration. The blue coloration was primarily around the edges of the sections of the kidney. Indirect immunofluorescence also indicated that the viral particles were concentrated in the edges of the sections, providing a correlation between gene expression and localization of the virus. These data thus indicate that a non-mammalian DNA virus can be used to express an exogenous gene in a kidney cell in vivo.

Expression in Stomach: In this example, the Z4 virus (50 μl) was injected into the center of the stomach of Balb/C mice. The animals were sacrificed on the day following injection, and the stomachs were frozen in liquid nitrogen, and cryostat sectioned and stated as previously described. Cell transfection was observed in gastric mucosal and muscle cells. Positive staining was detected in glands, with most staining occurring at the bases of the glands. These observations indicate that a non-mammalian DNA virus can be used to express a heterologous gene in the stomach of mice. In these experiments, blue staining was also detected in the lumen. The blue coloration in that particular region may result from bacteria in the gut, rather than expression from the virus.

Expression in Skeletal Muscle: In this example, in vivo expression of the exogenous lacZ gene of Z4 was detected in muscle after direct injection of virus into the tibialis anterior. Blue coloration was found only in discrete loci in the muscle, and the coloration was not as intense or widespread as the coloration observed in liver, spleen, or skin. Nonetheless, the blue coloration was significant, indicating that a non-mammalian DNA virus can be used to express an exogenous gene in muscle in vivo.

Expression in Uterus: In this example, expression of the lacZ reporter gene was detected in the uterus. A 50 $\mu$l aliquot of the Z4 virus ($2.4 \times 10^9$ pfu) was injected directly into the uterus of a mouse. The animal was sacrificed on the day following injection, and cryostat sections were prepared as previously described. Staining of the sections with X-gal produced blue coloration in an area of the uterus with little tissue disruption. The positive cells were mostly endometrial stromal cells, rather than gland elements. These data indicate that a non-mammalian DNA virus can be used to express a heterologous gene in the uterus of a mammal.

Expression in Pancreas: This example demonstrates that a non-mammalian DNA virus can be used to express a heterologous gene in the pancreas of a mammal. A 50 $\mu$l aliquot of the Z4 virus ($2.4 \times 10^9$ pfu) was injected directly into the pancreas of a mouse. On the day following injection, the mouse was sacrificed, and the pancreas was stained with X-gal according to conventional methods. Large areas of positive cells were detected, indicating that the Z4 virus successfully expressed the lacZ gene in the pancreas.

Summary: In sum, these examples demonstrate that a non-mammalian DNA virus (e.g., a baculovirus) can be used to express an exogenous gene in a mammalian cell in vivo. These examples employed several distinct animal model systems and methods of administering the virus. In each and every case, the non-mammalian DNA virus successfully expressed the exogenous gene in vivo. These data thus provide support for the assertion that a non-mammalian DNA virus can be used to express an exogenous gene in other, non-exemplified cells in vivo. In addition, in at least some tissues, the level of expression in vivo was, surprisingly, higher than the level that would have been predicted from the corresponding in vitro experiments (e.g., the brain versus cultured neurons). All of these examples provide evidence of the in vivo utility of the invention.

PART B: AN ALTERED COAT PROTEIN ENHANCES THE ABILITY OF A NON-MAMMALIAN DNA VIRUS TO EXPRESS AN EXOGENOUS GENE IN A MAMMALIAN CELL

Now that it has been demonstrated that a non-mammalian DNA virus can be used to express an exogenous gene in a mammalian cell, the following examples are provided to demonstrate that an altered coat protein enhances the ability of the non-mammalian DNA virus to express the exogenous gene in a mammalian cell.

Construction of Baculovirus Transfer Plasmid pVGZ3

These examples employ a baculovirus that has been engineered to express a vesicular stomatitis virus glycoprotein G (VSV-G) as an altered coat protein. The baculovirus transfer plasmid pVGZ3 is a derivative of the baculovirus transfer plasmid Z4, which was used in many of the examples summarized above.

The baculovirus transfer plasmid pVGZ3 was constructed by inserting expression cassettes encoding VSV-G and the reporter gene lacZ into the baculovirus transfer vector BacPAK9 (Clontech; Palo Alto, Calif.). To produce this transfer plasmid, cDNA encoding VSV-G was excised as a 1,665 bp BamHI fragment from pLGRNL (Bums, 1993, Proc. Natl. Acad. Sci. 90:8033–8037). The resulting plasmid was termed VSVG/BP9 (FIG. 18). The RSV LTR, lacZ gene, and SV40 polyadenylation signal were excised from the Z4 transfer plasmid using BglII and BamHI to produce a 4,672 bp fragment. This fragment was inserted into the BglII site of VSVG/BP9 such that the lacZ gene was positioned downstream from the VSV-G gene to produce the VGZ3 transfer plasmid (FIG. 19). In VGZ3, the directions of transcription of the VSV-G and lacZ genes are convergent. In other words, the promoters lie at opposite ends of the inserted sequences, with the lacZ and VSV-G genes being transcribed towards each other. The SV40 polyA site is bidirectional and used by both the VSV-G and lacZ genes.

Because the VSV-G gene in this transfer plasmid is operably linked to a baculovirus polyhedrin promoter, the plasmid offers the advantage of high levels of expression of the VSV-G gene in insect cells and relatively low levels of expression in mammalian cells. This pattern of expression of the altered coat protein is desirable because the altered coat protein is produced efficiently in insect cells, where the non-mammalian DNA virus having an protein is manufactured before the virus is delivered to a mammalian cell. Producing the virus in insect cells before using the virus to infect mammalian cells obviates concerns about expressing a viral coat protein (e.g., VSV-G) in mammalian cells.

A schematic representation of a budding virus having an altered coat protein is provided in FIG. 20. Once the virus infects a mammalian cell, expression of the altered coat protein is not desirable. Therefore, the use of an non-mammalian (e.g., insect) virus promoter, which is not active in mammalian cells, is preferable for driving expression of the altered coat protein. By contrast, the exogenous gene of interest (here, the lacZ reporter gene) is operably linked to an RSV LTR. As is desired, expression of a gene driven by the RSV LTR is obtained both in insect cells and in mammalian cells.

Standard procedures were used to produce the recombinant baculovirus VGZ3 from the pVGZ3 transfer plasmid, described above. Briefly, Sf9 cells were co-transfected, according to the manufacturer's instructions, by lipofection with pVGZ3 and the baculovirus genomic DNA BacPAK6 (Clontech; Palo Alto, Calif.) that had been digested with Bsu36I. The virus was plaque purified and amplified according to standard techniques. Using a conventional plaque assay on Sf9 cells, the viral titer was determined to be $3.1\times10^7$ pfu/ml.

Enhanced Expression in HepG2, Vero, and HeLa Cells: This example demonstrates that VGZ3, the baculovirus having an altered coat protein, has an enhanced ability, relative to the Z4 virus described above, to express an exogenous gene in a mammalian cell. To provide sensitivity in the assays; these experiments were performed under conditions in which the Z4 virus expresses an exogenous gene at relatively low levels. Three different cell types were used, including HepG2 cells, Vero cells (a kidney cell line), and HeLa cells (a cervical carcinoma cell line). In these experiments, $1\times10^5$ cells of each cell type were, independently, seeded into multiple wells of 12-well culture plates. On the following day, the tissue culture medium was replaced with fresh medium, and the Z4 and VGZ3 viruses were added, separately, to the cells. The viruses were used at multiplicities of infection of 0, 1.25, 10, and 80 (assuming that the cell number had doubled overnight), and each experiment was performed in duplicate. On the day following the addition of virus, the cells were harvested, and expression of the exogenous lacZ gene was detected by X-gal staining or by using a quantitative chemiluminescent β-galactosidase assay (Clontech; Palo Alto, Calif.). The results of these assays are presented in Table 8.

TABLE 8

USE OF A NON-MAMMALIAN DNA VIRUS HAVING AN ALTERED COAT PROTEIN TO ACHIEVE ENHANCED EXPRESSION OF AN EXOGENOUS GENE IN HEPG2 AND HELA CELLS

| Cell Line | Virus | moi | Chemiluminescence Units | VGZ3 Superiority[a] |
|---|---|---|---|---|
| HepG2 | Z4 | 80 | 16.4 | |
| HepG2 | VGZ3 | 80 | 180.2 | 11.0-fold |
| HeLa | Z4 | 80 | 0.02[b] | |
| HeLa | VGZ3 | 80 | 1.75 | >87.5-fold |
| HeLa | VGZ3 | 1.25 | 0.07 | >224-fold |

[a]Superiority was calculated as VGZ3 transduction units ÷ Z4 transduction units for each cell type.
[b]0.02 was the background level in the chemiluminescent assay.
[c]The difference in moi (1.25 for VGZ3 and 80 for Z4) was accounted for in determining the VGZ3 superiority.

This example demonstrates that a baculovirus that is engineered to express a VSV glycoprotein G has an enhanced ability, relative to a baculovirus that lacks the altered coat protein, to express an exogenous gene in a mammalian cell. In this example, expression of the exogenous lacZ gene was detected in 100% of the HepG2 cells that were contacted with VGZ3 at an moi of 80. In contrast, under these conditions, expression of the exogenous gene was detected in only 15% of the cells that were contacted with the Z4 virus (a virus that does not have an altered coat protein). Accordingly, these data show that altering a coat protein enhances the ability of a virus to express an exogenous gene in a mammalian cell.

Enhanced expression of the exogenous gene was also achieved with Vero cells: over 50% of the VGZ3-treated cells turned blue, whereas only 5–10% of the Z4-treated cells turned blue upon staining with X-gal. Further evidence that the altered coat protein enhances the ability of a virus to express and exogenous gene in a mammalian cell comes from a relatively sensitive assay employing HeLa cells. Under the conditions employed in this example, the Z4 virus does not efficiently express an exogenous gene in HeLa cells. No blue cells were detected at an moi of 80, indicating that the frequency of gene expression was less than $1\times10^{5}$. By contrast, approximately 3% of the HeLa cells treated with the VGZ3 virus were blue, indicating that the efficiency of gene expression was $3\times10^{-2}$, which is 12,000-fold better than the efficiency obtained with Z4. With the VGZ3 virus, blue HeLa cells were also detected at the low moi of 1.25, whereas no blue cells were detected at the moi with the Z4 virus.

In sum, these data indicate that an altered coat protein on a non-mammalian DNA virus can enhance the ability of that virus to infect and express a gene in a mammalian cell. In addition, employment of an altered coat protein allows the virus to infect a cell at a lower moi. Thus certain cells that appear to be refractive to the virus at a given moi (e.g., HeLa cells) can be infected with a virus having an altered coat protein, thereby expanding the apparent host range of the virus. A virus having an altered coat protein thus offers the advantage of permitting expression of an exogenous gene at a low moi, relative to the moi needed with a virus that lacks an altered coat protein.

As was described above for the Z4 virus, exogenous gene expression in cells treated with the VGZ3 virus results from de novo gene expression within the mammalian cell. Both cycloheximide, which inhibits protein synthesis, and chloroquine, which inhibits endosome acidification, separately inhibited β-galactosidase expression in VGZ3-treated mammalian cells (data not shown). Thus, β-galactosidase detected in the mammalian cells in these experiments can be attributed to de novo protein synthesis within the mammalian cell.

Enhanced Expression in PC12 Cells: In this example, the VGZ3 virus is shown to increase the level of exogenous gene expression in rat cortical neuronal cells, relative to the level obtained with the Z4 virus. Using conventional methods, PC12 cells were plated at 10,000 cells/well in a 24-well dish. On day 1, the cell culture medium (DMEM containing 5% FBS and 10% horse serum) was replaced with fresh cell culture medium that also contained 50 ng/ml of nerve growth factor (NGF). Fresh NGF-containing-medium was again added at days 3 and 5. On day 6, the cells were infected with various dilutions of Z4 virus and VGZ3 virus, as shown in Table 9. At day 7, the cells were fixed and stained for -galactosidase by immunocytochemistry using an anti-p-galactosidase antibody (available from 5'→3' Inc.). Under these conditions, fewer than 1% of the PC12 cells infected with $2\times10^{8}$ pfu of Z4 expressed the exogenous gene, and approximately 17.5% of the cells infected with $1\times10^{7}$ pfu of VGZ3 expressed the exogenous gene. Accordingly, these data provide additional evidence that a virus having an altered coat protein has a superior ability to express an exogenous gene in a mammalian cell.

Enhanced Expression in Primary Rat Cortical Cells

This example demonstrates that a virus having an altered coat protein provides enhanced expression of an exogenous gene in a primary cultures of rat cortical cells, as compared with a virus lacking the altered coat protein. For this example, cultures of rat cortical cells were prepared and infected as described above under "Expression in Cortex Cultures." The Z4 and VGZ3 viruses were used at the moi shown in Table 9 (note: the moi of Z4 was approximately 10-fold higher than the moi of VGZ3). When the number of blue cells obtained is compared with the moi of Z4 or VGZ3 used, it becomes apparent that the VGZ3 virus is more efficient at expressing the exogenous gene in the mammalian cells than is the Z4 virus. In addition, this example demonstrates that a non-mammalian DNA virus having an altered coat protein can direct exogenous gene expression in primary rat neurons (in addition to the cell line PC12, as shown above).

TABLE 9

USE OF A NON-MAMMALIAN DNA VIRUS HAVING AN ALTERED COAT PROTEIN TO ACHIEVE ENHANCED EXPRESSION OF AN EXOGENOUS GENE IN PRIMARY CULTURES OF RAT CORTICAL CELLS

| VIRUS | 1 μl | 2 μl | 5 μl | 10 μl | 50 μl | 100 μl |
|---|---|---|---|---|---|---|
| Z4 | moi = 1[a] no blue cells | moi = 2 no blue cells | moi = 5 ≈5 blue cells | moi = 10 ≈20 blue cells | moi = 50 ≈500 blue cells | moi = 100 ≈2200 blue cells ≈0.75% |

TABLE 9-continued USE OF A NON-MAMMALIAN DNA VIRUS HAVING AN ALTERED COAT PROTEIN TO ACHIEVE ENHANCED EXPRESSION OF AN EXOGENOUS GENE IN PRIMARY CULTURES OF RAT CORTICAL CELLS

| VIRUS | 1 µl | 2 µl | 5 µl | 10 µl | 50 µl | 100 µl |
|---|---|---|---|---|---|---|
| VGZ3 | moi = 0.1 no blue cells | moi = 0.2 no blue cells | moi = 0.5 no blue cells | moi = 1 ≈10 blue cells | moi = 5 ≈200 blue cells | moi = 10 ≈60 blue cells[b] |
| PBS | | | | no blue cells | no blue cells | no blue cells |

[a]The moi's were estimated based on the number of cells plated the day before infection.
[b]Because of cell death occurring in this well, fewer stained cells were detected. Nonetheless, the percentage of blue cells was high.

Enhanced Expression in HepG2, HuH7, HeLa, WISH, A549, VERO, CHO, and Balb/c 3T3 Cells: Further data showing that an altered coat protein enhances the ability of a non-mammalian DNA virus to direct expression of an exogenous gene in mammalian cells is provided by this example. Here, a variety of cells were infected with the VGZ3 baculovirus. The methods employed in these experiments first are described.

Cells: The human hepatoma lines HepG2 and HuH7, the human cervical carcinoma line HeLa, the human amniotic cell line WISH, the human lung carcinoma A549, the African green monkey kidney line VERO, the hamster epithelial line CHO and the mouse embryonic fibroblast line Balb/c 3T3 were all obtained from ATCC. All mammalian cells were grown in Dulbecco's Modified Eagle's Medium (GibcoBRL, Grand Island, N.Y.) with 10% fetal bovine serum and 4 mM glutamine (BioWhittaker, Walkersville, Md.), except for WISH cells, which were grown in MEM with Hanks's salts (GibcoBRL), 20% fetal bovine serum and 4 mM glutamine.

Infection and Reporter Gene Assay: Cells were seeded at $2 \times 10^5$ cells per well in 12-well plates. After the cells attached to the plastic, the cells were rinsed with medium and fresh complete medium was added. Viral infection was performed by adding virus to the medium at the indicated multiplicities of infection (moi). Following an 18–24 hour incubation at 37° C. in 5% CO2, cells were stained with X-gal to visualize β-galactosidase-expressing cells or cell lysates were taken and β-galactosidase activity quantitated by a luminescent β-galactosidase assay (Clontech catalog # K2048-1) according to the manufacturer's instructions.

Results: The use of the VGZ3 virus enhances exogenous gene expression, as compared with the level of gene expression obtained with the Z4 virus. X-gal staining of infected cells in culture indicated that an approximately 10-fold higher percentage of HepG2 cells expressed the exogenous gene following infection with VGZ3, as compared with the Z4 virus (data not shown). In addition, the intensity of the blue staining has greater in the VGZ3-treated cells, suggesting that a higher level of gene expression within the VGZ3-infected cells. Enhanced gene expression was also detected when the VGZ3 virus was used to infect HeLa cells. At an moi of 100, the Z4 virus produced few blue cells per well (approximately 1-5 cells), while approximately 10% of the VGZ3 cells stained blue with X-gal.

The results of a quantitative assay of β-galactosidase expression are shown in FIG. 22. At each moi tested, the level of β-galactosidase expression in HepG2 cells treated with VGZ3 was roughly 10-fold higher than the level obtained with the Z4 virus. The difference in transduction efficiency between the Z4 virus and the VGZ3 virus was even more notable in HeLa cells. At an moi of 1 or 10, no β-galactosidase activity above the background levels was detected with the Z4 virus. In contrast, β-galactosidase activity was detectable in HeLa cells treated with VGZ3 at an moi of 1. When the Z4 virus was used at an moi of 100, β-galactosidase activity just above background levels was detected. When the VGZ3 virus was used at an moi of 100, the level of β-galactosidase activity detected in HeLa cells was approximately 350 times greater than the level detected in Z4-treated cells.

A panel of 8 different cell lines was used to compare the transduction efficiencies of the Z4 and VGZ3 viruses at an moi of 50. At this low moi, exogenous gene expression is not detected in certain of the cell lines treated with the Z4 virus, as shown in Table 10. In contrast, the VGZ3 virus led to detectable levels of exogenous gene expression in all of the cell lines at an moi of 50. In sum, these data provide further evidence that an altered coat protein enhances exogenous gene expression from a non-mammalian DNA virus.

TABLE 10:

B-GALACTOSIDASE ACTIVITY IN Z4- AND VGZ3-TREATED CELLS

| | β-galactosidase activity[a] | |
|---|---|---|
| Cells | Z4-treated[b] | VG73-treated |
| HepG2 | 6.62 | 58.21 |
| HuH7 | 4.46 | 42.49 |
| HeLa | 0.05 | 2.67 |
| WISH | 0.00 | 1.85 |
| A549 | 0.22 | 46.34 |
| VERO | 0.58 | 6.38 |
| CHO | 0.00 | 2.33 |
| 3T3 | 0.02 | 2.01 |

[a]For each cell line, the β-galactosidase activity in uninfected cells was determined, and this value was subtracted from the raw numbers for β-galactosidase activity in Z4-treated and VGZ3-treated cells. Each data point represents the average of three samples.
[b]All Z4 and VGZ3 treatments were at an moi of 50.

Other Embodiments

Non-mammalian viruses other than the above-described *Autographa californica* viruses can be used in the invention; such viruses are listed in Table 1. Nuclear polyhedrosis viruses, such as multiple nucleocapsid viruses (MNPV) or single nucleocapsid viruses (SNPV), are preferred. In particular, *Choristoneura fumiferana* MNPV, *Mamestra brassicae* MNPV, *Buzura suppressaria* nuclear polyhedrosis virus, *Orgyia pseudotsugata* MNPV, *Bombyx mori* SNPV, *Heliothis zea* SNPV, and *Trichoplusia ni* SNPV can be used.

Granulosis viruses (GV), such as the following viruses, are also included among those that can be used in the invention: *Cryptophlebia leucotreta* GV, *Plodia interpunctella* GV, *Trichoplusia ni* GV, *Pieris brassicae* GV, *Artogeia rapae* GV, and *Cydia pomonella* granulosis virus (CpGV). Also, non-occluded baculoviruses (NOB), such as *Heliothis zea* NOB and *Oryctes rhinoceros* virus can be used.

Other insect (e.g., lepidopteran) and crustacean viruses can also be used in the invention. Further examples of useful viruses include those that have infect fungi (e.g., *Strongwellsea magna*) and spiders. Viruses that are similar to baculoviruses have been isolated from mites, Crustacea (e.g., *Careinus maenas, Callinectes sapidus*, the Yellow Head Baculovirus of penaeid shrimp, and *Penaeus monodon*-type baculovirus), and Coleoptera. Also useful in the invention is the *Lymantria dispar* baculovirus.

If desired, the virus can be engineered to facilitate targeting of the virus to certain cell types. For example, ligands that bind to cell surface receptors other than the ASGP-R can be expressed on the surface of the virion. Alternatively, the virus can be chemically modified to target the virus to a particular receptor.

If desired, the cell to be infected can first be stimulated to be mitotically active. In culture, agents such as chloroform can be used to this effect; in vivo, stimulation of liver cell division, for example, can be induced by partial hepatectomy (see, e.g., Wilson, et al., 1992, J. Biol. Chem. 267:11283–11489). Optionally, the virus genome can be engineered to carry a herpes simplex virus thymidine kinase gene; this would allow cells harboring the virus genome to be killed by gancicylovir. If desired, the virus could be engineered such that it is defective in growing on its natural non-mammalian host cell (e.g., insect cell). Such strains of viruses could provide added safety and be propagated on a complementing packaging line. For example, a defective baculovirus could be made in which an immediate early gene, such as IE1, has been deleted. This deletion can be made by targeted recombination in yeast or *E. coli*, and the defective virus can be replicated in insect cells in which the IE1 gene product is supplied in trans. If desired, the virus can be treated with neuraminidase to reveal additional terminal galactose residues prior to infection (see, e.g., Morell et al., 1971, J. Biol. Chem. 246:1461–1467).

What is claimed is:

1. A method of treating a disorder in a mammal, comprising:
   a) introducing into a cell a therapeutically effective amount of a non-mammalian DNA virus to produce an infected cell, wherein the virus has an altered coat protein, and the genome of the virus comprises an exogenous gene; and
   b) maintaining said infected cell under conditions such that said exogenous gene is expressed in said mammal.

2. The method of claim 1, wherein the altered coat protein comprises a coat protein of a mammalian virus.

3. The method of claim 1, wherein the altered coat protein is a fusion protein.

4. The method of claim 1, wherein said virus is an insect virus.

5. The method of claim 4, wherein said insect virus is a baculovirus.

6. A method for treating a cancer in a mammal, said method comprising:
   a) introducing into a cancerous cell of said mammal a non-mammalian DNA virus having an altered coat protein to produce an infected cell, wherein the genome of said virus comprises a cancer-therapeutic gene encoding a protein selected from the group consisting of tumor necrosis factor, p53, thymidine kinase, diphtheria toxin chimeras, and cytosine deaminase; and
   b) maintaining said infected cell in said mammal under conditions such that said cancer-therapeutic gene is expressed.

7. The method of claim 6, wherein the altered coat protein comprises a coat protein of a mammalian virus.

8. The method of claim 6, wherein the altered coat protein comprises a fusion protein.

9. The method of claim 6, wherein said cancerous cell is selected from the group consisting of hepatocytes, pancreas cells, lung cells, thyroid cells, thymus cells, prostate tissue cells, breast tissue cells, brain cells, neuronal cells, glial cells, skin cells, spleen cells, muscle cells, kidney cells, and bladder cells.

10. The method of claim 6, wherein the non-mammalian DNA virus is an insect virus.

11. The method of claim 10, wherein said insect virus is a baculovirus.

12. A method for treating a neurological disorder in a mammal, said method comprising:
   a) introducing into a cell a therapeutically effective amount of a non-mammalian DNA virus having an altered coat protein to produce an infected cell, wherein the genome of said virus comprises an exogenous gene encoding a therapeutic protein selected from the group consisting of nerve growth factor, hypoxanthine guanine phosphoribosyl transferase, tyrosine hydroxylase, dopadecarboxylase, brain-derived neurotrophic factor, and basic fibroblast growth factor; and
   b) maintaining said infected cell under conditions such that said exogenous gene is expressed in said mammal.

13. The method of claim 12, wherein said virus is an insect virus.

14. The method of claim 13, wherein said insect virus is a baculovirus.

15. The method of claim 12, wherein said altered coat protein comprises a coat protein of a mammalian virus.

16. The method of claim 12, wherein the altered coat protein comprises a fusion protein.

17. A pharmaceutical composition comprising:
   (A) a pharmaceutically acceptable excipient and
   (B) a non-mammalian DNA virus, wherein the genome of the virus comprises:
      an exogenous mammalian gene;
      an exogenous mammalian-active promoter operably linked to said exogenous mammalian gene; and
      a gene encoding an altered coat protein.

18. The pharmaceutical composition of claim 17, wherein said virus is an insect virus.

19. The pharmaceutical composition of claim 18, wherein said insect virus is a baculovirus.

20. The pharmaceutical composition of claim 17, wherein the altered coat protein comprises the coat protein of a mammalian virus.

21. The pharmaceutical composition of claim 17, wherein the gene encoding the altered coat protein encodes a fusion protein.

* * * * *